(12) United States Patent
Tominaga et al.

(10) Patent No.: US 11,597,943 B2
(45) Date of Patent: Mar. 7, 2023

(54) TRANSGENIC PLANT EXHIBITING ENHANCED GROWTH AND METHOD FOR PRODUCING SAME

(71) Applicants: WASEDA UNIVERSITY, Tokyo (JP); NATIONAL UNIVERSITY CORPORATION CHIBA UNIVERSITY, Chiba (JP)

(72) Inventors: Motoki Tominaga, Tokyo (JP); Kohji Ito, Chiba (JP)

(73) Assignees: WASEDA UNIVERSITY, Tokyo (JP); NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 77 days.

(21) Appl. No.: 16/828,146

(22) Filed: Mar. 24, 2020

(65) Prior Publication Data
US 2020/0277618 A1    Sep. 3, 2020

Related U.S. Application Data

(63) Continuation-in-part of application No. PCT/JP2019/001491, filed on Jan. 18, 2019.

(30) Foreign Application Priority Data

Jan. 22, 2018 (JP) .............................. JP2018-007923

(51) Int. Cl.
C12N 15/82        (2006.01)

(52) U.S. Cl.
CPC .............................. *C12N 15/8262* (2013.01)

(58) Field of Classification Search
None
See application file for complete search history.

(56) References Cited

U.S. PATENT DOCUMENTS 10,087,457 B2 * 10/2018 Tominaga .......... C12N 15/8261
2013/0007915 A1 * 1/2013 Tominaga .......... C07K 14/4716
800/290

OTHER PUBLICATIONS

Chida et al., "Expression of the Algal Cytochrome c6 Gene iin *Arabidopsis* Enhances Photosynthesis and Growth", Plant Cell Physiol, 2007, 48(7); pp. 948-957.

Draper et al., "Brachypodium distachyon. A New Model System for Functional Genomics in Grasses", Plant Physiology, 2001, vol. 127, pp. 1539-1555.
Duan et al., "Technology for increase in production of Biomass by controlling protoplasmic streaming: Controlling plant size by speed-modification of myosin XI", 2017, vol. 68, No. 6, pp. 444-468, Jun. 2017.
Hugashi-Fujime et al., "The fastest actin-based motor protein from the green algae, *Chara*, and its distinct mode of interaction with actin", FEBS Lett., 1995, vol. 375, No. 1-2, pp. 151-154.
International Search Report for corresponding PCT/JP2019/001491; dated Apr. 16, 2019.
Ito, "Development of plant growth promotion system by increasing cytoplasmic streaming speed", Annual report of Venture Business Laboratory, Chiba University, No. 15, pp. 92-94, (2015).
Ito, et al., "Unique charge distribution in surface loops confers high velocity on the fast motor protein Chara myosin", Proc. Natl. Acad. Sci., USA, 2009, vol. 106, No. 51, pp. 21585-21590.
Kashiyama, et al., "Functional expression of a chimeric myosin-containing motor domain of Chara myosin and neck and tail domains of Dictyostelium myosin II", J. Mol. Biol., 2001, vol. 311, No. 3, pp. 461-466.
Meinke et al., "*Arabidopsis thaliana*: A Model Plant for Genome Analysis", 1998, Science, vol. 282, pp. 662, 679-682.
Miyagawa et al., "Overexpression of a cyanobacterial fuctose-1, 6-/sedoheptulose-1,7-bisphosphatas in tobacco enhances photosynthesis and growth", Nature Biotechnol, vol. 19, Oct. 2001, pp. 965-969.
Tamanaha, et al, "Functional analysis of myosin XI in *Chara bruanii* (Chara), the fastest myosin in the living world", Proceedings of the 80th Annual Meeting of the Botanical Society of Japan, vol. 80th, p. 196, P-0915, (2016).
Tominaga, "The size of plant is determined by the speed of myosin motor," Biophysics, vol. 54, No. 5, pp. 259-261, May 23, 2014.
Tominaga, et al "Light utilizing strategy of plants considering from growth control by cytoplastic streaming," The Japanese Society of Photosynthesis Research, 2015, vol. 25, No. 1,pp. 42-47.

* cited by examiner

*Primary Examiner* — Elizabeth F McElwain
(74) *Attorney, Agent, or Firm* — Cantor Colburn LLP

(57) ABSTRACT

A transgenic plant which exhibits a growth capacity which is enhanced compared to that of a host plant, and has a chimeric protein of a peptide containing an amino acid sequence derived from a motor domain of myosin XI of a donor plant 1, which is a plant species other than the host plant, and a peptide containing an amino acid sequence derived from a domain other than the motor domain of myosin XI of a donor plant 2, which is the host plant or a plant species other than the host plant, the transgenic plant being characterized in that the motor domain loop 2 region has EEPKQGGKGGGKSSFSSIG or EEPKQGGGKGG-SKSSFSSIG, and in addition to these sequences, has an amino acid sequence in which one to six amino acids have been deleted, replaced or added.

7 Claims, 7 Drawing Sheets
Specification includes a Sequence Listing.

FIG.1A
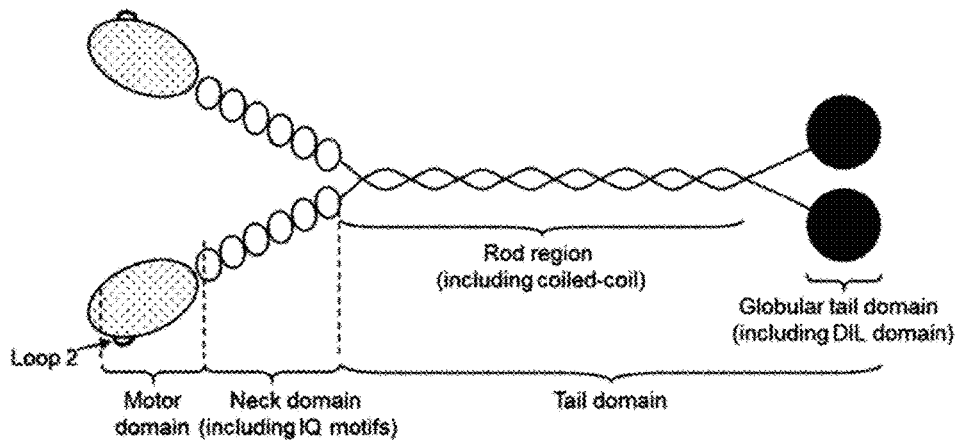
FIG.1B
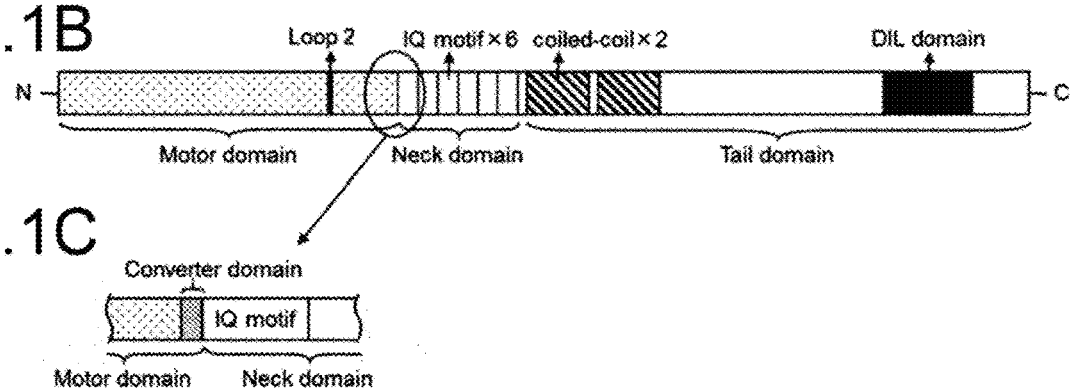
FIG.1C
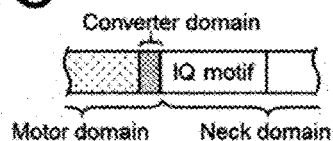
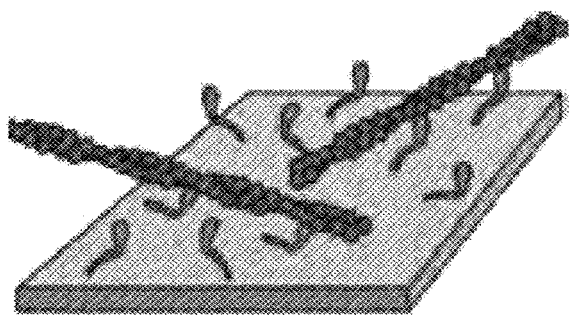
FIG.2

Arabidopsis Myosin
MYA2
Loop2: FPPMSDDSKQSKFSSIG (net charge of loop2 is 0) (SEQ ID NO 42)
Loop3: KPKLAR (net charge of loop 2: +3) (SEQ ID NO 43)

High velocity myosin
CbM1
Loop2: YPPPEEPKQGGKGGGKSSFSSIG (net charge: +1) ) (SEQ ID NO 44)
Loop3: KHKFKK (net charge of loop 3: +5) (SEQ ID NO 45)

CaM5049
Loop2: YPPPEEPKQGGKGGGKSSFSSIG (net charge of loop2: +1) (SEQ ID NO 46)
Loop3: KHKFKK (net charge of loop 3: +5) (SEQ ID NO 47)

CbM2
Loop2: YPPPPEEPKQGGGKGGSKSSFSSIG (net charge of loop2: +1) (SEQ ID NO 48)
Loop3: KHKFKK (net charge of loop 3: +5) (SEQ ID NO 49)

Low velocity myosin
CbM3
Loop2: FPPDEGTKAPSKFASIG (net charge of loop2: 0) (SEQ ID NO 50)
Loop3: RPKFKR (net charge of loop 3: +4) (SEQ ID NO 51)

CaM5408
Loop2: FPPDEGTKAPSKFASIG (net charge of loop2: 0) (SEQ ID NO 52)
Loop3: RPKFKR (net charge of loop 3: +4) (SEQ ID NO 53)

CaM5627
Loop2: FPPDEGTKAPSKFASIG (net charge of loop2: 0) (SEQ ID NO 54)
Loop3: RPKFKR (net charge of loop 3: +4) (SEQ ID NO 55)

CcM
Loop2: FPADEGTKAPSKFMSIG (net charge of loop2: 0) (SEQ ID NO 56)
Loop3: KHKFKR (net charge of loop 3: +5) (SEQ ID NO 57)

CbM4
Loop2: FPLDEGAKAPSKFMSIG (net charge of loop2: 0) (SEQ ID NO 58)
Loop3: KHKFKR (net charge of loop 3: +5) (SEQ ID NO 59)

CaM5639
Loop2: FPADEGTKAPSKFMSIG (net charge of loop2: 0) (SEQ ID NO 60)
Loop3: KHKFKR (net charge of loop 3: +5) (SEQ ID NO 61)

FIG.4

TRANSGENIC PLANT EXHIBITING ENHANCED GROWTH AND METHOD FOR PRODUCING SAME

CROSS-REFERENCE TO RELATED APPLICATIONS

The present application is a continuation-in-part application of International Application No. PCT/JP2019/001491, filed Jan. 18, 2019, which claims priority to Japanese Patent Application No. 2018-007923, filed Jan. 22, 2018. The contents of these applications is incorporated herein by reference in their entirety.

BACKGROUND OF THE INVENTION

Field of the Invention

The present invention relates to a transgenic plant exhibiting enhanced growth and a method for producing same.

Techniques that promote plant growth are very important for agriculture, forestry, and biomass energy industries because they increase the amount of plant biomass. Thus, for example, various attempts have been made such as production of transgenic plants and knockout plants by optimization of cultivation conditions, treatment with plant hormones, modification of endogenous genes, introduction of exogenous genes, etc.

There are inventions related to enlargement of transgenic plants by introduction of exogenous genes (Non-Patent Documents 1 and 2: Nature Biotechnol, 2001, 19: 965-969 by Miyagawa et al.; and Plant Cell Physiol, 2007, 48: 948-957 by Chida et al.). In many cases, exogeneous genes that have conventionally been introduced into tobacco, *Arabidopsis thaliana*, rice, corn, etc. in the technology for enlarging plants are genes encoding proteins involved in the photosynthetic pathway as described, for example, in Non-Patent Documents 1 and 2. However, there is a problem in the method for increasing the size of plants by enhancing the photosynthetic pathway. This is because even if the photosynthetic ability of leaves can be improved, only a limited effect is exhibited in the whole plant. Furthermore, as a result of the accumulation of photosynthetic products in the leaves, the improvement in photosynthetic capacity is attenuated with time by the feedback effect.

The present inventors presumed that the velocity of cytoplasmic streaming should become a rate-determining factor for growth in plant cells, and focused on the velocity of movement on the actin of myosin XI of plant cells. The movement velocity of myosin in *Chara corallina* on the actin is very high. In addition, *Brachypodium distachyon* as a monocotyledonous plant and *Arabidopsis thaliana* as a dicotyledonous plant have been used as experimental plant models (Non-Patent documents 3, 4: Plant Physiology, 2001, 127: 1539-1555 by Draper J. et al.; and Science, 282 (5389), 1998, 662: 679-82 by Meinke D W et al.), since genetic and physiological characteristics thereof have been elucidated. Then, the present inventors selected *Brachypodium distachyon* or *Arabidopsis thaliana* as a host plant, and selected myosin XI domains of these plants other than the motor domain, and *Chara corallina* was selected as a donor plant of the myosin XI motor domain. An attempt was made by the inventors to introduce a gene encoding the chimeric protein into the host plant for the purpose of expressing the chimeric protein in combination with the domains in the host plant. As a result, for both *Brachypodium distachyon* and *Arabidopsis thaliana*, the inventors succeeded in producing transgenic plants with enhanced growth and increased size compared to the wild type (Patent Document 1: US Unexamined Patent Application Publication No. US2013/0007915).

SUMMARY OF THE INVENTION

The problems to be solved by the present invention are to establish a method for producing a transgenic plant having a further enhanced growth capacity as compared to a plant produced by the conventional production methods, and to provide a plant having a further enhanced growth capacity.

The present inventors have found out that the myosin XI motor domain of *Chara* (*Chara braunii* or *Chara australis*) selected as the motor domain of the donor plant of myosin XI protein can move at higher velocity (hereinafter referred to as "new high-velocity motor domain"), compared to the motor domain of *Chara corallina*. Then, *Brachypodium distachyon* and *Arabidopsis thaliana* were selected as the host plants, and so as to express a chimeric protein of the combination of the domains of myosin XI other than the motor domain with the high-velocity motor domain, the gene encoding the chimeric protein was introduced into the host plants. As a result, the present inventors have found out that the host plant expressing the chimeric protein having the new high-velocity motor domain can produce a transgenic plant having enhanced growth capacity compared to a wild-type host plant.

Furthermore, the present inventors have intensively studied a mechanism for producing a plant having growth capacity enhanced by the new high-velocity motor domain. As a result, the inventors have found out that, in the new high-velocity motor domain, the amino acid sequence of the loop 2 region has high sequence identity, while the identity of the amino acid sequence of the loop 2 region between the new high-velocity motor domain and the high-velocity motor domain mentioned above are not high.

Furthermore, the present inventors have found out that the ATPase activity of the motor domain has a positive correlation with the movement velocity, and thus accomplished the present invention.

Specifically, the present invention provides a transgenic plant having a growth capacity of a host plant enhanced, which has a chimeric protein including;
a peptide containing an amino acid sequence derived from a motor domain of myosin XI of a donor plant 1 which is a plant species other than the host plant, and
a peptide containing an amino acid sequence derived from a domain other than the motor domain of myosin XI of donor plant 2 which is a plant species other than the host plant or the host plant,
wherein a loop 2 region of the motor domain has an amino acid sequence EEPKQGGKGGGKSSFSSIG (SEQ ID NO: 36) or EEPKQGGGKGGSKSSFSSIG (SEQ ID NO: 37), or one in which a plurality of amino acids of the sequences thereof are deleted, substituted and/or added.

In the transgenic plant of the present invention, the motor domain may have a peptide having any one of the following amino acid sequences (i) to (iii):
(i) the amino acid sequence represented by any one of SEQ ID NOs: 14, 16 and 18;
(ii) an amino acid sequence having 85% or more identity with the amino acid sequence represented by any one of SEQ ID NOs: 14, 16 and 18; and (iii) An amino acid sequence in which a plurality of amino acids in the amino acid sequence represented by any one of SEQ ID NOs: 14, 16 and 18 are deleted, substituted, and/or added.

In the transgenic plant of the present invention, the velocity of movement of the motor domain alone of the chimeric protein in an in vitro motility assay, in which the motor domain binds to and moves on actin, may be 4 times or more compared to the velocity of movement of the motor domain alone of the myosin XI protein of the wild-type host plant in an in vitro motility assay, or 6 µm/sec or more at a temperature of 25° C.

In the transgenic plant of the present invention, the donor plant 1 for the motor domain of the myosin XI protein may be *Chara* (*Chara braunii* or *Chara australis*).

In the transgenic plant of the present invention, the chimeric protein may include the neck domain, rod domain and globular tail domain of the myosin XI protein of the donor plant 2 which is the host plant or a plant species other than the host plant, and include the motor domain derived from the donor plant 1.

In the transgenic plant of the present invention, Vmax of the actin-activating ATPase activity of the motor domain may be 150 Pi/sec or more.

In the transgenic plant of the present invention, the host plant and/or donor plant 2 may be a monocotyledonous plant or a dicotyledonous plant.

In the transgenic plant of the present invention, the monocotyledonous plant may be one species selected from the group consisting of *Brachypodium distachyon, Oryza sativa, Triticum aestivum, Triticale, Hordeum vulgare, Avena sativa, Secale cereale, Sorghum bicolor, Panicum miliaceum, Saccharum officinarum* and *Zea mays*.

In the transgenic plant of the present invention, the dicotyledonous plant may be one species selected from the group consisting of *Arabidopsis thaliana, Nicotiana tabacum, Solanum lycopersicum, Solanum tuberosum, Legume, Glycine max, Daucus carota, Manihot esculenta, Medicago sativa* and *Gossypium*.

The present invention also provides a method for producing a transgenic plant with a growth capacity of a host plant enhanced, including;
introducing a gene encoding a chimeric protein including;
a peptide containing an amino acid sequence derived from the motor domain of myosin XI of donor plant 1 which is a plant species other than the host plant, and
a peptide containing an amino acid sequence derived from a domain other than the motor domain of myosin XI of donor plant 2 which is the host plant or other than the host plant,
wherein a loop 2 region of the motor domain has an amino acid sequence EEPKQGGKGGGKSSFSSIG (SEQ ID NO: 36) or EEPKQGGGKGGSKSSFSSIG (SEQ ID NO: 37), or one in which a plurality of amino acids of the sequences thereof are deleted, substituted and/or added.

In the method of the present invention, the motor domain may have a peptide encoded by any one of the following nucleic acid sequences (i) to (iii):
(i) the nucleic acid sequence represented by any one of SEQ ID NOs: 13, 15 and 171;
(ii) a nucleic acid sequence having 85% or more identity with the nucleic acid sequence represented by any one of SEQ ID NOs: 13, 15 and 17; and
(iii) a nucleic acid sequence in which a plurality of nucleic acids in the nucleic acid sequence represented by any one of SEQ ID NOs: 13, 15 and 17 are deleted, substituted, and/or added.

In the method of the present invention, the velocity of movement of the motor domain alone of the chimeric protein in an in vitro motility assay, in which the motor domain binds to and moves on actin, may be 4 times or more compared to the velocity of movement of the motor domain alone of the myosin XI protein of the wild-type host plant in an in vitro motility assay, or 6 µm/sec or more at a temperature of 25° C.

In the method of the present invention, Vmax of the actin-activating ATPase activity of the motor domain may be 150 Pi/sec or more.

In the method of the present invention, the donor plant 1 for the motor domain may be *Chara* (*Chara braunii* or *Chara australis*).

The chimeric protein may include: a neck domain, a rod domain and a globular tail domain of the myosin XI protein of the donor plant 2 which is a species of the host plant or a plant species other than the host plant; and include the motor domain of the myosin XI protein of the donor plant 1.

In the method of the present invention, the host plant and/or donor plant 2 may be a monocotyledonous plant or a dicotyledonous plant.

In the method of the present invention, the monocotyledonous plant may be one species selected from the group consisting of *Brachypodium distachyon, Oryza sativa, Triticum aestivum, Triticale, Hordeum vulgare, Avena sativa, Secale cereale, Sorghum bicolor, Panicum miliaceum* (millet), *Saccharum officinarum* and *Zea mays*.

In the method of the present invention, the dicotyledonous plant may be one species selected from the group consisting of *Arabidopsis thaliana, Nicotiana tabacum, Solanum lycopersicum, Solanum tuberosum, Legume, Glycine max, Daucus carota, Manihot esculenta, Medicago sativa* and *Gossypium*.

Furthermore, the present invention provides the transgenic plant produced by the said producing method.

The present invention also provides a transgenic plant which is a passage from the transgenic plant.

The present invention also provides a progeny from the transgenic plant.

BRIEF DESCRIPTION OF THE DRAWINGS

FIG. 1A represents the structure of a plant myosin XI molecule (dimer).

FIG. 1B represents the structure of a plant myosin XI protein (monomer polypeptide).

FIG. 1C is an enlarged view of a circled portion of FIG. 1B. This region contains a converter domain that is important as a link between the motor domain and the neck domain to construct the chimeric myosin XI protein of the invention.

FIG. 2 represents a schematic diagram of an experimental system for measuring the movement velocity of the motor domain of myosin XI moving on actin.

FIG. 4 represents loop 2 region amino acid sequences (amino acid sequence of the first row of each myosin; SEQ ID NOs 42, 44, 46, 48, 50, 52, 54, 56, 58, and 60) and loop 3 region amino acid sequences (amino acid sequence of the second row of each myosin; SEQ ID NOs 43, 45, 47, 49, 51, 53, 55, 57, 59, and 61) of *Arabidopsis* myosin and *Chara* myosin XIs, the relationship between the net charges of loop 2 and loop 3 and the velocity of the motor domain of *Chara* myosin XIs.

DETAILED DESCRIPTION OF THE INVENTION

Figure 3:
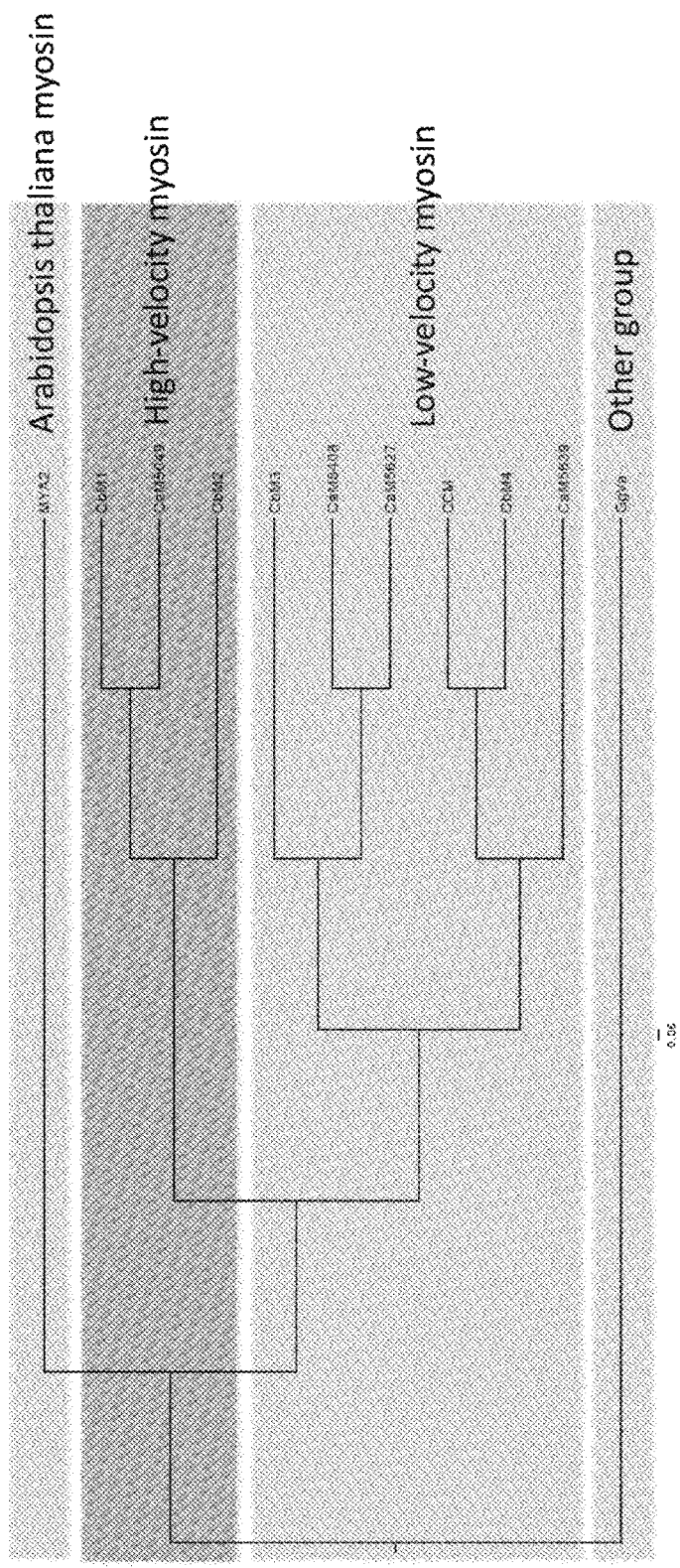
FIG. 3 is a view representing lineage relationship between *Arabidopsis thaliana* MYA2 and *Chara* myosin XIs.

1. Transgenic Plant with Enhanced Growth Capacity

One embodiment of the present invention is a transgenic plant with a growth capacity of a host plant enhanced, which has a chimeric protein including a peptide containing an amino acid sequence derived from the motor domain of myosin XI of donor plant 1 which is a plant species other than the host plant, and a peptide containing an amino acid sequence derived from the domain other than the motor domain of myosin XI of donor plant 2 which is a plant species other than the host plant or the host plant, wherein a loop 2 region of the motor domain has an amino acid sequence EEPKQGGKGGGKSSFSSIG (SEQ ID NO: 36) or EEPKQGGGKGGSKSSFSSIG (SEQ ID NO: 37), or one in which a plurality of amino acids of the sequences thereof are deleted, substituted and/or added.

This EEPKQGGKGGGKSSFSSIG (SEQ ID NO: 36) or EEPKQGGGKGGSKSSFSSIG (SEQ ID NO: 37) in the loop 2 region of the motor domain of the myosin XI protein was not recognized in the loop region of the high-speed type *Chara corallina* described in Patent Document 1, and an amino acid sequence having a high sequence identity with this amino acid sequence is observed in the loop 2 region of the *Chara braunii* described in the example mentioned below (see FIG. 4).

When the on-actin movement velocities of the motor domain of myosin XI protein comprising a peptide represented by the amino acid sequence of SEQ ID NOs: 14, 16 and 18 derived from *Chara braunii* are compared to the velocities of the motor domain derived from the high-velocity type *Chara corallina*, the velocity ratio is 2 times or more, preferably 2.75 times or more. When compared to the velocities of the motor domain derived from myosin XI of the wild-type host plant, the velocity ratio is 4 times or more, or 6 µm/sec or more at a temperature of 25° C.

Therefore, in the new high-speed transgenic plant of the present invention, the motor domain may have a peptide having any one of the following amino acid sequences (i) to (iii):

(i) the amino acid sequence represented by any one of SEQ ID NOs: 14, 16 and 18;

(ii) an amino acid sequence having 80% or more, preferably 85% or more, more preferably 90% or more, most preferably 95% or more identity with the amino acid sequence represented by any one of SEQ ID NOs: 14, 16 and 18; and (iii) an amino acid sequence in which a plurality of amino acids, preferably 1 to 6 amino acids in the amino acid sequence represented by any one of SEQ ID NOs: 14, 16 and 18, are deleted, substituted, and/or added.

The myosin represented by SEQ ID NOs: 14, 16 and 18 have close sequences in the molecular phylogenetic tree of the motor domain of myosin XI, and are classified into a different taxonomic group from the motor domain of myosin XI of *Chara corallina* of the genus *Chara* having a motor domain of a high-velocity myosin XI protein described in the examples of Patent Document 1.

As used herein, the term "a plant with enhanced growth capacity" refers to a transgenic plant that has a host plant transformed, into which a vector containing a nucleic acid sequence encoding the amino acid sequence of the chimeric protein has been introduced so that the chimeric protein containing the motor domain of the myosin XI protein of a *Chara* defined by the above amino acid sequences is expressed, and exhibits characteristics of an increased leaf size, leaf number, spikelet number and/or dry weight after it has been grown in the same environment and in the same period as compared to a wild-type plant. The enhanced growth capacity may be an improvement in the growth of the whole plant or an enhancement of the growth of a part of the plant.

The "host plant" refers to a plant that is transformed by expressing the chimeric protein, i.e., a plant that is to be provided with enhanced growth capacity by transformation. The "host plant" refers to a plant other than a *Chara*, but is not particularly limited as long as it is a plant other than a *Chara*. For example, it may be a monocotyledonous plant or a dicotyledonous plant.

As used herein, "donor plant" refers to a plant that provides amino acid sequence or nucleic acid sequence information for designing the amino acid sequence of the myosin XI chimeric protein according to the present invention. In particular, a plant that provides amino acid sequence information including the motor domain of myosin XI protein or nucleic acid sequence information encoding the amino acid sequence is represented as a donor plant 1. And a plant that provides the amino acid sequence of a peptide including a neck domain, a rod domain, and a globular tail domain or the polynucleotide sequence information encoding the said amino acid sequence is referred to as a donor plant 2.

Examples of monocotyledonous plants used as the host plant and/or donor plant 2 include *Brachypodium distachyon, Oryza sativa, Triticum aestivum, Triticale, Hordeum vulgare, Avena sativa, Secale cereale, Sorghum bicolor, Panicum miliaceum, Saccharum officinarum* and *Zea mays*, etc., but not limited thereto.

Examples of dicotyledonous plants used as the host plant and/or donor plant 2 include, but are not limited to, *Arabidopsis thaliana, Nicotiana tabacum, Solanum lycopersicum, Solanum tuberosum, Legume, Glycine max, Daucus carota, Manihot esculenta, Medicago sativa* and *Gossypium*, etc.

As the donor plant 1 that provides the amino acid sequence of the motor domain of the myosin XI protein, *Chara* is preferred.

For the donor plant 2 that provides the amino acid sequence of a peptide including a neck domain, a rod domain, and a globular tail domain, the host plant and the donor plant 2 may be the same or different from each other, and the donor plant 2 is not limited to only one type, but two or more types of plants can be used. In a typical case, the plant species providing the neck domain may be different from the plant species providing the tail domain (including the rod domain and the globular tail domain). In such cases, the domains derived from the respective plant species may be derived from different types of myosin XI. For example, if the donor plant 2 providing a neck domain (referred to as "plant A") and the donor plant 2 providing a tail domain (referred to as "plant B") are used, and the neck domain is derived from a myosin XI-1 protein of plant A, the tail domain may be derived from plant B myosin XI-2 protein.

Preferably, the domains other than the motor domain of the chimeric myosin XI protein are derived from the same myosin XI in the plant species related to the donor plant 2. For example, if the neck domain is derived from plant A myosin XI-1 protein, the tail domain is also preferably derived from plant A myosin XI-1 protein. This is because the same myosin XI type protein (orthologous protein) has the same function even if it is a different species, and can exert the similar effect. Preferably, the donor plant 2 is a plant belonging to the same family as the host plant. More preferably, the donor plant 2 is a plant belonging to the same genus as the host plant. Even more preferably, the donor plant 2 is the same plant as the host plant. Thus, it is most preferred that the neck domain, rod domain and globular tail domain are all derived from the host plant myosin XI protein.

Examples of more specific monocotyledons of donor plant 2 that provide the amino acid sequence of a peptide containing a neck domain, a rod domain and a globular tail domain include, but not limited to, *Brachypodium distachyon, Oryza sativa, Triticum aestivum, Triticale, Hordeum vulgare, Avena sativa, Secale cereale, Sorghum bicolor, Panicum miliaceum, Saccharum officinarum* and *Zea mays*, etc.

Examples of more specific dicotyledons of donor plant 2 that provide the amino acid sequence of a peptide containing a neck domain, a rod domain and a globular tail domain include, but not limited to, *Arabidopsis thaliana, Nicotiana tabacum, Solanum lycopersicum, Solanum tuberosum, Legume, Glycine max, Daucus carota, Manihot esculenta, Medicago sativa* and *Gossypium*, etc.

Among these plants, because their genetic and physiological properties have already been elucidated, *Brachypodium distachyon* is used as an experimental plant model for monocotyledonous plants and *Arabidopsis thaliana* is used as an experimental plant model for dicotyledonous plants. (Non-Patent Documents 3 and 4).

The new high-velocity type transgenic plant of the present invention is obtained by introducing into a host plant and expressing a chimeric gene encoding a chimeric protein, which is a linked combination of regions other than the motor domain of the myosin XI protein of the donor plant 2, specifically, the neck domain, the rod domain, and the globular tail domain, with the motor domain of the myosin XI protein derived from the *Chara* specified by the amino acid sequence mentioned above.

Therefore, the chimeric protein to be expressed in the host plant in order to obtain the new high-velocity transgenic plant of the present invention is a protein including the motor domain of the myosin XI protein derived from *Chara* specified by the above sequence, and including a neck domain, a rod domain and a globular tail domain of myosin XI protein derived from the donor plant 2. The chimeric protein has an activity of binding to actin and moving on actin at a high velocity.

In the present description, the "new high-velocity myosin XI protein" and the "new high-velocity motor domain" refer to myosin XI protein and the motor domain in which the motor domain of this myosin XI protein binds to actin and moves on actin at higher velocity of movement than that of the conventionally known myosin XI protein. On the other hand, in the present description, "high-velocity type" of "myosin XI protein" and "motor domain" are "myosin XI protein" and "motor domain" in which motor domain binds to actin and moves on actin at the velocity of the chimeric proteins described in Patent Document 1 etc.

Plant myosin XI protein has ATPase activity and actin binding site in its motor domain. After binding of myosin XI protein to actin protein, ATP as high-energy phosphates is hydrolyzed to produce ADP and a phosphate, and myosin XI protein moves on the actin. This movement causes cytoplasmic streaming in a plant cell, and the velocity of movement of myosin XI protein on actin is considered to be the rate-limiting factor of cytoplasmic streaming. This increase in the velocity of cytoplasmic streaming, i.e., increase in the velocity of movement of myosin XI protein that moves on actin, enhances plant growth, and also decrease in velocity of movement of myosin XI protein suppresses plant growth. These have been proved by the present inventors and shown in Patent Document 1.

Accordingly, a chimeric gene encoding a chimeric protein including a motor domain of myosin XI protein that moves on actin at higher velocity and domains other than the motor domain of myosin XI protein of donor plant 2 is introduced into the host plant, and the chimeric protein in which a high-speed myosin XI motor domain is fused in a cell can be expressed to bring about growth promotion in the transgenic plant with the host plant transformed.

The amino acid sequence of SEQ ID NO: 14 represents myosin XI protein (hereinafter referred to as "CbM1") of *Chara: Chara braunii*, and the amino acid sequence of SEQ ID NO: 16 represents myosin XI protein (hereinafter referred to as "CbM2") of other myosin XI of *Chara: Chara braunii*. The amino acid sequence of SEQ ID NO: 18 represents the myosin XI protein of other species of *Chara: Chara australis* (hereinafter referred to as "CaM"). And the amino acid sequences of the loop 2 region of the motor domain of these myosin XI proteins include amino acid sequences having high sequence identity with EEPKQGGKGGGKSSFSSIG (SEQ ID NO: 36) and EEPKQGGGKGGSKSSFSSIG (SEQ ID NO: 37) in common. On the other hand, the loop 2 regions of the myosin XI proteins that are other than CbM1 and CbM2 and slow even if it is that of the *Chara* classified as *Chara braunii*, and the myosin XI protein of the *Chara* (*Chara corallina*) (hereinafter referred to as "CcM") described in the example of Patent Document 1, do not have high sequence identity to the amino acid sequence of the loop 2 region of the high-velocity myosin XI protein described above.

Cytoplasmic streaming of *Chara* is the fastest of all plants, and has the myosin XI proteins that move the fastest on actin. Among them, the myosin XI protein of *Chara*, whose amino acid sequence of the motor domain is represented by SEQ ID NOs: 14, 16 or 18, is a new high-velocity type motor domain that moves particularly fast on actin. The loop 2 region of this motor domain has EEPKQGGKGGGKSSFSSIG (SEQ ID NO: 36) or EEPKQGGGKGGSKSSFSSIG (SEQ ID NO: 37), or a sequence having high sequence identity to these amino acid sequences.

Accordingly, in the new high-velocity transgenic plant of the present invention, examples of the chimeric protein include the neck domain, rod domain and globular tail domain of the myosin XI protein of donor plant 2, and contains a motor domain derived from the donor plant 1 *Chara* (*Chara braunii* or *Chara australis*), as shown in FIG. 1.

In the new high-velocity transgenic plant of the present invention, the movement velocity of the motor domain alone of the chimeric protein in the in vitro motility assay, in which the motor domain binds to actin and moves on the actin, is 4 times or more, preferably 6 times or more, more preferably 8 times or more compared to the movement velocity of the motor domain alone of myosin protein of the wild type host plant, or the movement velocity of the motor domain alone of the chimeric protein is 6 µm/sec or more, preferably 9 µm/sec or more, more preferably 12 µm/sec or more at a temperature of 25° C. in the in vitro motility assay in which the motor domain binds to actin and moves on the actin. This movement velocity is higher than the high-velocity type movement of the motor domain alone (4.8 µm/sec) described in Patent Document 1 as shown in the examples, mentioned below. It is actually about twice as high when it is 9 µm/sec. It is about 3 times faster when it is 12 µm/sec.

Moreover, compared to the movement velocity of the wild-type myosin XI motor domain, which is about 1.6 µm/sec, the velocity is actually about 5 times when it is 9 µm/sec and about 8 times when it is 12 µm/sec.

In addition, when the motor domain of myosin XI protein moves on actin, ATP is hydrolyzed to ADP and phosphate by ATPase contained in the motor domain. In the new high-velocity transgenic plant of the present invention having the motor domain derived from the *Chara* mentioned above, the Vmax of the actin-activating ATPase activity of the motor domain of the chimeric protein regarding the present invention is 150 Pi/sec or more, preferably over 200 Pi/sec at a temperature of 25° C.

Then, a chimeric gene encoding a chimeric protein that combines a motor domain of a *Chara* specified by the above amino acid sequences with a neck domain, a rod domain, and a globular tail domain of myosin XI protein of *Brachypodium distachyon*, which is widely used as an experimental plant model for monocotyledons, was created.

In addition, a chimeric gene encoding the high-velocity type chimeric protein shown in Patent document 1, was expressed in *Arabidopsis thaliana*, as a host plant, which is an experimental plant model of dicotyledonous plants. As a result, an increase in the size of the plant body was recognized as compared to wild-type *Arabidopsis thaliana*.

Accordingly, the new high-velocity chimeric protein of the present invention having a motor domain of the myosin XI protein of the *Chara* newly produced by the present inventors can be widely applied not only to *Brachypodium distachyon* and *Arabidopsis* but also monocotyledonous plants, dicotyledonous plants and other plant species.

The new high-velocity chimera gene used in the present invention is not limited to a combination of the gene encoding the motor domain of the myosin XI protein of *Chara* and the gene encoding a neck domain, rod domain and globular tail domain of donor plant 2. Without being limited to the case of the ligation of that combination, other nucleic acids, nucleotides or polynucleotides containing a reporter gene can be inserted between genes encoding each domain. In the present invention, the neck domain and the rod domain can also be produced by using other peptides than those derived from plants including those from animals.

And the transgenic plant, in which the motor domain of the myosin XI protein of the present invention described in detail above has a new high-velocity movement, can be produced by the producing method described in detail below.

Since the growth of the new high-velocity transgenic plant of the present invention is enhanced, increase in the production of plant food such as cereals, vegetables, fruit trees and flavored plants, increase in the production of palatable plants such as tobacco, etc., increase in the production of raw material plants for extraction/isolation of a pharmaceutical compound or raw material thereof such as *Papaver somniferum* (opium poppies) and *Illicium verum* (star anise), etc., increase in production of biomass fuel, and promotion of greening of the national land or forestry, can be provided.

2. Method for Producing Plants with Enhanced Growth Capacity

Another embodiment of the present invention is a method for producing a plant having enhanced growth.

More specifically, another embodiment of the present invention is a method for producing a transgenic plant having enhanced growth capacity of a host plant, the transgenic plant expressing a chimeric protein having:

a peptide containing an amino acid sequence derived from a motor domain of myosin XI of donor plant 1 which is a plant species other than the host plant, and a peptide containing an amino acid sequence of domain derived from a motor domain of myosin XI of donor plant 2 which is a plant species other than the host plant or the host plant, and a loop 2 region of the motor domain having EEPKQGGKGGGKSSFSSIG (SEQ ID NO: 36) or EEPKQGGGKGGSKSSFSSIG (SEQ ID NO: 37), or one in which a plurality of amino acids of these sequences, preferably 1 to 6 amino acids thereof, are deleted, substituted and/or added.

As shown in FIG. 4, the amino acid sequence of the loop 2 region of the myosin XI motor domain of *Chara* used as the donor plant 1 has a high sequence identity with EEPKQGGKGGGKSSFSSIG (SEQ ID NO: 36) and/or EEPKQGGGKGGSKSSFSSIG (SEQ ID NO: 37).

Examples of the method for production of the present invention include a production method in which the motor domain has a peptide encoded by any one of the following nucleic acid sequences (i) to (iii):

(i) the nucleic acid sequence represented by any one of SEQ ID NOs: 13, 15 and 17;

(ii) a nucleic acid sequence having a sequence identity of 80% or more, preferably 85% or more, more preferably 90% or more, most preferably 95% or more with the nucleic acid sequence represented by any one of SEQ ID NOs: 13, 15 and 17; and (iii) a nucleic acid sequence in which a plurality of nucleic acids, preferably 1 to 6 nucleic acids in the nucleic acid sequence represented by any one of SEQ ID NOs: 13, 15 and 17 are deleted, substituted, and/or added.

The nucleic acid sequences represented by SEQ ID NOs: 13, 15 and 17 are nucleic acid sequences encoding the amino acid sequences of SEQ ID NOs: 14, 16 and 18 described in the embodiment of the "transgenic plant", respectively. The nucleic acid sequence of 13 is a nucleic acid sequence that encodes the amino acid sequence (SEQ ID NO: 14) of the myosin XI protein of *Chara: Chara braunii* (hereinafter referred to as "CbM1"). The nucleic acid sequence of SEQ ID NO: 15 is also a nucleic acid sequence encoding the amino acid sequence (SEQ ID NO: 16) of other myosin XI protein of *Chara braunii* (hereinafter referred to as "CbM2"), and the nucleic acid sequence of SEQ ID NO: 17 is one encoding the amino acid sequence (SEQ ID NO: 18) of the myosin XI protein of different species *Chara: Chara australis* (hereinafter referred to as "CaM").

A vector having a nucleic acid sequence encoding the above chimeric protein can be produced by a method well known to those skilled in the art. For example, methods for cloning gene sequences and inserting them into appropriate carriers (such as vectors or plasmids) include those described in, for example, Sambrook et al. (1989) and Experimental Manuals by Gelvin and Stanton (1995), which are techniques well known to those skilled in the art and the methods for cloning gene sequences and inserting them can be carried out according to these well-known methods.

In the production method of the present invention, preferably, a movement velocity of the motor domain alone of above chimeric protein in an in vitro motility assay, in which the chimeric protein binds to actin and moves on the actin, has 4 times or more, preferably 6 times or more, more preferably 8 times or more compared to the velocity of the motor domain alone of the myosin XI protein of the wild-type hos plant in vitro motility assay, or has movement velocity of 6 µm/sec or more, preferably 9 µm/sec or more, more preferably 12 µm/sec or more, at a temperature of 25° C.

In the production method of the present invention, preferably, Vmax of the actin-stimulating ATPase activity of the motor domain is 150 Pi/sec or more, more preferably 200 Pi/sec or more.

The chimeric protein preferably includes a neck domain, rod domain and globular tail domain of the myosin XI protein of the donor plant 2, which is the host plant or a plant species other than the host plant, and includes the motor domain derived from the donor plant 1 for the above motor domain.

In the production method of the present invention, preferably, the donor plant 1 is *Chara* (*Chara braunii* or *Chara australis*).

In the production method of the present invention, preferably, the host plant and/or donor plant 2 is either a monocotyledonous plant or a dicotyledonous plant.

Examples of the monocotyledonous plant that can be used in the production method of the present invention include, but not limited to, *Brachypodium distachyon, Oryza sativa, Triticum aestivum, Triticale, Hordeum vulgare, Avena sativa, Secale cereale, Sorghum bicolor, Panicum miliaceum* (millet), *Saccharum officinarum* and *Zea mays*, etc.

Examples of dicotyledonous plants that can be used in the production method of the present invention include, but are not limited to, *Arabidopsis thaliana, Nicotiana tabacum, Solanum lycopersicum, Solanum tuberosum, Legume, Glycine max, Daucus carota, Manihot esculenta, Medicago sativa* and *Gossypium*, etc.

Hereinafter, a method for obtaining the transgenic plant will be described, regarding a method for constructing a chimeric myosin XI gene, a method for transforming a host plant, a method for obtaining a transgenic plant of monocotyledons, and a dicotyledonous plant for producing the new high-velocity transgenic plant of the present invention.

{1} Construction of Chimeric Myosin XI Gene

The chimera myosin XI gene is a chimeric gene in which the region encoding the motor domain of the myosin XI protein of plants belonging to the genus *Chara* and the region encoding the neck domain, rod domain and globular tail domain of the myosin XI protein of donor plant 2 are linked. A chimeric myosin XI gene, which has respective domains of the myosin XI protein of donor plant 1 and donor plant 2, is prepared by gene recombination technology. This chimeric myosin XI gene construct can be constructed using methods known in the art.

Specifically, first, each myosin XI gene is cloned using the cDNA library of the *Chara* plant and donor plant 2. A cDNA library can be constructed by a known method. For example, the mRNA of each of the *Chara* plant and donor plant 2 is extracted by a known method. Next, a cDNA library is prepared by RT (reverse transcription) reaction using each of the prepared mRNA pools as a template. Techniques known in the art can be used for specific preparation methods, including mRNA extraction and RT reaction conditions, and specific methods of isolating the objective gene. For example, the methods described below can be used: Sambrook J., Molecular Cloning: a Laboratory Manual Second Ed., Cold Spring Harbor Laboratory Press, Cold Spring Harbor, N.Y. (1989). In addition, various commercially available kits for preparing mRNA and cDNA are available. Alternatively, commercially available cDNA libraries for specific types of donor plants etc. can also be used.

Next, the myosin XI gene derived from each plant is isolated from the cDNA library by a nucleic acid amplification method using an appropriate primer set (for example, a PCR method such as reverse PCR, anchor PCR, TAIL-PCR, etc.). As a method in this case, a hybridization method using an appropriate probe (for example, a plaque hybridization method) can be used. When the myosin XI gene is amplified and isolated by the nucleic acid amplification method, the reaction conditions are determined by, for example, carrying out the method of Innis M. et al. Ed., Academic Press, PCR Protocols: A Guide to Methods and Applications (1990). The target myosin XI gene can be designed based on nucleic acid sequence information available from an available database, for example, primers used for nucleic acid amplification methods or probes used for hybridization methods are obtained from NCBI database, RIKEN Plant Science Center database or Kazusa DNA Research Institute DNA sequence analysis information database. In addition, such primers and probes can be designed based on the nucleotide sequences (for example, SEQ ID NO: 35) predicted by the motor domain of the myosin XI protein of Chara represented by amino acid SEQ ID NOs: 14, 16 and 18, further, based on the amino acid sequences of the neck domain and tail domain of myosin XI proteins of monocotyledonous plants such as the myosin XI protein of Brachypodium distachyon represented by amino acid sequence SEQ ID NO: 24, and the amino acid sequences of the myosin XI protein of dicotyledonous plants such as Arabidopsis thaliana represented by amino acid SEQ ID NO: 34. Further, primers and probes can also be prepared by chemical synthesis based on the designed nucleotide sequences.

As for the myosin XI gene of a plant belonging to the genus Chara, if the region encoding the motor domain can be isolated, the downstream region or the full-length gene is not necessarily to be isolated. Similarly, for the myosin XI gene of donor plant 2, it would be sufficient to be capable of isolating the regions encoding the neck domain, rod domain and globular tail domain, and it is not necessarily required to isolate the 5'-terminal region including the region encoding the motor domain.

Next, a chimeric myosin XI gene is constructed using a gene fragment containing the 5'-terminal region of the region encoding the myosin XI gene or myosin XI motor domain of plants belonging to the genus Chara, and a gene fragment containing the 3'-terminal region of the region encoding the myosin XI gene or the regions containing the regions encoding neck domain, rod domain and globular tail domain of donor plant 2. Chimeric myosin XI gene can be constructed by a nucleic acid amplification method using an appropriately designed primer set, and by cloning the gene fragment containing the regions encoding the related domains following linking the regions encoding the related domains so that the function of each domain can be exerted in the objective combination. It is requested to note that each domain is arranged on the nucleotide sequence in the same arrangement as wild type myosin XI. Linkage of the regions encoding each domain is carried out according to enzyme binding by ligase treatment to the binding ends generated by restriction enzymes or single-stranded overhangs, etc., or a nucleic acid amplification method such as PCR. using primers that have a binding sequence (restriction enzyme cleavage site) for enzyme binding, provided that there is no frame shift in the downstream reading frame.

It is desirable to link the motor domain specified by the above-mentioned sequence of a plant belonging to the genus Chara to the IQ motif and rod domain of donor of myosin XI of donor plant 2. A "lever arm α-helix" corresponds to a region consisting of a neck domain and a converter domain.

It has a helical structure starting from a position near the C-terminal of the converter domain contained in the motor domain (see FIG. 1). For example, in the case of CbM1 of Chara braunii, the lever arm α-helix has amino acid residues from 729th to 877th. In this case, the converter domain has amino acid residues from 729th to 741st, and the neck domain has amino acid residues from 743rd to 883rd. In the case of Arabidopsis thaliana myosin XI-2, the lever arm α-helix has amino acid residues from 722nd to 870th. In this case, the converter domain has amino acid residues from 722nd to 735th, and the neck domain has amino acid residues from 736th to 876th. Specifically, it is preferable to link the position immediately after the C-terminal of the converter domain of myosin XI of plants belonging to the genus Chara to the N-terminal of the IQ motif located on the most N-terminal side of the neck domain of the donor plant 2. This is because the motor domain derived from the myosin XI of a plant belonging to the genus Chara is required to contain the entire converter region of the motor domain of the Chara myosin (Seki M. et al, J Mol. Biol. 2004, 344: 311-315). In order for the myosin light chain of donor plant 2 to bond to the IQ motif, the complete IQ motif of donor plant 2 is required.

In the chimeric myosin XI protein made according to the above principle as described in the mentioned-below examples, the region up to the 741st position of Myosin XI: CbM1 of Chara (Chara braunii) is linked at the 759th position of the Brachypodium distachyon (Brachypo Phytozozme Brachypodium distachyon v3.1: Bradi2g41977.1). This sequence corresponds to the downstream region from the position 742nd amino acid residue and the myosin XI protein of CbM1.

In addition, in the case where the donor plant 2 is, for example, Arabidopsis thaliana, the region up to the 741st position of the amino acid sequence of SEQ ID NO: 14 of Myosin XI: CbM1 of Chara braunii is bonded to the sequence number of Arabidopsis MYA2 (GenBank: BAA98070.1) at 735th position of the amino acid sequence of SEQ ID NO: 34. This sequence corresponds to the 742nd amino acid residue and its downstream region of the myosin XI protein of CbM1.

(2) Production of Vector

The chimeric myosin XI gene constructed by the method described above can be inserted into an expression vector and expressed in a host plant as necessary. "Expression vector" refers to a nucleic acid expression system capable of transporting a gene or the like contained therein to a target plant cell and expressing the gene under appropriate conditions. Specifically, a plasmid expression vector using a plasmid, a virus expression vector using a virus, etc. can be exemplified.

Examples of plasmid expression vectors that can be used include pBI, pPZP, pSMA, pUC, pBR, pBluescript (Stratagene) and pTriEXTM (TaKaRa), and pBI and pRI binary vectors.

In the case of viral expression vectors, cauliflower mosaic virus (CaMV), golden mosaic virus (BGMV), tobacco mosaic virus (TMV), etc., can be used.

The expression vector can contain a promoter, terminator, enhancer, poly A addition signal, 5'-UTR (untranslated region) sequence, marker or selection marker gene, multicloning site, origin of replication, etc. The kind of each component will not be specifically limited if the function can be exhibited within a plant cell. Components known in the art can be appropriately selected according to the plant into which the expression vector is introduced or the purpose of the component in the plant (for example, expression pattern).

As the promoter, in addition to the promoter of the endogenous myosin XI gene of the host plant or donor plant 2, an overexpression promoter, a constitutive promoter, a site-specific promoter, a time-specific promoter and/or an inducible promoter can be used. And the promoter depends on the desired expression pattern. Examples of overexpressing promoters include cauliflower mosaic virus (CaMV)-derived 35S promoter, Ti plasmid-derived nopaline synthase gene promoter (Pnos), corn-derived ubiquitin promoter, rice-derived actin promoter, tobacco-derived PR protein promoter, etc. can be exemplified. In addition, ribulose diphosphate carboxylase small subunit (Rubisco ssu) promoter or histone promoter can also be used. Furthermore, examples of the site-specific promoter include promoters that induce root-specific expression described in JP2007-77677A publication.

As described above, the enhanced growth capacity may be an improvement in the growth of the whole plant or an enhancement of the growth of a part of the plant.

While terminators include nopaline synthase (NOS) gene terminator, octopine synthase (OCS) gene terminator, CaMV 35S terminator, E. coli lipopolyprotein (lpp) 3'terminator, trp operon terminator, amyB terminator, ADH1 gene terminator, etc., it will not be specifically limited, as long as it has the sequence which terminates transcription of the gene transcribed by the said promoter. In addition, an intrinsic terminator of the endogenous myosin XI gene of the host plant or donor plant 2 may be used.

Examples of enhancers that can be used include an enhancer region containing an upstream sequence of the CaMV 35S promoter and a CMV enhancer, in addition to an enhancer specific to the endogenous myosin XI gene of the host plant or donor plant 2. The enhancer is not particularly limited as long as it can increase the expression efficiency of the chimeric myosin XI protein.

Examples of selection marker genes include, for example, genes of drug resistance genes (e.g., tetracycline resistance gene, ampicillin resistance gene, kanamycin resistance gene, hygromycin resistance gene, spectinomycin resistance gene, chloramphenicol resistance gene, and luciferase, β-galactosidase, β-glucuronidase (GUS) and green fluorescent protein (GFP)), and enzymes such as neomycin phosphotransferase II (NPT II) and dihydrofolate reductase. A marker or selection marker gene can be inserted into an expression vector including chimeric myosin XI or another expression vector. In the latter case, an effect equivalent to that obtained with a single expression vector to which the above genes are linked can be obtained by simultaneously introducing each expression vector into the target plant.

As a method for inserting the chimeric myosin XI gene into an expression vector at a specific site, methods known in the field can be used. One example of such a method is described in Sambrook J. Molecular Cloning: a Laboratory Manual Second Ed., Cold Spring Harbor Laboratory Press, Cold Spring Harbor (1989), and the insertion can be performed according to this method. According to this method, in the case of a PCR product having a 3'-A protruding end, which is usually obtained using Taq DNA polymerase, the corresponding restriction enzyme site or multicloning site or 5'-T protruding end is appropriately used, and it is inserted into an appropriate expression vector and ligated. Alternatively, when commercially available systems or kits are used, they can be prepared using methods specific to those systems or kits. For example, a gateway system (Invitrogen (registered trademark)) can be used.

(3) Transformation Method

As a method for transforming a host plant, a method known in this technical field can be used. In general, transformation can be performed by introducing a chimeric myosin XI gene or a plasmid expression vector or a viral expression vector containing the gene into a host plant cell.

When transforming a host plant using a chimeric myosin XI gene or a plasmid expression vector containing such gene, a protoplast method, a particle gun method, an *Agrobacterium* method, or the like can be used.

The protoplast method is a method in which a cell wall of a host plant cell is removed by an enzyme treatment such as cellulase to obtain a protoplast, and a known chimeric myosin XI gene is introduced into the protoplast. Moreover, it can also be carried out by using techniques, such as an electroporation method, a microinjection method, and a polyethylene glycol method. The electroporation method includes introducing a gene into the protoplast by applying an electric pulse to a mixture of the protoplast and the target gene. The microinjection method includes directly introducing a target gene into a protoplast using a microneedle under a microscope. The polyethylene glycol method is a method for introducing a target gene into protoplasts by the action of polyethylene glycol.

The particle gun method is a method in which a target gene (in the case of the present invention, chimeric myosin XI gene) is attached to fine particles such as gold and tungsten, and the particles are shot into plant tissue cells at a high rate. The gene of target can thus be introduced into cells. Thereby, a transformant in which the target gene has been incorporated into the genomic DNA of the host cell can be obtained. In general, transformed cells can be screened based on the presence of the marker gene product.

The *Agrobacterium* method uses a bacterium belonging to the genus *Agrobacterium* (for example, *A. tumefaciens* or *A. rhizogenes*) as a transforming factor, and uses the derived Ti plasmid to introduce the target gene into the host plant cell.

Any of the above transformation methods are known in this technical field. Specific examples of these methods are described in, for example, Bechtold et al., CR Acad. Sci. Paris, Life Sci. 1993, and can be performed according to this method.

Furthermore, when a viral expression vector containing a chimeric myosin XI gene (for example, CaMV, BGMV, or TMV described above) is used, the chimeric myosin XI gene can be introduced into a host plant cell by infecting the plant cell together with the viral vector. Specifically, for example, a plant virus genome is inserted into a cloning vector such as a vector derived from *Escherichia coli* to produce a recombinant, and the chimeric myosin XI gene is then inserted into the virus genome of this recombinant. Thereafter, the target gene can be introduced into the plant cell by excising a recombinant of the plant virus genome region by using a restriction enzyme and infecting the target plant cell with the obtained virus genome. Details of gene transfer methods using such viral vectors are described in Hohn et al., Molecular Biology of Plant Tumors (Academic Press, New York) 1982, p 549, U.S. Pat. No. 4,407,956, etc.

In addition, the host plant transformed by the above method may be a wild strain or a mutant strain. When the host plant is a mutant strain, preferred is a knockout plant in which the myosin XI gene of the same type as the tail domain derived from the donor plant 2 of the chimeric myosin XI gene has been deleted. For example, when the tail domain of the chimeric myosin XI gene introduced into the host plant is derived from the myosin XI-1 gene of donor plant 2, the host plant is preferably a myosin XI-1 deficient mutant plant.

(4) Plant Regeneration Method

The method for regenerating a plant having an enhanced growth from the transformed host plant cell can be performed based on a known method for regenerating a transgenic plant from the transformed plant cell.

One example of such a method is an in vitro regeneration method for regenerating plants from transformed plant cells through the formation of callus which is an undifferentiated growth cell. Such method is known in this technical field. Specific examples of this method include the methods described in Bechtold et al., C.R. Acad. Sci. Paris, Life Sci., 1993, etc.

It is also possible to use an in planta method in which a nucleic acid expression system is directly introduced into cells of a target plant individual without carrying out callus and cell culture steps. Plant hormones such as auxin, gibberellin and/or cytokinin can be used to promote the growth and/or division of transformed cells.

(5) The Case where the Host Plant is a Monocotyledonous Plant

Regarding the case where the host plant is a monocotyledonous plant, the case where the transformed plant is produced will be explained by using, as an example, *Brachypodium distachyon* which is an experimental model of monocotyledonous plant.

When the host plant is *Brachypodium distachyon*, the neck domain, rod domain and globular tail domain of the chimeric myosin XI protein can be used, which are derived from, for example, the myosin XI-B protein (*Brachypodium distachyon*: Bradi2g41977.1) represented by SEQ ID NO: 20. In this case, the neck domain has the 734th to 873rd amino acid residues of the amino acid sequence of SEQ ID NO: 20, and the rod domain has the 874th to 912nd and 971st to 1053rd amino acid residues of the amino acid sequence shown in SEQ ID NO: 20. The globular tail domain has the 1054th to 1501st residues of the amino acid sequence of SEQ ID NO: 20.

A vector containing a chimera gene encoding a chimera myosin XI protein in which the motor domain of the myosin XI protein of *Chara* and the neck domain, rod domain and globular tail domain of the myosin XI protein of the above-mentioned *Brachypodium distachyon* were linked, was prepared according to methods well known to those skilled in the art, such as cloning from cDNA and ligation. For example, using *Agrobacterium*, the chimeric protein is introduced into callus of *Brachypodium distachyon* by a method well known to those skilled in the art, and after culture, the callus is transplanted to soil or water, and cultivated to obtain a transformed *Brachypodium distachyon*.

In the case of producing a transgenic plant using a monocotyledon other than *Brachypodium distachyon* as a host plant, a transformed monocotyledon can be obtained by using the similar method to the case of *Brachypodium distachyon*.

(6) The Case where the Host Plant is a Dicotyledonous Plant

Next, regarding the case where the host plant is a dicotyledonous plant, the case where the transgenic plant is produced will be explained below using the experimental model, *Arabidopsis thaliana*, as an example.

The neck domain, rod domain, and globular tail domain of the chimeric myosin XI protein can be used, which are derived from, for example, *Arabidopsis* myosin XI-2 protein (GenBank: BAA98070.1) shown in SEQ ID NO: 34. In this case, the neck domain has the 734th to 872nd amino acid residues of the amino acid sequence of SEQ ID NO: 34, and the rod domain has the 873rd to 946th and 968th to 1048th amino acid residues of the amino acid sequence of SEQ ID NO: 34. And the globular tail domain has the 1049th to 1520th amino acid residues in the amino acid sequence of SEQ ID NO: 34.

A vector containing a chimeric gene encoding a chimeric myosin XI protein in which the motor domain of the myosin XI protein of the *Chara* and the neck domain, rod domain and globular tail domain of the myosin XI protein of the above-mentioned *Arabidopsis thaliana* were linked, was prepared according to methods well known to those skilled in the art, such as cloning and ligation from the cDNA of the *Chara* and the *Arabidopsis thaliana*. For example, using *Agrobacterium*, *Arabidopsis thaliana* was introduced by the floral dipping method, and transformed transgenic plants were selected based on resistance to antibiotics such as hygromycin. Then, by cultivating the plant after transplantation into soil or water, an *Arabidopsis* transformant with enhanced growth can be obtained.

In the case where a transgenic plant is produced using a dicotyledon other than *Arabidopsis* as a host plant, a transformed dicotyledon can be obtained by using the similar method to the case of the above *Arabidopsis*.

A transgenic plant obtained by the above method is a first-generation transgenic plant, which is a plant with enhanced growth capacity, and is the object of the present invention. In the present description, the term "first-generation transgenic plant" also includes a clone of a first-generation transgenic plant having the genetic information identical thereto. For example, a plant obtained via cutting, grafting, or layering of a portion of a plant obtained from the first-generation transgenic plant, a plant regenerated after cell culture and through callus formation, and a new autotroph generated from a vegetative propagation organ (e.g., a rhizome, tuberous nut, corm, or runner) obtained through asexual reproduction from a first-generation transgenic plant fall under the first-generation transgenic plant.

Since the transgenic plant produced by the above production method has enhanced growth, increase in the production of plant food such as cereals, vegetables, fruit trees and flavored plants, increase in the production of palatable plants such as tobacco, etc., increase in the production of material plants for extraction/isolation of a pharmaceutical compound or raw material thereof such as *Papaver somniferum* (opium poppies) and *Illicium verum* (star anise), etc., increase in production of biomass fuel, and promotion of greening of the national land or forestry, can be provided.

3. Passage Plants from a Transgenic Plant with Enhanced Growth Capacity

Another embodiment of the present invention is a passage plant from a transgenic plant. That is, a passage plant from the transgenic plant is a progeny of the transformed plant having an enhanced growth capacity, and is a progeny that maintains the characters with the enhanced growth capacity.

In the present description, "a passage plant from a transformed plant with enhanced growth capacity" means a progeny obtained by regenerating by crossing a first-generation transgenic plant carrying the chimeric myosin XI gene obtained by the production method of the first embodiment, and the gene can be expressed in the passaged plant. One example is the seedling of a first-generation transgenic plant.

The progeny of the growth promoting plant of the present invention can be obtained by a known method. For example, a plant with enhanced growth, which is a first-generation transgenic plant, can be obtained as a seed for obtaining a first-generation progeny seed and a second-generation transgenic plant. As an example of the method of obtaining the second-generation progeny from the first-generation progeny of the present invention, the seeds are rooted in a suitable medium, the seedlings are transplanted into a pot containing soil, then it can be obtained by using the second-generation progeny and culturing under appropriate culture conditions. Production of the progeny obtained in this embodiment is not limited, provided that that the chimeric myosin XI gene described in the first embodiment is retained in the progeny. Accordingly, by repeating the similar method to the method of obtaining the second-generation progeny, the third-generation and later progeny can be obtained.

Since the passage plant from the transgenic plant with enhanced growth capacity of the present invention has enhanced growth, increase in the production of plant food such as cereals, vegetables, fruit trees and flavored plants, increase in the production of palatable plants such as tobacco, etc., increase in the production of material plants for extraction/isolation of a pharmaceutical compound or raw material thereof such as *Papaver somniferum* and *Illicium verum*, etc., increase in production of biomass fuel, and promotion of greening of the national land or forestry, can be provided.

4. Method for Promoting Plant Growth

Another embodiment of the present invention relates to a method for promoting the growth of a target plant by introducing a chimeric myosin XI gene into the plant. The method of this embodiment is substantially the same as the "method for producing plants with enhanced growth capacity" of the second embodiment.

All documents mentioned in the present description are incorporated herein by reference in their entirety. The examples described herein are exemplifications of embodiments of the invention and should not be construed as limiting the scope of the invention.

Example 1

Cloning of New High-Velocity Type Myosin XI Gene of *Chara*

Materials and Methods

Cloning of two new high-velocity myosin XI (CbM1, CbM2) motor domain genes of *Chara* (*Chara braunii*), was performed utilizing the *Chara* gene database (not publicly available) constructed by Associate Professor Hidetoshi Sakayama, Graduate School of Science, Kobe University, according to a conventional method.

In addition, a motor domain gene of one new high-velocity myosin XI (CaM5049) of Australian *Chara* (*Chara australis*) was identified following creating a phylogenetic tree of *Chara* myosin XI and Australian *Chara* myosin XI by utilizing the database of the Australian *Chara* gene, which was constructed by the associate professor.

PCR

The total RNA prepared from *Chara* (*Chara braunii*) which was provided by Associate Professor Hidetoshi Sakayama, Graduate School of Science, Kobe University, was used. By using the total RNA as a template, single-stranded cDNA was prepared by utilizing PrimeScriptTMII Reverse Transcriptase (TaKaRa) according to the manufacturer's protocol. Next, the gene of the motor domain of each myosin was amplified by RT-PCR using the single-stranded cDNA prepared above. For CbM1, the combination of the below-mentioned forward primer (SEQ ID NO: 1) and reverse primer (SEQ ID NO: 2) was used under the reaction conditions including; for 10 seconds at 98° C., for 2 minutes and 12 seconds at 68° C., and at 72° C. in 35 cycles. By using the amplified PCR product, the below-mentioned forward primer (SEQ ID NO: 3) and reverse primer (SEQ ID NO: 4) were used in combination under the reaction conditions including; for 10 seconds at 98° C., for 2 minutes and 12 seconds at 68° C. in 35 cycles.

For CbM2, by using the combination of the following forward primer (SEQ ID NO: 5) and reverse primer (SEQ ID NO: 6), PCR was carried out under the reaction conditions including; for 10 seconds at 98° C., for 2 minutes and 12 seconds at 68° C., and at 72° C. in 35 cycles. By using the amplified PCR product, and by use of the combination of the below-mentioned forward primer (SEQ ID NO: 7) and reverse primer (SEQ ID NO: 8), PCR was carried out under the conditions including: for 10 seconds at 98° C., for 2 minutes and 12 seconds at 68° C. in 35 cycles.

For each of CbM1 and CbM2, PCR products were treated with SpeI (New England Biolabs) and KpnI (New England Biolabs), and inserted into SpeI and KpnI fragments of Litmus28 (New England Biolabs) with Ligation high Ver.2 (TOYOBO).

Subcloning into a Vector with a Flag Sequence

By using, as a template, Litmus28 in which each myosin gene has been inserted, PCR was carried out under the reaction conditions including; CbM1 is in the combination of the below-mentioned forward primer (SEQ ID NO: 9) and reverse primer (SEQ ID NO: 10), and CbM2 is in the combination of the below-mentioned forward primer (SEQ ID NO: 11) and reverse primer (SEQ ID NO: 12), for 10 seconds, at 98° C., for 30 seconds at 60° C., and for 2 minutes and 12 seconds at 68° C. in 35 cycles. The PCR product was inserted into pFastBac-Flag (Ito, PNAS, 2009, 106 (51): 21585-21590) by In-Fusion (TaKaRa).

Results

The two new high-velocity myosin XI (CbM1 and CbM2) motor domain genes of the cloned *Chara* (*Chara braunii*) had the nucleic acid sequence of SEQ ID NO: 13 encoding the amino acid sequence of SEQ ID NO: 14, and the nucleic acid sequence of SEQ ID NO: 15 encoding the amino acid sequence of SEQ ID NO: 16.

In addition, the motor domain of the new high-velocity myosin XI gene (CaM) of Australian *Chara* (*Chara australis*) identified by phylogenetic tree has the nucleic acid sequence of SEQ ID NO: 17 and the amino acid sequence of SEQ ID NO: 18.

As well, FIG. 1 shows a schematic diagram of the structure of myosin.

Example 2

Construction of Chimeric Myosin XI Gene

By combining the nucleic acid sequence coding for the 1st to 741st amino acid residues of CbM1 of myosin XI of *Chara braunii* and the nucleotide sequence coding for the 759th to 1529th amino acid residues of myosin XI-B of *Brachypodium distachyon*, there was prepared a chimeric myosin XI with the myosin XI-B motor domain of *Brachypodium distachyon* being changed to myosin XI motor domain of *Chara braunii*. SEQ ID NO: 19 shows the nucleic acid sequence of Myosin XI-B (Bradi2g41977.1) of *Brachypodium distachyon*, and SEQ ID NO: 20 shows its amino acid sequence. SEQ ID NO: 21 shows the nucleic acid sequence of the prepared chimeric myosin XI, and SEQ ID NO: 22 shows its amino acid sequence.

Example 3

Materials and Methods

In Vitro Motility Assay

The neck domain of myosin XI has 6 IQ motifs per heavy chain molecule, and 6 light chains bind to each heavy chain of myosin XI (FIG. 1). In order for myosin XI to move, the binding of the light chain to the heavy chain is indispensable. Thus, since the light chain as well as the heavy chain of myosin XI is essential for measuring the velocity of movement of myosin XI in an in vitro motility assay, the myosin whose velocity can be measured in an in vitro motility assay is limited to those with a known light chain (Ito et al., Biochem. Biophys. Res. Commun., 2003, 312: 958-964). The light chain of Myosin XI of *Brachypodium distachyon* is unknown. Accordingly, the velocity of movement of chimeric myosin consisting of the motor domain of the myosin XI of *Chara* and the neck and tail domains of the myosin XI-B of *Brachypodium distachyon* cannot be measured by an in vitro motility assay. Since myosin moves by bending of the lever arm, the movement velocity of myosin correlates with the length of the lever arm (Spudich, J. A., Nature 1994, 372: 515-518). Chimeric myosin with 6 IQ motifs in the neck domain has a lever arm several times longer than the length of the motor domain alone, so it is known that the velocity of movement of the chimeric myosin is about 4 times the motor domain alone (Ito et al., J. Biol. Chem., 2007, 282: 19534-19545). Therefore, the movement velocity of chimeric myosin was calculated by measuring the movement velocity of the motor domain alone by an in vitro motility assay and multiplying that velocity by 4 times.

By a known method using a baculovirus insect cell system, expression was performed by adding a Flag sequence and a MYC sequence to the motor domains of *Chara* myosin CbM1 and CbM2, and purification was then performed using an anti-FLAG M2 affinity resin (Sigma-Aldrich). As controls, the myosin gene represented by nucleic acid SEQ ID NO: 23 encoding the motor domain (amino acid SEQ ID NO: 24) of myosin XI-B protein (Bradi2g41977.1) of *Brachypodium distachyon*; and the myosin gene, represented by nucleic acid SEQ ID NO: 25, encoding the motor domain (amino acid SEQ ID NO: 26) of the myosin XI-2 (MYA2) of *Arabidopsis thaliana*, and the myosin gene represented by nucleic acid SEQ ID NO: 27 encoding the motor domain (amino acid SEQ ID NO: 28) of the myosin XI protein (CcM) of *Chara corallina*; were used.

The movement velocity of each myosin XI motor domain was determined by an in vitro motor assay using an anti-c-myc monoclonal antibody (Zymed Laboratories Inc.; Cat. No. 13-2500). The details are based on the document (Ito, PNAS, 2009, 106 (51), 21585-21590). First, a slide glass and a cover slip were coated with 0.1% nitrocellulose dissolved in pentyl acetate (WAKO). Next, a flow cell was prepared by placing a spacer made by cutting an untreated cover slip on a slide glass and placing a coated cover slip thereon. Silicone grease (HIGH VACUUME, Dow Corning Asia) was used for adhesion between the cover glass and the slide glass. An anti-human c-myc antibody (diluted in 0.2 mg/ml in PBS, pH 7.5) was poured into the prepared flow cell in an amount of 1 volume and allowed to stand at room temperature for 30 minutes. Next, BSA solution (1 mg/ml BSA, 30 mM HEPES-KOH pH 7.4, 150 mM NaCl, 0.04% NaN3) was used to prevent non-specific adsorption of myosin on the glass surface with no c-myc antibody adsorbing thereto. Six times the volume of the BSA solution was poured and allowed to stand at room temperature for 30 minutes, and the glass surface with no antibody adsorbing thereto was blocked with BSA. After 30 minutes, three times the volume of a wash buffer (150 mM KCl, 4 mM MgCl2, 1 mM EGTA, 25 mM HEPES-KOH, pH 7.4, 3 mM ATP, 1 mM DTT) was flowed to wash away BSA not adsorbing to the glass surface. Thereafter, 1.5 times the volume of the myosin solution was poured into the flow cell whose glass surface had been blocked at a concentration that binds to all c-myc antibodies, and allowed to stand at room temperature for 15 minutes. Thereafter, in order to wash away myosin not adsorbing to the antibody, three times the volume of the wash buffer was again poured. Then, the flow cell was washed again with a washing buffer, and Rh-ph-actin (F-actin fluorescently labeled with Rhodamine-phalloidin) solution (0.33 μg/ml Rh-ph-actin, 150 mM KCl, 4 mM MgCl2, 1 mM EGTA, 25 mM HEPES-KOH, pH 7.4, 1 mM DTT) in 1.5 times the volume was poured. Finally, three times the volume of the solution containing ATP (150 mM KCl, 4 mM MgCl2, 1 mM EGTA, 25 mM HEPES-KOH, pH 7.4, 3 mM ATP, 10 mM DTT, 10 mM glucose) was poured. And the movement of Rh-ph-actin was observed with a fluorescence microscope, and recording on video was performed with CCD camera with an image intensifier (DII-2050 CanonFD-M52) attached.

In addition, the movement velocity was calculated based on the average sliding speed of each myosin molecule by measuring the movement of actin filaments that move smoothly over a distance of 10 μm or more. As a control, the *Arabidopsis thaliana* myosin XI-2 motor domain and the *Chara* (*Chara corallina*) myosin XI motor domain were used.

The conceptual diagram of this in vitro motility assay is shown in FIG. 2, and the results are shown in Table 1.

ATPase Activity

The evaluation of actin activated ATP hydrolysis activity was performed according to Ito et al., Biochem. Biophys. Res. Commun., 2003, 312: 958-964. The concentration of inorganic phosphate produced per second by hydrolysis of ATP by myosin at various actin concentrations was measured by malachite green. After reacting myosin with various concentrations of actin filaments, the reaction was stopped with perchloric acid solution. The solution was mixed with an equivalent volume of malachite green solution [0.7 M hydrochloric acid, 0.2% disodium molybdate (VI) dihydrate (WAKO), 0.03% malachite green oxalate (CHROMA-GESELLSCHAFT), 0.05% Triton X-100], and allowed to stand for 25 minutes in a water bath at 30° C. to develop color. By using a spectrophotometer, the absorbance of the colored solution at a wavelength of 650 nm was measured. From the change, the change in the phosphorylation concentration of the reaction solution was calculated, and the actin-activated ATP hydrolysis activity of myosin was measured. The ATP hydrolysis reaction at various actin concentrations was measured, and the Vmax of the actin activated ATP hydrolysis reaction was determined by the Michaelis-Menten equation.

Results

In Vitro Motility Assay

The movement velocity of the new high-velocity myosin XI of *Chara braunii* myosin XI (CbM1) motor domain was 14.5 μm/sec, and the movement velocity of the myosin XI (CbM2) motor domain was 13.2 μm/sec. These were found to be about 3 times faster than the movement velocity (4.8 μm/sec) of the motor domain of the myosin XI of the control high-velocity myosin XI of *Chara corallina*. In addition, it was found that the movement velocity was about 8 times faster than that of *Arabidopsis thaliana* myosin XI-2 and that of *Brachypodium distachyon* myosin XI-B (Table 1).

TABLE 1

| Motor Domain of Myosin Used | Velocity of Motor Domain (μm/sec) | Velocity of Chimeric Myosin (μm/sec) | ATP Hydrolysis Activity of Motor Domain (Vmax, Pi/sec) |
|---|---|---|---|
| *Arabidopsis Thaliana* myosin XI-2 (wild type) | 1.8 | — | 60 |
| *Brachypodium distachyon* myosin XI-B (wild type) | 1.8 | — | 142 |
| *Chara corallina* myosin XI (high-veleocity type) | 4.8 | 19 | 580 |
| *Chara braunii* myosin XI, g50407, CbM1 (new high-velocity type) | 14.5 | 58 | 405 |
| *Chara braunii* myosin XI, g48390, CbM2 | 13.2 | 53 | 199 |

ATPase Activity

From Table 1, it was elucidated that ATPase activity has a positive correlation (in an increasing trend) with the increase in the velocity of myosin.

Example 4

Myosin Phylogenetic Tree

Using ClustalX 2.1, a molecular phylogenetic tree was created for the myosin motor domains represented by SEQ ID NOs: 14, 16, 18, 24, 28-33. The results are shown in FIG. 3.

Structural Analysis of Myosin

Alignment analysis was performed using ClustalX 2.1 for the loop 2 regions of the myosin motor domains represented by SEQ ID NOs: 14, 16, 18, 24, and 28-33. The results are shown in FIG. 4.

Results

Phylogenetic Tree

From FIG. 3, it was elucidated that the gene of myosin XI (CbM1, CbM2) cloned from *Chara* (*Chara braunii*) and myosin XI gene (CaM5049) present in the *Chara* (*Chara australis*) belong to an independent group different from other myosin XI genes of *Arabidopsis thaliana*, *Chara corallina*, and any other of the genus *Chara*.

Structural Analysis of Myosin

From FIG. 4, by the studies, myosin XI (3 types) cloned from *Chara* (*Chara braunii*) and *Chara* (*Chara australis*) have loop 2 region of EEPKQGGKGGGKSSFSSIG (SEQ ID NO: 36) or EEPKQGGGKGGSKSSFSSIG (SEQ ID NO: 37), or the amino acid sequences in which a plurality of amino acids of the sequences thereof, preferably 1 to 6 amino acids, are deleted, substituted and/or added.

Example 5

Verification of Transgenic Plant Phenotype (1)

The phenotype of the model of monocotyledonous plant, *Brachypodium distachyon*, transformed with the chimeric myosin XI gene constructed in EXAMPLE 2 was verified. As controls, *Brachypodium distachyon* (wild type) and *Brachypodium distachyon* into which only the vector (mock) was introduced were used.

Plant Transformation

The chimeric XI gene constructed in EXAMPLE 2 was introduced into callus derived from an immature embryo of wild-type *Brachypodium distachyon* using *Agrobacterium*, and the transformed transgenic plant was selected based on the resistance to hygromycin. The above method was based on Alves, Nature protocols, 2009, 4 (5), 638-649.

Cultivation of Transgenic Plants

To examine the growth state, the first-generation T1 seeds were independently seeded in a selection medium (1 bag of Murashige and Skoog Plant Salt Mixture (Wako), 0.1 μg/ml of thiamine hydrochloride, 0.5 μg/ml of pyridoxine hydrochloride, 0.5 μg/ml of nicotinic acid, 2 μg/ml of glycine, 100 μg/ml of myo-inositol, 3% sucrose, 40 μg/ml of hygromycin, 0.2% gellan gum) prepared in a culture dish, and then placed at 4° C. for 3 to 5 days. After low temperature treatment, the plants were cultivated at 22° C. for 3 to 5 days, 16 hours of light/day.

Next, in order to examine the elongation of the stem, the number of leaves, and the number of spikelets, each plant was transplanted to soil (Pro-mix BX Mycorise) and cultivated at 22° C. for about 80 days, 20 hours of light/day.

Although selection was performed with hygromycin at the time of T0 callus selection, T1 was not subjected to hygromycin selection in consideration of growth inhibition by hygromycin, and the transgenic plant was confirmed by real-time PCR.

Results

Figure 5:
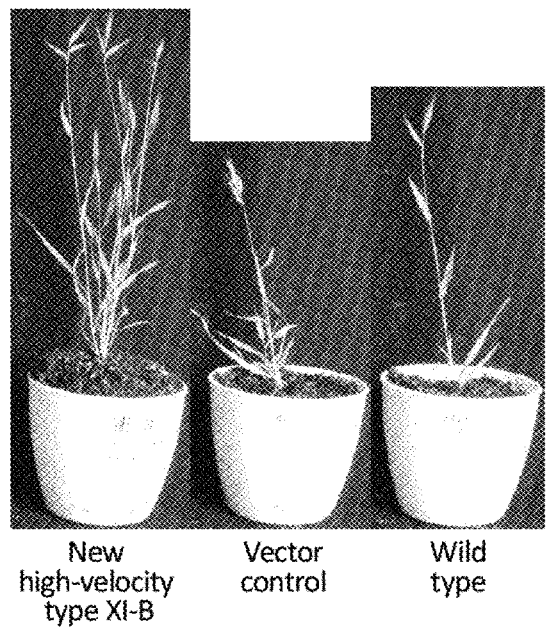
FIG. 5 represents the photographs compared to: a new high-velocity type *Brachypodium distachyon* (T1) transformed by introducing with a vector so as to express a chimeric protein combined with a new high-velocity type myosin XI protein of *Chara braunii* and the domains other than the motor domain of myosin XI of *Brachypodium distachyon*; a wild type *Brachypodium distachyon*, and *Brachypodium distachyon* introduced only the vector as control groups.
Figure 6:
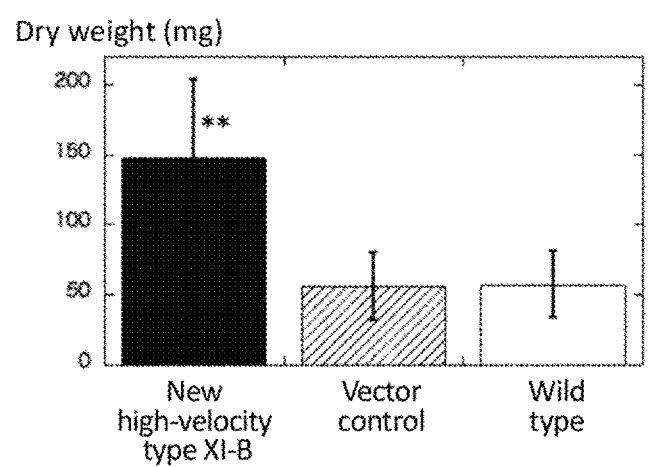
FIG. 6 represents the results of a comparison of the dry weights of; *Brachypodium distachyon* plants introduced with a new high-velocity *Brachypodium distachyon* myosin XI-B gene; and as control groups, wild type *Brachypodium distachyon* plants, and *Brachypodium distachyon* plants introduced with a vector only (measured using plants after the end of growth (70 days after potting). Each group is: new high-velocity *Brachypodium distachyon* plants, N=16; wild-type *Brachypodium distachyon* plants, N=7; *Brachypodium distachyon* plants introduced with vector only, N=10). ** represents p<0.01 in t-test.
Figure 7A:
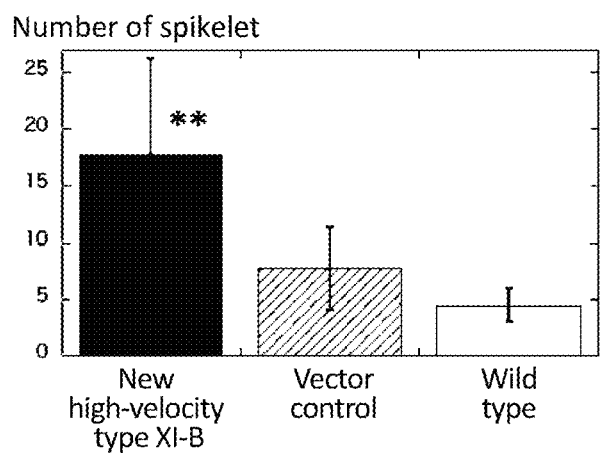
FIG. 7A represents the result of comparing the number of spikelets of: *Brachypodium distachyon* plants introduced with a new high-velocity *Brachypodium distachyon* myosin XI-B gene; and as control groups, a wild type *Brachypodium distachyon* plants and *Brachypodium distachyon* plants introduced with a vector only (measured using plants after the end of growth (70 days after potting). Each group is: new high-velocity *Brachypodium distachyon* plants, N=16; a wild-type *Brachypodium distachyon* plants, N=7; *Brachypodium distachyon* plants introduced with vector only, N=10). ** represents p<0.01 in t-test.
Figure 7B:
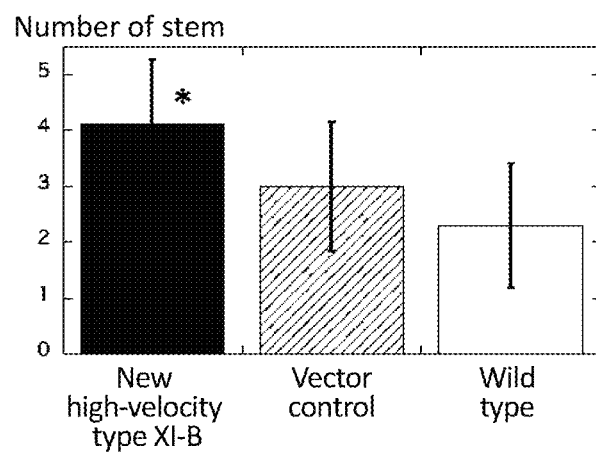
FIG. 7B represents the result of comparing the number of stems of: *Brachypodium distachyon* plants introduced with a new high-velocity *Brachypodium distachyon* myosin XI-B gene; and as control groups, a wild type *Brachypodium distachyon* plants and *Brachypodium distachyon* plants introduced with a vector only (measured using plants after the end of growth (70 days after potting). Each group is: new high-velocity *Brachypodium distachyon* plants, N=16; a wild-type *Brachypodium distachyon* plants, N=7; *Brachypodium distachyon* plants introduced with vector only, N=10). ** represents p<0.01 in t-test.
Figure 7C:
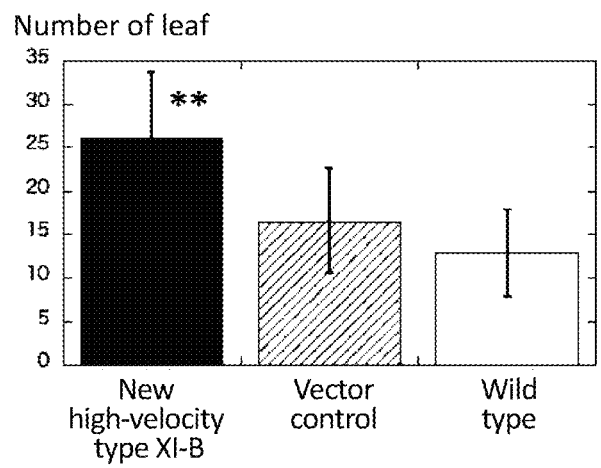
FIG. 7C represents the result of comparing the number of leaves of: *Brachypodium distachyon* plants introduced with a new high-velocity *Brachypodium distachyon* myosin XI-B gene; and as control groups, a wild type *Brachypodium distachyon* plants and *Brachypodium distachyon* plants introduced with a vector only (measured using plants after the end of growth (70 days after potting). Each group is: new high-velocity *Brachypodium distachyon* plants, N=16; wild-type *Brachypodium distachyon* plants, N=7; *Brachypodium distachyon* plants introduced with vector only, N=10). ** represents p<0.01 in t-test.

FIG. 5 shows a photograph of the T1 plant into which the chimeric myosin XI gene was introduced. FIG. 6 is a graph comparing the dry weight after the growth of the plant (T1) introduced with the chimeric myosin XI gene, to the dry weight of the wild-type plant and that of the plant introduced with only the vector gene. The dry weight was remarkably increased compared to the wild-type plants and the plants into which only vector genes had been introduced. FIGS. 7A to 7C are the graphs showing the number of spikelets, the number of stems, and the number of leaves after the growth of the plant (T1) into which the chimeric myosin XI gene was introduced, as compared to the number of spikelets, the number of stems, and the number of leaves of the wild type plants and the plants introduced with only vector. In the chimeric myosin XI gene-introduced plant, an increase in the number of spikelets, the number of stems, and the number of leaves were observed, and the increase in the number of spikelets and the number of leaves were particularly remarkable. As described above, it was shown that growth was promoted in the plant (T1) into which the chimeric myosin XI gene was introduced, as compared to the wild type plant and the plant into which only the vector was introduced. In addition, since growth was promoted and enlarged in monocotyledonous plants, it was suggested that growth could be promoted and enlarged in dicotyledonous plants as well as monocotyledonous plants. The results of sequence analysis revealed that the new high-velocity type has a common sequence in the loop 2 region. It was shown that this loop 2 region contributed to growth promotion and enlargement of plants.

Example 6

Verification of the Phenotype of Transgenic Plants (2)

The phenotype of *Arabidopsis thaliana*, a model of a dicotyledonous plant, transformed with the constructed chimeric myosin gene, was verified. As a control, *Arabidopsis thaliana* (wild type) was used.

Construction of Chimeric Myosin XI Gene

Similarly to EXAMPLE 2, a chimeric myosin was prepared, in which the motor domain of myosin of *Arabidopsis thaliana* was changed to the motor domain of myosin XI of *Chara braunii*, by combining the nucleic acid sequence encoding the 1st to 741st amino acid residues of CbM1 of myosin XI of *Chara braunii* and the nucleotide sequence encoding the 735th to 1505th amino acid residues of *Arabidopsis thaliana* myosin. SEQ ID NO: 38 shows the nucleic acid sequence of *Arabidopsis thaliana* myosin, and SEQ ID NO: 39 shows the amino acid sequence. SEQ ID NO: 40 shows the nucleic acid sequence of the produced chimeric myosin, and SEQ ID NO: 41 shows its amino acid sequence.

Plant Transformation

The constructed chimeric gene was introduced into an xi-2 knockout strain of *Arabidopsis thaliana* by using *Agrobacterium*, and the transformed transgenic plant was selected based on hygromycin resistance. The above method was based on "KAJOHITASHIHOU (the inflorescence dipping method)", "MODERUSHOKUBUTSU NO JIKKENPUROTOKORU (model plant experiment protocol revision)" revised 3rd edition, 149-154".

Cultivation of Transgenic Plants

To examine the growth state, the obtained T1 seeds of the first-generation were independently seeded in a selective medium (1 bag of Murashige and Skoog Plant Salt Mixture (Wako), 0.1 µg/ml of thiamine hydrochloride, 0.5 µg/ml of pyridoxine hydrochloride, 0.5 µg/ml of nicotinic acid, 2 µg/ml of glycine, 100 µg/ml of myo-inositol, 3% of sucrose, 40 µg/ml of hygromycin, 0.2% of gellan gum) prepared in a culture dish, and then placed at 4° C. for 3 to 5 days. Thereafter, homozygous third-generation T3 seeds were obtained, and after low-temperature treatment, they were cultivated at 25° C. for 24 days, 16 hours of light/day.

Evaluation of Transgenic Plants

A photograph of a plant derived from T3 seeds on the 24th day of growth was taken from directly above. The entire rosette leaf was circumscribed using the circular tool of the analysis software Image J (NIH) (see FIG. 9), and the area of the rosette leaf circumscribed was quantified using the analysis function (Measure) of Image J (in pixels). After that, the diameter was calculated by converting to the actual area from the area per pixel of the scale bar.

Results

Figure 8:
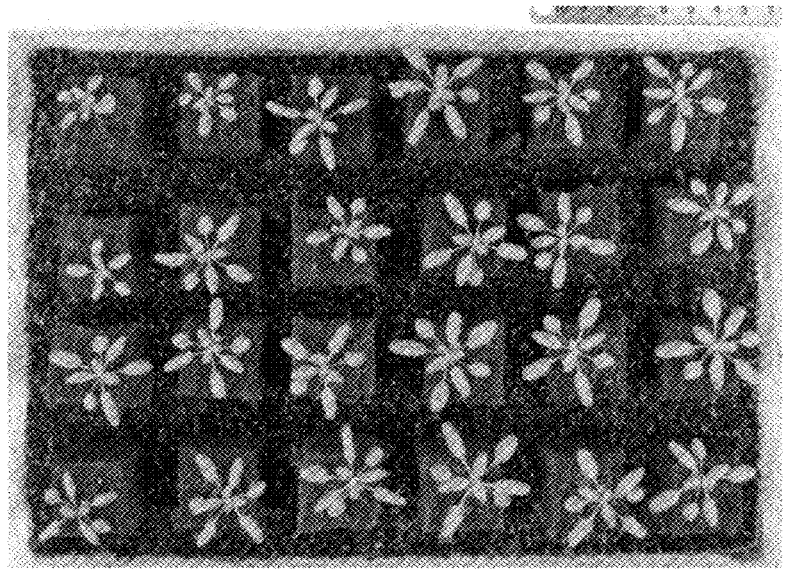
FIG. 8 is a photograph representing the phenotypes of wild-type *Arabidopsis thaliana* plants and *Arabidopsis thaliana* plants introduced with a new high-velocity *Arabidopsis* XI-2.
Figure 9:
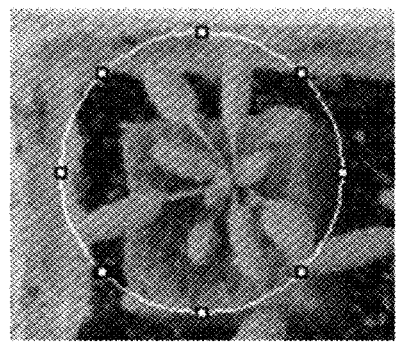
FIG. 9 represents an image of condition obtained by photographing a plant body derived from T3 on the 24th day of growth, from directly above, the entire rosette leaf is encircled with a circular tool of the analysis software Image J (NIH), and the area of rosette leaf (pixel unit) is quantified.
Figure 10:
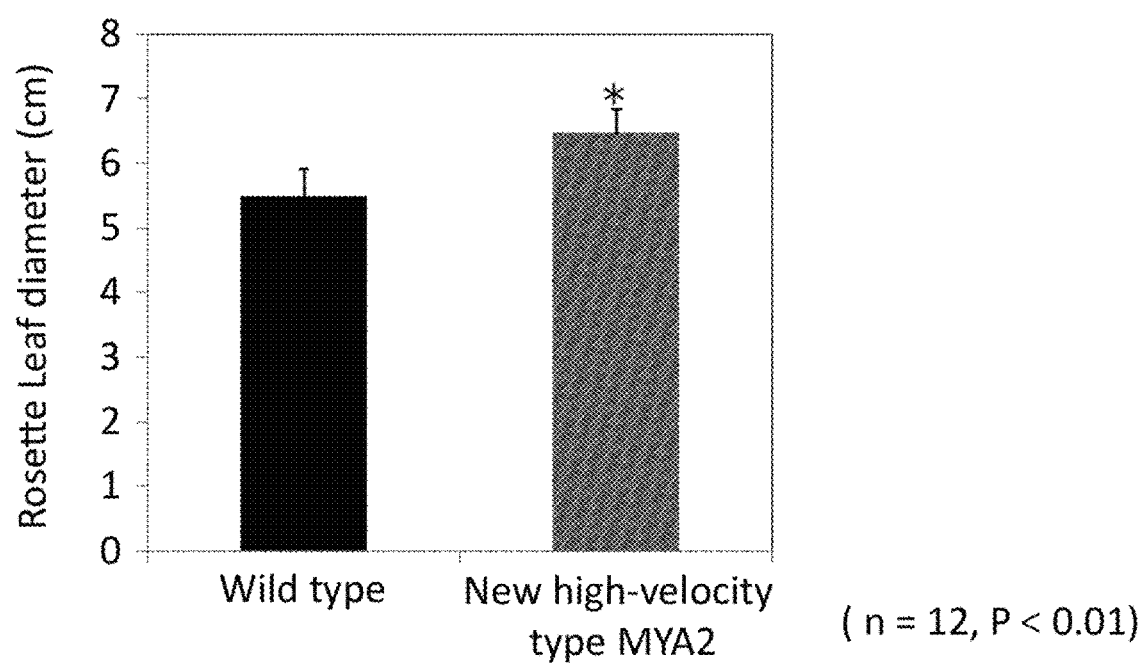
FIG. 10 is a graph representing the result of calculating the diameters of rosette leaves by quantifying the area (pixel unit) of the rosette leaves. ** represents p<0.01 in t-test.

FIG. 8 shows the phenotypes of wild-type *Arabidopsis thaliana* and transgenic *Arabidopsis thaliana*. FIG. 9 shows the aspect of quantifying the area (pixel unit) of rosette leaves by circumscribing the whole rosette leaves with a circular tool of analysis software Image J (NIH) from an image obtained by taking a photograph of a plant derived from T3 seeds on the 24th day of growth. FIG. 10 shows the result of calculating the rosette leaf diameter by quantifying the area (pixel unit) of the rosette leaf. From the results of FIGS. 8 and 10, transgenic *Arabidopsis thaliana* (T3) was larger than wild-type *Arabidopsis thaliana*, and the aboveground part increased by about 20%. It was shown that the chimeric myosin of the present invention could promote and enlarge the growth of the dicotyledonous plant as well as the monocotyledonous plant.

Since the growth of the new high-speed transgenic plant of the present invention is enhanced, increase in the production of plant food such as cereals, vegetables, fruit trees and flavored plants, increase in the production of palatable plants such as tobacco, etc., increase in the production of material plants for extraction/isolation of a pharmaceutical compound or raw material thereof such as *Papaver somniferum* (opium poppies) and *Illicium verum* (star anise), etc., increase in production of biomass fuel, and promotion of greening of the national land or forestry, can be provided.

What is claimed is:

1. A transgenic plant with an enhanced growth as compared to a host plant, the transgenic plant comprising a gene encoding a chimeric protein comprising:
   a first peptide comprising an amino acid sequence of a plant 1 motor domain, the plant 1 motor domain being a motor domain of a myosin XI protein of a donor plant 1 which is a plant species other than the host plant; and
   a second peptide comprising an amino acid sequence of a plant 2 domain, the plant 2 domain comprising a neck domain, a rod region, and a globular tail domain of a myosin XI protein of a donor plant 2 or a host plant,
   wherein the plant 1 motor domain has a peptide having any one of the following amino acid sequences (i) to (iii):
   (i) the amino acid sequence represented by any one of SEQ ID NOs: 14, 16 and 18;
   (ii) an amino acid sequence having 85% or more identity with the amino acid sequence represented by any one of SEQ ID NOs: 14, 16 and 18; and
   (iii) an amino acid sequence in which 1 to 6 amino acids in the amino acid sequence represented by any one of SEQ ID NOs: 14, 16 and 18 are deleted, substituted, and/or added,
   wherein the loop 2 region of the plant 1 motor domain has the amino acid sequence: EEPKQGGKGGGKSSFS-SIG (SEQ ID NO: 36) or EEPKQGGGKGGSKSSFS-SIG (SEQ ID NO: 37),
   wherein the velocity of movement of the plant 1 motor domain alone in an in vitro motility assay, in which the plant 1 motor domain binds to and moves on actin, is 4 times or more compared to the velocity of movement of a motor domain alone of a myosin XI protein of host plant that does not comprise a gene encoding said chimeric protein in an in vitro motility assay.

2. The transgenic plant according to claim 1, wherein Vmax of the actin-activating ATPase activity of the plant 1 motor domain is 150 Pi/sec or more.

3. The transgenic plant according to claim 1, wherein the donor plant 1 for the motor domain of the myosin XI protein is a *Chara* selected from *Chara braunii* or *Chara australis*.

4. The transgenic plant according to claim 1, wherein the host plant and/or the donor plant 2 is either a monocotyledonous plant or a dicotyledonous plant.

5. The transgenic plant according to claim 4, wherein the monocotyledonous plant is one species selected from the group consisting of *Brachypodium distachyon, Oryza sativa, Triticum aestivum, Triticale, Hordeum vulgare, Avena sativa, Secale cereale, Sorghum bicolor, Panicum miliaceum, Saccharum officinarum* and *Zea mays*.

6. The transgenic plant according to claim 4, wherein the dicotyledonous plant is one species selected from the group consisting of *Arabidopsis thaliana, Nicotiana tabacum, Solanum lycopersicum, Solanum tuberosum, Legume, Glycine max, Daucus carota, Manihot esculenta, Medicago sativa* and *Gossypium*.

7. The transgenic plant according to claim 1, wherein the velocity of movement of the plant 1 motor domain alone of the chimeric protein in an in vitro motility assay, in which the plant 1 motor domain binds to and moves on actin, is 6 μm/sec or more.

* * * * *

SEQUENCE LISTING

```
<160> NUMBER OF SEQ ID NOS: 61

<210> SEQ ID NO 1
<211> LENGTH: 21
<212> TYPE: DNA
<213> ORGANISM: Artificial Sequence
<220> FEATURE:
<223> OTHER INFORMATION: CbM1 forward primer

<400> SEQUENCE: 1
tagcgtctct tcaaaatggc a                                                 21

<210> SEQ ID NO 2
<211> LENGTH: 23
<212> TYPE: DNA
<213> ORGANISM: Artificial Sequence
<220> FEATURE:
<223> OTHER INFORMATION: CbM1 reverse primer

<400> SEQUENCE: 2
cgcactctcc ttgtcatctt ctt                                               23

<210> SEQ ID NO 3
<211> LENGTH: 28
<212> TYPE: DNA
<213> ORGANISM: Artificial Sequence
<220> FEATURE:
<223> OTHER INFORMATION: CbM1 forward primer

<400> SEQUENCE: 3
aaaactagta tggcaacgtt tggagtcg                                          28
```

<210> SEQ ID NO 4
<211> LENGTH: 30
<212> TYPE: DNA
<213> ORGANISM: Artificial Sequence
<220> FEATURE:
<223> OTHER INFORMATION: CbM1 reverse primer

<400> SEQUENCE: 4
tttggtaccg gctgcctcat tgagaatctc                                    30

<210> SEQ ID NO 5
<211> LENGTH: 25
<212> TYPE: DNA
<213> ORGANISM: Artificial Sequence
<220> FEATURE:
<223> OTHER INFORMATION: CbM2 forward primer

<400> SEQUENCE: 5
tatttatagt tcagaatggc ggagc                                         25

<210> SEQ ID NO 6
<211> LENGTH: 18
<212> TYPE: DNA
<213> ORGANISM: Artificial Sequence
<220> FEATURE:
<223> OTHER INFORMATION: CbM2 reverse primer

<400> SEQUENCE: 6
cctgcggcca attctttt                                                 18

<210> SEQ ID NO 7
<211> LENGTH: 25
<212> TYPE: DNA
<213> ORGANISM: Artificial Sequence
<220> FEATURE:
<223> OTHER INFORMATION: CbM2 forward primer

<400> SEQUENCE: 7
aaaactagta tggcggagca ggttg                                         25

<210> SEQ ID NO 8
<211> LENGTH: 24
<212> TYPE: DNA
<213> ORGANISM: Artificial Sequence
<220> FEATURE:
<223> OTHER INFORMATION: CbM2 reverse primer

<400> SEQUENCE: 8
tttggtaccg gctgccgcat tcag                                          24

<210> SEQ ID NO 9
<211> LENGTH: 30
<212> TYPE: DNA
<213> ORGANISM: Artificial Sequence
<220> FEATURE:
<223> OTHER INFORMATION: CbM1 forward primer

<400> SEQUENCE: 9
gacaaacgat ccatggcaac gtttggagtc                                    30

<210> SEQ ID NO 10
<211> LENGTH: 35
<212> TYPE: DNA
<213> ORGANISM: Artificial Sequence
<220> FEATURE:
<223> OTHER INFORMATION: CbM1 reverse primer -continued
<210> SEQ ID NO 11
<211> LENGTH: 28
<212> TYPE: DNA
<213> ORGANISM: Artificial Sequence
<220> FEATURE:
<223> OTHER INFORMATION: CbM2 forward primer

<400> SEQUENCE: 11
gacaaacgat ccatggcgga gcaggttg                                          28

<210> SEQ ID NO 12
<211> LENGTH: 30
<212> TYPE: DNA
<213> ORGANISM: Artificial Sequence
<220> FEATURE:
<223> OTHER INFORMATION: CbM2 reverse primer

<400> SEQUENCE: 12
gctcgccgcc accggtggct gccgcattca                                        30

<210> SEQ ID NO 13
<211> LENGTH: 2235
<212> TYPE: DNA
<213> ORGANISM: Chara braunii
<220> FEATURE:
<221> NAME/KEY: misc_feature
<223> OTHER INFORMATION: CbM1(CbMg50407) motor domain

<400> SEQUENCE: 13
atggcaacgt ttggagtcgg ttccccagtg tgggttgaag atgaagagga tatgtggatt        60
gaggcaacgg tgctcaagat cgaggcagat aaggtcattt cgaagaacag gaaaggtggc       120
gaggttgttt cgtctaagga tatggtccat ccgagagacg aggacacggc tgaaatgggt       180
gttgacgaca tgacgaggtt gtcgtacctc cacgagcctg agtattgga caatctttcc        240 cgaagatacc acctcaatca aatttataca tacacaggga gcatttgtat cgccatcaat       300
cctttccaag cagtgccaca tttggttgga accaaactca tggaaatgtt caaggttgca       360
cagcctggag aggtcagcca acctcacgtg tatgcagtgg ctgacagagc ttacaaggct       420
atgatggatg aggaaaagag tcagtcaatt cttgtcagtg gagaaagtgg tgcgggtaag       480
acagaagcga caaagcttat catgaactac cttgccttta tgggagggag ggccactccc       540
gttgcaggag aaagatcagt ggagcagaag gtgttggagt caaatccact gctggaagcc       600
ttcggaaatg caaagacagt ccgtaacaac aattccagtc gcttcggtaa attcgtggag       660
atccagttca acagaggcaa gatttctggg gctgcagttc gaacctatct gctggagcga       720
tctcgtatca ctcaagtgtc gacacctgag cgtagttacc attgtttcta ccagctatgt       780
gcgggagcca cagcagagga gagagaaaag ctgaagatcg aagctgctcc aaactacttc       840
tacctcaatc agagcgagtg ttttgaggtt cctcgatttg atgaagtaga agagtacaag       900
gcaactcgac atgccatgga tgttgtgggt atctccactg aggagcagga tggtattttc       960
cgaatcgttg catcaattct tcatcttgga aatgttgact tcaaaccagg caaggaggca      1020
gactcctcac aacttgcaga tgacaagtcc cgatttcacc tcaactgctg tgcggagttg      1080
ctgggagcga acccaaagct tctgaagat tcactcatcc aaagaatcat ggttacgagg       1140
ggagaagcca tcaccaagct actggacaag aaacaggctg ttggaagtcg tgatgctctc      1200

```
gcaaaaactc tctatgccaa gatgttcgac tggttggtcg acaaggtcaa caagtccatt   1260
ggtcaagatc ccaactccaa cactctggtt ggtgtgcttg atatttatgg ctttgagagc   1320
ttcacggtga acagtttcga gcagctttgc atcaatctca caaatgaaaa gctgcagcag   1380
cacttcaaca cgcatgtctt caagatggag caagaggagt acgtgaagga agagatcaac   1440
tgggacaaca ttgactttgt tgataacata gatgttctgg accttatcga agaaaaccca   1500
ttgggaatca ttgctttgct cgatgaagcc tgcatgttgc ccaaatccac accggagtca   1560
tttggccaaa agcttgctca gtcttttgac aagcacaaac gatttacaaa gcacaagttc   1620
aagaagacac tgttcaaaat tgaccacttt gcaggagagg tggagtactc gacggacaca   1680
tttattgaaa agaacaagga tttcgtgatt gcggagcatc agcaactgct gacagcgtcc   1740
acagatccat ttgtgagaca ggtgtatccg ccaccagagg agccaaagca gggcggaaag   1800
ggtggaggga agtcatcctt ctcctctatt ggaactcgtt tcaagcaaca actgcaatct   1860
ctgatggaca cccttaacca gacagagccg cattatgtcc gttgcgtgaa gcccaaccag   1920
aaactgaagc cactcatgtt cgagaagcgg attgtcctcc agcagcttcg gtgcagtggt   1980
gtgttggaag ctgtgcgtat cagttgtgct ggtttcccaa caaggcgtac attcttcgag   2040
tttgcagaca gattcaagat tttgtttccc gatgcagttg ccaactgtgg ccaggactat   2100
aagagcgcat gtgtcaagat cctggagaag attgggctcg agaggtatca gattggaaaa   2160
accaaggtgt ttttgcgagc aggccagatg gctattctgg atacaaaacg taccgagatt   2220
ctcaatgagg cagcc                                                    2235
```

```
<210> SEQ ID NO 14
<211> LENGTH: 745
<212> TYPE: PRT
<213> ORGANISM: Chara braunii
<220> FEATURE:
<221> NAME/KEY: MISC_FEATURE
<223> OTHER INFORMATION: CbM1(CbMg50407) motor domain

<400> SEQUENCE: 14
```

Met Ala Thr Phe Gly Val Gly Ser Pro Val Trp Val Glu Asp Glu Glu
1               5                   10                  15

Asp Met Trp Ile Glu Ala Thr Val Leu Lys Ile Glu Ala Asp Lys Val
                20                  25                  30

Ile Ser Lys Asn Arg Lys Gly Gly Glu Val Val Ser Ser Lys Asp Met
            35                  40                  45

Val His Pro Arg Asp Glu Asp Thr Ala Glu Met Gly Val Asp Asp Met
        50                  55                  60

Thr Arg Leu Ser Tyr Leu His Glu Pro Gly Val Leu Asp Asn Leu Ser
65                  70                  75                  80

Arg Arg Tyr His Leu Asn Gln Ile Tyr Thr Tyr Thr Gly Ser Ile Cys
                85                  90                  95

Ile Ala Ile Asn Pro Phe Gln Ala Val Pro His Leu Val Gly Thr Lys
            100                 105                 110

Leu Met Glu Met Phe Lys Val Ala Gln Pro Gly Glu Val Ser Gln Pro
        115                 120                 125

His Val Tyr Ala Val Ala Asp Arg Ala Tyr Lys Ala Met Met Asp Glu
    130                 135                 140

Glu Lys Ser Gln Ser Ile Leu Val Ser Gly Glu Ser Gly Ala Gly Lys
145                 150                 155                 160

Thr Glu Ala Thr Lys Leu Ile Met Asn Tyr Leu Ala Phe Met Gly Gly

-continued

```
                165                 170                 175
Arg Ala Thr Pro Val Ala Gly Glu Arg Ser Val Glu Gln Lys Val Leu
            180                 185                 190

Glu Ser Asn Pro Leu Leu Glu Ala Phe Gly Asn Ala Lys Thr Val Arg
        195                 200                 205

Asn Asn Asn Ser Ser Arg Phe Gly Lys Phe Val Glu Ile Gln Phe Asn
    210                 215                 220

Arg Gly Lys Ile Ser Gly Ala Ala Val Arg Thr Tyr Leu Leu Glu Arg
225                 230                 235                 240

Ser Arg Ile Thr Gln Val Ser Thr Pro Glu Arg Ser Tyr His Cys Phe
                245                 250                 255

Tyr Gln Leu Cys Ala Gly Ala Thr Ala Glu Glu Arg Glu Lys Leu Lys
            260                 265                 270

Ile Glu Ala Ala Pro Asn Tyr Phe Tyr Leu Asn Gln Ser Glu Cys Phe
        275                 280                 285

Glu Val Pro Arg Phe Asp Glu Val Glu Glu Tyr Lys Ala Thr Arg His
    290                 295                 300

Ala Met Asp Val Val Gly Ile Ser Thr Glu Glu Gln Asp Gly Ile Phe
305                 310                 315                 320

Arg Ile Val Ala Ser Ile Leu His Leu Gly Asn Val Asp Phe Lys Pro
                325                 330                 335

Gly Lys Glu Ala Asp Ser Ser Gln Leu Ala Asp Asp Lys Ser Arg Phe
            340                 345                 350

His Leu Asn Cys Cys Ala Glu Leu Leu Gly Ala Asn Pro Lys Leu Leu
        355                 360                 365

Glu Asp Ser Leu Ile Gln Arg Ile Met Val Thr Arg Gly Glu Ala Ile
    370                 375                 380

Thr Lys Leu Leu Asp Lys Lys Gln Ala Val Gly Ser Arg Asp Ala Leu
385                 390                 395                 400

Ala Lys Thr Leu Tyr Ala Lys Met Phe Asp Trp Leu Val Asp Lys Val
                405                 410                 415

Asn Lys Ser Ile Gly Gln Asp Pro Asn Ser Asn Thr Leu Val Gly Val
            420                 425                 430

Leu Asp Ile Tyr Gly Phe Glu Ser Phe Thr Val Asn Ser Phe Glu Gln
        435                 440                 445

Leu Cys Ile Asn Leu Thr Asn Glu Lys Leu Gln Gln His Phe Asn Thr
    450                 455                 460

His Val Phe Lys Met Glu Gln Glu Glu Tyr Val Lys Glu Glu Ile Asn
465                 470                 475                 480

Trp Asp Asn Ile Asp Phe Val Asp Asn Ile Asp Val Leu Asp Leu Ile
                485                 490                 495

Glu Lys Lys Pro Leu Gly Ile Ile Ala Leu Leu Asp Glu Ala Cys Met
            500                 505                 510

Leu Pro Lys Ser Thr Pro Glu Ser Phe Gly Gln Lys Leu Ala Gln Ser
        515                 520                 525

Phe Asp Lys His Lys Arg Phe Thr Lys His Lys Phe Lys Lys Thr Leu
    530                 535                 540

Phe Lys Ile Asp His Phe Ala Gly Glu Val Glu Tyr Ser Thr Asp Thr
545                 550                 555                 560

Phe Ile Glu Lys Asn Lys Asp Phe Val Ile Ala Glu His Gln Gln Leu
                565                 570                 575

Leu Thr Ala Ser Thr Asp Pro Phe Val Arg Gln Val Tyr Pro Pro Pro
            580                 585                 590
```

Glu Pro Lys Gln Gly Gly Lys Gly Gly Lys Ser Ser Phe Ser
    595                 600                 605

Ser Ile Gly Thr Arg Phe Lys Gln Gln Leu Gln Ser Leu Met Asp Thr
    610                 615                 620

Leu Asn Gln Thr Glu Pro His Tyr Val Arg Cys Val Lys Pro Asn Gln
625                 630                 635                 640

Lys Leu Lys Pro Leu Met Phe Glu Lys Arg Ile Val Leu Gln Gln Leu
                645                 650                 655

Arg Cys Ser Gly Val Leu Glu Ala Val Arg Ile Ser Cys Ala Gly Phe
            660                 665                 670

Pro Thr Arg Arg Thr Phe Phe Glu Phe Ala Asp Arg Phe Lys Ile Leu
        675                 680                 685

Phe Pro Asp Ala Val Ala Asn Cys Gly Gln Asp Tyr Lys Ser Ala Cys
    690                 695                 700

Val Lys Ile Leu Glu Lys Ile Gly Leu Glu Arg Tyr Gln Ile Gly Lys
705                 710                 715                 720

Thr Lys Val Phe Leu Arg Ala Gly Gln Met Ala Ile Leu Asp Thr Lys
                725                 730                 735

Arg Thr Glu Ile Leu Asn Glu Ala Ala
            740                 745

<210> SEQ ID NO 15
<211> LENGTH: 2253
<212> TYPE: DNA
<213> ORGANISM: Chara braunii
<220> FEATURE:
<221> NAME/KEY: misc_feature
<223> OTHER INFORMATION: CbM2(CbMg48390) motor domain

<400> SEQUENCE: 15

```
atggcggagc aggttgcaat tgggtcccca gtgtgggtgg aggatgcaga agacatgtgg      60
attgaggccg ttgtcatgaa aatcgaggcc aagaaaatta cgagcaagaa catcaagggg     120
accatcgtcg agtcttcccc cgaaatggtg catcctcgag acgaagacac gaagccgttg     180
ggagtggaag acatgacccg ttgtcctac ctccatgagc ccggggtgtt agataatctt      240
ctccgtcgat acatggaaaa agagatctac acctacactg gaacatttg tatcgcaatc     300
aacccgtttc aggctgtgcc gcacttggtc ggcactcagc tgatggagat tttcaagaac     360
tctcagccgg gcgaggtcac acagcctcat gtctatgcag tggctgacag ggcctacaaa     420
gcgatgctgg acgaggggca aagccagtcg attttggtga gcggggaaag tggagccgga     480
aaaacggagg cgacgaagct gatcatgaac tacctggcct tatgggcgg acgctctggt      540
ggtgctgctt ccagcggcgg agtgagaact gtggagcaga aggtgttgga gtcgaaccca     600
ctgcttgaag ctttcggaaa tgcgaagaca gtgcgtaaca ataactcgag tcgcttcggc     660
aagtttgtcg aaattcagtt taacgggacg aagatctcgg gagcggctgt gaggacgtac     720
ctgctggaga gatcgagagt gacccaggtt tccactccgg agaggagtta ccactgtttc     780
tatcagctct gcgcaggggc atcggaagag gatagggcaa aatgaagat aggaaaggca     840
tcagactacc attacctgaa ccagagcgag tgttttgaag tgccgcgtat cgacgacaag     900
gaagagtaca gcatcacacg aaacgccatg gacgtcgttg ggataagtga ggaggagcag     960
gacggcattt tccgaatcgt ggcagccatt cttcatctgg gtaacatcga gttcgcgcct    1020
gggaaggatg cggactcgtc gaagattgcg gacgagaaat ctcgatatca ccttgaagcc    1080
tgtgcagaac tgctggcgtg tgatcccaat cttctggagt actcgttgat ccaaagggtc    1140
```

```
atgatgactg gcacagaaaa aatcaagaaa cttctgaaca aaactgcagc attgggtagc    1200
agggatgctc ttgcaaagac actgtacgcc aagatgtttg actggttggt gcaaaaagtg    1260
aacgtgtcta tagggcagga tgcgacctct acgacgctgg tcggcgtctt ggacatctac    1320
ggctttgaga gcttcaaggt gaacagtttc gagcagctct gcatcaacct gacgaacgag    1380
aaacttcagc agcacttcaa caatcacgtg ttcaagatgg agcagcagga atacataagg    1440
gaagagatca actggagcaa catcgatttt gtggacaaca ttgacgtgct ggatctgatc    1500
gagaagaaac cggtggggat catcgcgctg cttgacgaag catgcatgtt gccgaaatcg    1560
acgccggagt cttttgcggc gaagttgtac ggctcgtttg acaagcacaa gcgcttcgga    1620
aagcataaat tcaagaagac gctgttcagg atcgaccatt ttgcaggcga ggtggagtac    1680
tccacggaga cgttcatcga aaagaacaag gactttgtca tcactgagca tcaggagctg    1740
ctgatgaact ccaaagatcc atttatcagg gatgtgtatc cccctcctcc ggaggagcca    1800
aagcaggggg gcgaaagggc cggctcgaag tcgtctttct cttcgattgg gacccgcttc    1860
aagcaacaac tccaatcgtt gatggaaacg ttgaacgcga cagagccgca ttacgtgcgt    1920
tgcgtaaagc cgaaccagtt gctgaagcct ctgaacttcg acaagaggat tgttcttcag    1980
caattgcggt gcagcggcgt catggaggct gtgagaatca gctgtgcggg cttcccaacg    2040
cggcgtacgt tcttcgagtt ccaagaccgt ttcaaggttc tctatccgga cgtggtggcc    2100
cagtgcggag aggactacag gctggcatgc gtgaaggttc tggagcgaac aggcctcgaa    2160
gattatcaga ttggcaagac gaaagtgttc cttcgggctg ccagatggc caccttgat     2220 gcaagacgac agaccattct gaatgcggca gcc                                2253
```

<210> SEQ ID NO 16
<211> LENGTH: 751
<212> TYPE: PRT
<213> ORGANISM: Chara braunii
<220> FEATURE:
<221> NAME/KEY: MISC_FEATURE
<223> OTHER INFORMATION: CbM2(CbMg48390) motor domain

<400> SEQUENCE: 16

```
Met Ala Glu Gln Val Ala Ile Gly Ser Pro Val Trp Val Glu Asp Ala
1               5                   10                  15

Glu Asp Met Trp Ile Glu Ala Val Met Lys Ile Glu Ala Lys Lys
            20                  25                  30

Ile Thr Ser Lys Asn Ile Lys Gly Thr Ile Val Glu Ser Ser Pro Glu
        35                  40                  45

Met Val His Pro Arg Asp Glu Asp Thr Lys Pro Leu Gly Val Glu Asp
    50                  55                  60

Met Thr Arg Leu Ser Tyr Leu His Glu Pro Gly Val Leu Asp Asn Leu
65                  70                  75                  80

Leu Arg Arg Tyr Met Glu Lys Glu Ile Tyr Thr Tyr Thr Gly Asn Ile
                85                  90                  95

Cys Ile Ala Ile Asn Pro Phe Gln Ala Val Pro His Leu Val Gly Thr
            100                 105                 110

Gln Leu Met Glu Ile Phe Lys Asn Ser Gln Pro Gly Glu Val Thr Gln
        115                 120                 125

Pro His Val Tyr Ala Val Ala Asp Arg Ala Tyr Lys Ala Met Leu Asp
    130                 135                 140

Glu Gly Gln Ser Gln Ser Ile Leu Val Ser Gly Glu Ser Gly Ala Gly
145                 150                 155                 160
```

```
Lys Thr Glu Ala Thr Lys Leu Ile Met Asn Tyr Leu Ala Phe Met Gly
                165                 170                 175
Gly Arg Ser Gly Gly Ala Ala Ser Ser Gly Gly Val Arg Thr Val Glu
            180                 185                 190
Gln Lys Val Leu Glu Ser Asn Pro Leu Leu Glu Ala Phe Gly Asn Ala
        195                 200                 205
Lys Thr Val Arg Asn Asn Ser Ser Arg Phe Gly Lys Phe Val Glu
    210                 215                 220
Ile Gln Phe Asn Gly Thr Lys Ile Ser Gly Ala Ala Val Arg Thr Tyr
225                 230                 235                 240
Leu Leu Glu Arg Ser Arg Val Thr Gln Val Ser Thr Pro Glu Arg Ser
                245                 250                 255
Tyr His Cys Phe Tyr Gln Leu Cys Ala Gly Ala Ser Glu Glu Asp Arg
            260                 265                 270
Ala Lys Met Lys Ile Gly Lys Ala Ser Asp Tyr His Tyr Leu Asn Gln
        275                 280                 285
Ser Glu Cys Phe Glu Val Pro Arg Ile Asp Asp Lys Glu Glu Tyr Ser
    290                 295                 300
Ile Thr Arg Asn Ala Met Asp Val Val Gly Ile Ser Glu Glu Glu Gln
305                 310                 315                 320
Asp Gly Ile Phe Arg Ile Val Ala Ala Ile Leu His Leu Gly Asn Ile
                325                 330                 335
Glu Phe Ala Pro Gly Lys Asp Ala Asp Ser Ser Lys Ile Ala Asp Glu
            340                 345                 350
Lys Ser Arg Tyr His Leu Glu Ala Cys Ala Glu Leu Leu Ala Cys Asp
        355                 360                 365
Pro Asn Leu Leu Glu Tyr Ser Leu Ile Gln Arg Val Met Met Thr Gly
    370                 375                 380
Thr Glu Lys Ile Lys Lys Leu Leu Asn Lys Thr Ala Ala Leu Gly Ser
385                 390                 395                 400
Arg Asp Ala Leu Ala Lys Thr Leu Tyr Ala Lys Met Phe Asp Trp Leu
                405                 410                 415
Val Gln Lys Val Asn Val Ser Ile Gly Gln Asp Ala Thr Ser Thr Thr
            420                 425                 430
Leu Val Gly Val Leu Asp Ile Tyr Gly Phe Glu Ser Phe Lys Val Asn
        435                 440                 445
Ser Phe Glu Gln Leu Cys Ile Asn Leu Thr Asn Glu Lys Leu Gln Gln
    450                 455                 460
His Phe Asn Asn His Val Phe Lys Met Glu Gln Gln Glu Tyr Ile Arg
465                 470                 475                 480
Glu Glu Ile Asn Trp Ser Asn Ile Asp Phe Val Asp Asn Ile Asp Val
                485                 490                 495
Leu Asp Leu Ile Glu Lys Lys Pro Val Gly Ile Ala Leu Leu Asp
            500                 505                 510
Glu Ala Cys Met Leu Pro Lys Ser Thr Pro Glu Ser Phe Ala Ala Lys
        515                 520                 525
Leu Tyr Gly Ser Phe Asp Lys His Lys Arg Phe Gly Lys His Lys Phe
    530                 535                 540
Lys Lys Thr Leu Phe Arg Ile Asp His Phe Ala Gly Glu Val Glu Tyr
545                 550                 555                 560
Ser Thr Glu Thr Phe Ile Glu Lys Asn Lys Asp Phe Val Ile Thr Glu
                565                 570                 575
```

```
His Gln Glu Leu Leu Met Asn Ser Lys Asp Pro Phe Ile Arg Asp Val
            580                 585                 590

Tyr Pro Pro Pro Glu Glu Pro Lys Gln Gly Gly Lys Gly Gly
        595                 600                 605

Ser Lys Ser Ser Phe Ser Ser Ile Gly Thr Arg Phe Lys Gln Gln Leu
    610                 615                 620

Gln Ser Leu Met Glu Thr Leu Asn Ala Thr Glu Pro His Tyr Val Arg
625                 630                 635                 640

Cys Val Lys Pro Asn Gln Leu Leu Lys Pro Leu Asn Phe Asp Lys Arg
                645                 650                 655

Ile Val Leu Gln Gln Leu Arg Cys Ser Gly Val Met Glu Ala Val Arg
            660                 665                 670

Ile Ser Cys Ala Gly Phe Pro Thr Arg Arg Thr Phe Phe Glu Phe Gln
        675                 680                 685

Asp Arg Phe Lys Val Leu Tyr Pro Asp Val Val Ala Gln Cys Gly Glu
    690                 695                 700

Asp Tyr Arg Leu Ala Cys Val Lys Val Leu Glu Arg Thr Gly Leu Glu
705                 710                 715                 720

Asp Tyr Gln Ile Gly Lys Thr Lys Val Phe Leu Arg Ala Gly Gln Met
                725                 730                 735

Ala Thr Leu Asp Ala Arg Arg Gln Thr Ile Leu Asn Ala Ala Ala
            740                 745                 750

<210> SEQ ID NO 17
<211> LENGTH: 2235
<212> TYPE: DNA
<213> ORGANISM: Chara australis
<220> FEATURE:
<221> NAME/KEY: misc_feature
<223> OTHER INFORMATION: CaM(CaM5049) motor domain

<400> SEQUENCE: 17
atggcaacgt tggagtgggt tccccagtg tgggttgaag atgaagagga tatgtggatt        60
gaggcgacgg tgctcaagat tgaggcagat aaggtcattt cgaagaacag gaaaggtggc       120
gaggttgttt cgtctaagga tatggtccat ccgagagacg aggacacggc tgaaatgggt       180
gttgacgaca tgacaaggtt gtcgtacctc cacgagcctg gagtgttgga caatctctcc       240
cgaagatacc acctcaatca aatttataca tacacaggga gcatttgtat cgccatcaat       300
cctttccaag cagtgccaca tttggttgga accaaactca tggaaatgtt caaggttgca       360
cagcctggag aggtcagcca acctcacgtg tatgcggtgg ctgacagagc ttacaaggct       420
atgatggatg aggaaaggag tcagtcaatt cttgtcagcg agaaagtgg tgcgggtaag       480 acggaagcga cgaagcttat catgaactac cttgccttta tgggaggcag agccactccc       540
gttgcaggag aaagatcagt ggagcagaag gtgttggagt caaatccact gctggaagcc       600
tttggaaatg caaagacagt ccgtaacaac aattccagtc gcttcggtaa atttgtggag       660
atccagttca acagaggcaa gatttctggg gctgcagtcc gaacctatct gctggagcga       720
tctcgtatca ctcaagtgtc gacacctgag cgtagttacc attgtttcta ccagctatgt       780
gcgggagcca caccgagga gagagaaaag ttgaagatcg aacctgctcc aaactacttc       840
tacctcaatc agagcgagtg ctttgaggtt cctcgatttg atgaagtaga agagtacagg       900
gcaactcgac atgccatgga cgttgtcggt atctccactg aggagcagga tggtattttc       960
cgaatcgttg catcaattct tcatcttgga aatgttgact caaaaccagg caaggaggca      1020
gactcctcac aacttgcaga tgataagtcc cgatttcacc tcacctgctg tgcggagttg      1080
```

-continued

```
ctgggagcga acccaaagct tctggaagat tcactcatcc aaagaatcat ggttacgagg    1140
ggagaagcca tcaccaagct cctggacaag aaacaggcta ttggaagtcg tgatgctctc    1200
gcaaaaactc tctatgccaa gatgtttgac tggttggtcg acaaggtcaa caagtccatc    1260
ggtcaagatc ccaactccaa cactctggtt ggtgtgcttg atatttatgg atttgagagc    1320
ttcactgtga acagtttcga gcagctttgc atcaatctca ccaatgaaaa gctgcagcag    1380
cacttcaaca cgcatgtctt caagatggag caagaggagt acgtgaagga agagatcaat    1440
tgggacaaca ttgactttgt tgataacata gatgttctgg acctcatcga gaagaaacca    1500
ttgggaatca ttgcgttgct cgatgaagcc tgcatgttgc ccaaatccac accggagtca    1560
tttggtcaga agcttgctca gtcatttgac aagcacaaac gatttacaaa gcacaagttc    1620
aagaagacac tgttcaaaat tgaccacttc gcaggagagg tggagtactc gacggacaca    1680
tttattgaaa agaacaagga tttcgtgatt gcggagcatc agcaactgct gacagggtcc    1740
acagattcat ttgtgagaca ggtgtatccg ccaccagagg agccaaagca gggcggaaag    1800
ggtggaggga agtcatcctt ctcctctatt ggaactcgct tcaagcaaca actgcaatca    1860
ctgatggaca cccttaacca gacagagccg cattatgtcc gttgcgtaaa gcccaaccag    1920
aaactgaagc cactcatgtt cgagaagcgg attgtcctcc agcagcttcg gtgcagtggt    1980
gtgttggaag ctgtgcgtat cagttgtgct ggtttcccaa caaggcgtac attcttcgag    2040
ttcgcagaca ggttcaaaat tttgtttccc gacgcagttg ccaactgtgg cgcggactat    2100
aagagcgcat gtgtcaagat cttggagaag attgggctcc agaggtatca gattggaaaa    2160
accaaggtgt ttttgcgagc aggtcagatg gctattctgg ataccaaacg taccgagatt    2220
ctcaacgagg cagcc                                                     2235
```

<210> SEQ ID NO 18
<211> LENGTH: 745
<212> TYPE: PRT
<213> ORGANISM: Chara australis
<220> FEATURE:
<221> NAME/KEY: MISC_FEATURE
<223> OTHER INFORMATION: CaM(CaM5049) motor domain

<400> SEQUENCE: 18

```
Met Ala Thr Phe Gly Val Gly Ser Pro Val Trp Val Glu Asp Glu
1               5                  10                  15

Asp Met Trp Ile Glu Ala Thr Val Leu Lys Ile Glu Ala Asp Lys Val
            20                  25                  30

Ile Ser Lys Asn Arg Lys Gly Gly Glu Val Val Ser Ser Lys Asp Met
        35                  40                  45

Val His Pro Arg Asp Glu Asp Thr Ala Glu Met Gly Val Asp Met
    50                  55                  60

Thr Arg Leu Ser Tyr Leu His Glu Pro Gly Val Leu Asp Asn Leu Ser
65                  70                  75                  80

Arg Arg Tyr His Leu Asn Gln Ile Tyr Thr Tyr Thr Gly Ser Ile Cys
                85                  90                  95

Ile Ala Ile Asn Pro Phe Gln Ala Val Pro His Leu Val Gly Thr Lys
            100                 105                 110

Leu Met Glu Met Phe Lys Val Ala Gln Pro Gly Glu Val Ser Gln Pro
        115                 120                 125

His Val Tyr Ala Val Ala Asp Arg Ala Tyr Lys Ala Met Met Asp Glu
    130                 135                 140
```

-continued

```
Glu Arg Ser Gln Ser Ile Leu Val Ser Gly Ser Gly Ala Gly Lys
145                 150                 155                 160

Thr Glu Ala Thr Lys Leu Ile Met Asn Tyr Leu Ala Phe Met Gly Gly
                165                 170                 175

Arg Ala Thr Pro Val Ala Gly Glu Arg Ser Val Glu Gln Lys Val Leu
            180                 185                 190

Glu Ser Asn Pro Leu Leu Glu Ala Phe Gly Asn Ala Lys Thr Val Arg
        195                 200                 205

Asn Asn Asn Ser Ser Arg Phe Gly Lys Phe Val Glu Ile Gln Phe Asn
    210                 215                 220

Arg Gly Lys Ile Ser Gly Ala Ala Val Arg Thr Tyr Leu Leu Glu Arg
225                 230                 235                 240

Ser Arg Ile Thr Gln Val Ser Thr Pro Glu Arg Ser Tyr His Cys Phe
                245                 250                 255

Tyr Gln Leu Cys Ala Gly Ala Thr Pro Glu Glu Arg Glu Lys Leu Lys
            260                 265                 270

Ile Glu Pro Ala Pro Asn Tyr Phe Tyr Leu Asn Gln Ser Glu Cys Phe
        275                 280                 285

Glu Val Pro Arg Phe Asp Glu Val Glu Glu Tyr Arg Ala Thr Arg His
    290                 295                 300

Ala Met Asp Val Val Gly Ile Ser Thr Glu Glu Gln Asp Gly Ile Phe
305                 310                 315                 320

Arg Ile Val Ala Ser Ile Leu His Leu Gly Asn Val Asp Phe Lys Pro
                325                 330                 335

Gly Lys Glu Ala Asp Ser Ser Gln Leu Ala Asp Asp Lys Ser Arg Phe
            340                 345                 350

His Leu Thr Cys Cys Ala Glu Leu Leu Gly Ala Asn Pro Lys Leu Leu
        355                 360                 365

Glu Asp Ser Leu Ile Gln Arg Ile Met Val Thr Arg Gly Glu Ala Ile
    370                 375                 380

Thr Lys Leu Leu Asp Lys Lys Gln Ala Ile Gly Ser Arg Asp Ala Leu
385                 390                 395                 400

Ala Lys Thr Leu Tyr Ala Lys Met Phe Asp Trp Leu Val Asp Lys Val
                405                 410                 415

Asn Lys Ser Ile Gly Gln Asp Pro Asn Ser Asn Thr Leu Val Gly Val
            420                 425                 430

Leu Asp Ile Tyr Gly Phe Glu Ser Phe Thr Val Asn Ser Phe Glu Gln
        435                 440                 445

Leu Cys Ile Asn Leu Thr Asn Glu Lys Leu Gln Gln His Phe Asn Thr
    450                 455                 460

His Val Phe Lys Met Glu Gln Glu Glu Tyr Val Lys Glu Glu Ile Asn
465                 470                 475                 480

Trp Asp Asn Ile Asp Phe Val Asp Asn Ile Asp Val Leu Asp Leu Ile
                485                 490                 495

Glu Lys Lys Pro Leu Gly Ile Ile Ala Leu Leu Asp Glu Ala Cys Met
            500                 505                 510

Leu Pro Lys Ser Thr Pro Glu Ser Phe Gly Gln Lys Leu Ala Gln Ser
        515                 520                 525

Phe Asp Lys His Lys Arg Phe Thr Lys His Lys Phe Lys Lys Thr Leu
    530                 535                 540

Phe Lys Ile Asp His Phe Ala Gly Glu Val Glu Tyr Ser Thr Asp Thr
545                 550                 555                 560

Phe Ile Glu Lys Asn Lys Asp Phe Val Ile Ala Glu His Gln Gln Leu
```

```
              565                 570                 575
Leu Thr Gly Ser Thr Asp Ser Phe Val Arg Gln Val Tyr Pro Pro
            580                 585                 590

Glu Glu Pro Lys Gln Gly Gly Lys Gly Gly Lys Ser Ser Phe Ser
            595                 600                 605

Ser Ile Gly Thr Arg Phe Lys Gln Gln Leu Gln Ser Leu Met Asp Thr
610                 615                 620

Leu Asn Gln Thr Glu Pro His Tyr Val Arg Cys Val Lys Pro Asn Gln
625                 630                 635                 640

Lys Leu Lys Pro Leu Met Phe Glu Lys Arg Ile Val Leu Gln Gln Leu
                645                 650                 655

Arg Cys Ser Gly Val Leu Glu Ala Val Arg Ile Ser Cys Ala Gly Phe
                660                 665                 670

Pro Thr Arg Arg Thr Phe Phe Glu Phe Ala Asp Arg Phe Lys Ile Leu
                675                 680                 685

Phe Pro Asp Ala Val Ala Asn Cys Gly Ala Asp Tyr Lys Ser Ala Cys
690                 695                 700

Val Lys Ile Leu Glu Lys Ile Gly Leu Gln Arg Tyr Gln Ile Gly Lys
705                 710                 715                 720

Thr Lys Val Phe Leu Arg Ala Gly Gln Met Ala Ile Leu Asp Thr Lys
                725                 730                 735

Arg Thr Glu Ile Leu Asn Glu Ala Ala
                740                 745

<210> SEQ ID NO 19
<211> LENGTH: 4590
<212> TYPE: DNA
<213> ORGANISM: Brachypodium distachyon
<220> FEATURE:
<221> NAME/KEY: misc_feature
<223> OTHER INFORMATION: Myosin XI-B (Bradi2g41977.1)

<400> SEQUENCE: 19
atgggtactc cagctaacat cattgttggt tctcatgttt gggtggagga ctcaactcta      60
gcttggatag atggcgaggt tgtcagcata aaaaacaatg aagttcacgt gcagacatca     120
aatgggaaaa aggttactac agacagatca aaagtttttc ccaaggatat ggaagctccg     180
ccaggaggag tggatgatat gacaagatta tcatacttac atgagcctgg tgttctacag     240
aatcttgcta cacgttatga actgaatgaa atatatactt acactggtag catattgatt     300
gcggtaaacc catttcaaag attgccacat ctttacgata cccacatgat ggaacaatac     360
aagggtgcag attttggaga gttgagtcct cacgtcttcg caattgcaga cgttgcttac     420
agagagatga taaatgaagg gaaaaacaac tctatattgg taagtggtga agtggtgct      480 ggcaagactg aaacaacaaa gatgcttatg cgatatctag cacacttagg aggacgatct     540
ggagtagagg ggagaacagt agagcaacaa gttctagagt caaacccagt tcttgaagct     600
tttggtaacg caaaaactgt gcgaaataat aactcgagtc gctttggcaa gttcgttgag     660
atccaattcg acaagactgg aaggatctcg ggagctgcta tcagaactta cttgctggaa     720
agatcccgtg tatgccaaat aaatactcca gaaagaaatt atcattgctt ttattttctt     780
tgtgctgcac cacccgagga tactcagagg tataagttgg ctgatgctag atcttttcat     840
tacctcaatc agtcaagttg tattgaggtt gaaggaatta atgatgctga agagtattta     900
gcaacaagaa gggccatgga tatagtagga atcaatgagg aagaacagga agctatattc     960
agggttgtag cagctgtact tcatattgga aacataaatt ttgccaaggg aacagaagta    1020
```

```
gattcatctg tgattaagga tgataattcc aggtttcacc ttaacactgc agcagagcta    1080
ttagagtgtg attgcaataa tctggaaaag gcactgataa cacgagtaat agttacccct    1140
gaagaaatta ttactagaac acttgatcct gattccgcac ttgctagcag agatgcatta    1200
gcgaaaacag tatattcccg attgtttgat tggattgtgg aaaaaattaa tgtttccatt    1260
ggacaggacc caaactctaa gcaattgatt ggtgttcttg atatttatgg gtttgagagt    1320
ttcaaagtta acagttttga acagttatgc atcaactata caaatgaaaa gcttcagcaa    1380
catttcaacc agcatgtgtt caaaatggag caagaggaat ataccagaga ggagataaac    1440
tggagttaca ttgagtttgt tgacaatcaa gatgtgctag acttgattga agagaaaggt    1500
gggttgattg cacttctgga cgaagcatgt atgtttccca gatcaacgca tgagacattt    1560
gcgcagaagc tgtatacaac tttcaagaat aacaagcgat tgtcaaacc aaagctttct    1620 cgtacagact ttacagttgt ccattatgct ggcgatgtga cataccaggc tgatcatttc    1680
ttagacaaga caaagatta tgtagtggct gaacatcagg atctgctgaa tgcttcttca    1740
tgtcctttcg tagctgcttt attcccttca ctccctgaag aatcttcaaa gtcttcaaaa    1800
ttttcctcta ttgggtcacg ttttaagctg cagcttcaat ctctgatgga gaccttgagc    1860
tctacagaac cccattatat tagatgtgtg aagccaaata atctcctcaa gccagccatt    1920
tttgagaaca caaatgtgat acaacaacta cgatgtggag gtgttcttga agctatcagg    1980
ataagctgtg ctgggtaccc cacaagaaaa acgttttatg aatttgttaa tcgctttggt    2040
gttcttggtc ctgaacttct agaaggaagc aacgatgata agattgcatg ccagaagatt    2100
ctggaaaaaa tgaagctgga aaactaccag ataggaaaaa cgaaggtgtt tctgagagct    2160
ggacagatgg ctgatttgga tgcacgaaga gcagaagtgt taggaaaagc agcaagaatt    2220
atacagagac taatgcgtac atatattgca cggaaacagt ttgttttggt tagaagatca    2280
gcaacacata tacagtcttt tgttagaggg accttggttc gtaatatgta cgagtgcatg    2340
aggcgagagt cagcagcaat gaaaatacaa agaatgtgc gtcgtcacaa agcacgtgaa    2400
tcttatttgc tactgcaagc agctgcagtc acgctgcaga caggcttaag ggcaatgtct    2460
gctcgcaaag aattcagatt cagaaaggaa accaaagcag ctatccatat ccaggctaga    2520
tggcgatgcc atagtgacta ttcacattac aagaatctgc aaggagcagc tcttacttac    2580
cagtgtgcct ggagacaaag gcttgcaaga agagagctca ggaatctcaa gatggctgcg    2640
agagaaacag ggccctcaa agaggccaaa gataaacttg agaagcgtgt tgaggagtta    2700
acatggcgct taggactgga gaagcgacta aggactgacc ttgaggaagc aaaatcccag    2760
gagattgcta agctgcaaga acattgaat gatacacagc tgcaagttga gaagcaaag    2820 gccatggttc ttaaggaaag agaagcagct agaaaggcaa ttgaagaagc cctccagta    2880 atcaaagaga ctcctgtatt ggttgaagat actgaaaaga ttaattctct cacaactgaa    2940
gttgaacaac ttaaggcttt gctgcaagct caaaggcaag ccacagagac tgcaaagaaa    3000
gaacatgctg aagctgaacg gagaaatgaa gaactgatga gaaatttga aggcgcagag    3060 aaaaagattg agcaacttca ggacactgcc cagaggctgg aagagaaagc aactaacatg    3120
gagtctgaga acaaagtgct ccgtcaacag gctgttgcaa tttctcctac tgcaaaatca    3180
ttagctgcat atcctaaatc tccttccaa ctgagaactc cggagaacgt gaatgctcca    3240 aatgggagg tgaaatcatc gccagatgta acccccatct cactgaattc caagagctt    3300 gaggctgagg agaaacctca aaaatcactt aacgagaagc agcaggaaaa ccaagacttg    3360
```

| | |
|---|---|
| ctaatcaagt gtgtatcaca agatctggga ttctccagtg gtagggctat tgcagcttgt | 3420 |
| gttatataca gatgccttct acattggcga tcatttgaag ttgaaagaac tggtgttttc | 3480 |
| gaccgtatta ttcaaacaat cggtactgct atagaggccc aggacaataa cgacaagtta | 3540 |
| gcatattggc tctctaattc atccacatta ctcctactac tacaacgaac actgaaaaca | 3600 |
| actggagcag ctggactcac tcctcagagg cgaaggtcat ctgctgcatc atttggagg | 3660 |
| gttttctcgg gaattcgagc ttcaccacaa agtgccccgc gtgcttttct tggtagccgc | 3720 |
| ttgattggag gactaggtga tcttcgtcaa gttgaagcta agtatcctgc tctgcttttc | 3780 |
| aagcagcagc taacagcctt ccttgagaaa atctacggaa tgattagaga caatctgaag | 3840 |
| aaagagatat ctccattgct tggtctttgc atccaggcac aagaacatc tcgcgcaagt | 3900 |
| ctaataaaag gatctcgttc acaagcaaat gccttggcac aacaaacttt aatcgcccat | 3960 |
| tggcagagta ttgtgaaaat attaacaaac tacctgaatg ttttgaaagc caactatgtc | 4020 |
| ccttcattct taatcagcaa ggtgttcact caaatctttt catttattaa cgttcagttg | 4080 |
| ttcaatagtc tgctcctccg acgagagtgc tgttcattta gcaatgggga gtatgtcaaa | 4140 |
| gctggattgg ccgagttgga gcaatggtgc atttacgcga ctgaagagta tgcaggttct | 4200 |
| tcctgggaag aattgaagca tattaggcag gctgttggat tccttgtaat tcatcaaaag | 4260 |
| ccaaagaaaa cgttgaaaga atcaccaac gatttgtgtc ctgtccttag catacaacag | 4320 |
| ctttatcgaa ttagtacaat gtattgggat gacaaatatg gcacccacac agtttcctca | 4380 |
| gaggtcatct caagtatgag aataatgatg acagaagact caaacaatgc agtgagcagt | 4440 |
| tctttcctgt tggatgatga ttcaagcatt ccatttccgg tggatgacat ctcaaagtca | 4500 |
| atgacagaaa ttgagataac ggacgttgat atgccacctt tgatccggga gaattctggc | 4560 |
| tttaccttcc tacaccaaag aaaggactga | 4590 |

<210> SEQ ID NO 20
<211> LENGTH: 1529
<212> TYPE: PRT
<213> ORGANISM: Brachypodium distachyon
<220> FEATURE:
<221> NAME/KEY: MISC_FEATURE
<223> OTHER INFORMATION: Myosin XI-B (Bradi2g41977.1)

<400> SEQUENCE: 20

Met Gly Thr Pro Ala Asn Ile Ile Val Gly Ser His Val Trp Val Glu
1               5                   10                  15

Asp Ser Thr Leu Ala Trp Ile Asp Gly Glu Val Val Ser Ile Lys Asn
            20                  25                  30

Asn Glu Val His Val Gln Thr Ser Asn Gly Lys Lys Val Thr Thr Asp
        35                  40                  45

Arg Ser Lys Val Phe Pro Lys Asp Met Glu Ala Pro Gly Gly Val
    50                  55                  60

Asp Asp Met Thr Arg Leu Ser Tyr Leu His Glu Pro Gly Val Leu Gln
65                  70                  75                  80

Asn Leu Ala Thr Arg Tyr Glu Leu Asn Glu Ile Tyr Thr Tyr Thr Gly
                85                  90                  95

Ser Ile Leu Ile Ala Val Asn Pro Phe Gln Arg Leu Pro His Leu Tyr
            100                 105                 110

Asp Thr His Met Met Glu Gln Tyr Lys Gly Ala Asp Phe Gly Glu Leu
        115                 120                 125

Ser Pro His Val Phe Ala Ile Ala Asp Val Ala Tyr Arg Glu Met Ile
    130                 135                 140

-continued

```
Asn Glu Gly Lys Asn Asn Ser Ile Leu Val Ser Gly Glu Ser Gly Ala
145                 150                 155                 160

Gly Lys Thr Glu Thr Thr Lys Met Leu Met Arg Tyr Leu Ala His Leu
            165                 170                 175

Gly Gly Arg Ser Gly Val Glu Gly Arg Thr Val Glu Gln Gln Val Leu
        180                 185                 190

Glu Ser Asn Pro Val Leu Glu Ala Phe Gly Asn Ala Lys Thr Val Arg
    195                 200                 205

Asn Asn Asn Ser Ser Arg Phe Gly Lys Phe Val Glu Ile Gln Phe Asp
210                 215                 220

Lys Thr Gly Arg Ile Ser Gly Ala Ala Ile Arg Thr Tyr Leu Leu Glu
225                 230                 235                 240

Arg Ser Arg Val Cys Gln Ile Asn Thr Pro Glu Arg Asn Tyr His Cys
                245                 250                 255

Phe Tyr Phe Leu Cys Ala Ala Pro Pro Glu Asp Thr Gln Arg Tyr Lys
            260                 265                 270

Leu Ala Asp Ala Arg Ser Phe His Tyr Leu Asn Gln Ser Ser Cys Ile
        275                 280                 285

Glu Val Glu Gly Ile Asn Asp Ala Glu Glu Tyr Leu Ala Thr Arg Arg
    290                 295                 300

Ala Met Asp Ile Val Gly Ile Asn Glu Glu Gln Glu Ala Ile Phe
305                 310                 315                 320

Arg Val Val Ala Ala Val Leu His Ile Gly Asn Ile Asn Phe Ala Lys
                325                 330                 335

Gly Thr Glu Val Asp Ser Ser Val Ile Lys Asp Asp Asn Ser Arg Phe
            340                 345                 350

His Leu Asn Thr Ala Ala Glu Leu Leu Glu Cys Asp Cys Asn Asn Leu
        355                 360                 365

Glu Lys Ala Leu Ile Thr Arg Val Ile Val Thr Pro Glu Glu Ile Ile
    370                 375                 380

Thr Arg Thr Leu Asp Pro Asp Ser Ala Leu Ala Ser Arg Asp Ala Leu
385                 390                 395                 400

Ala Lys Thr Val Tyr Ser Arg Leu Phe Asp Trp Ile Val Glu Lys Ile
                405                 410                 415

Asn Val Ser Ile Gly Gln Asp Pro Asn Ser Lys Gln Leu Ile Gly Val
            420                 425                 430

Leu Asp Ile Tyr Gly Phe Glu Ser Phe Lys Val Asn Ser Phe Glu Gln
        435                 440                 445

Leu Cys Ile Asn Tyr Thr Asn Glu Lys Leu Gln Gln His Phe Asn Gln
    450                 455                 460

His Val Phe Lys Met Glu Gln Glu Glu Tyr Thr Arg Glu Glu Ile Asn
465                 470                 475                 480

Trp Ser Tyr Ile Glu Phe Val Asp Asn Gln Asp Val Leu Asp Leu Ile
                485                 490                 495

Glu Lys Lys Gly Gly Leu Ile Ala Leu Leu Asp Glu Ala Cys Met Phe
            500                 505                 510

Pro Arg Ser Thr His Glu Thr Phe Ala Gln Lys Leu Tyr Thr Thr Phe
        515                 520                 525

Lys Asn Asn Lys Arg Phe Val Lys Pro Lys Leu Ser Arg Thr Asp Phe
    530                 535                 540

Thr Val Val His Tyr Ala Gly Asp Val Thr Tyr Gln Ala Asp His Phe
545                 550                 555                 560
```

-continued

```
Leu Asp Lys Asn Lys Asp Tyr Val Val Ala Glu His Gln Asp Leu Leu
                565                 570                 575
Asn Ala Ser Ser Cys Pro Phe Val Ala Ala Leu Phe Pro Ser Leu Pro
            580                 585                 590
Glu Glu Ser Ser Lys Ser Ser Lys Phe Ser Ser Ile Gly Ser Arg Phe
        595                 600                 605
Lys Leu Gln Leu Gln Ser Leu Met Glu Thr Leu Ser Ser Thr Glu Pro
    610                 615                 620
His Tyr Ile Arg Cys Val Lys Pro Asn Asn Leu Leu Lys Pro Ala Ile
625                 630                 635                 640
Phe Glu Asn Thr Asn Val Ile Gln Gln Leu Arg Cys Gly Gly Val Leu
                645                 650                 655
Glu Ala Ile Arg Ile Ser Cys Ala Gly Tyr Pro Thr Arg Lys Thr Phe
            660                 665                 670
Tyr Glu Phe Val Asn Arg Phe Gly Val Leu Gly Pro Glu Leu Leu Glu
        675                 680                 685
Gly Ser Asn Asp Asp Lys Ile Ala Cys Gln Lys Ile Leu Glu Lys Met
    690                 695                 700
Lys Leu Glu Asn Tyr Gln Ile Gly Lys Thr Lys Val Phe Leu Arg Ala
705                 710                 715                 720
Gly Gln Met Ala Asp Leu Asp Ala Arg Arg Ala Glu Val Leu Gly Lys
                725                 730                 735
Ala Ala Arg Ile Ile Gln Arg Leu Met Arg Thr Tyr Ile Ala Arg Lys
            740                 745                 750
Gln Phe Val Leu Val Arg Arg Ser Ala Thr His Ile Gln Ser Phe Val
        755                 760                 765
Arg Gly Thr Leu Val Arg Asn Met Tyr Glu Cys Met Arg Arg Glu Ser
    770                 775                 780
Ala Ala Met Lys Ile Gln Lys Asn Val Arg Arg His Lys Ala Arg Glu
785                 790                 795                 800
Ser Tyr Leu Leu Leu Gln Ala Ala Val Thr Leu Gln Thr Gly Leu
                805                 810                 815
Arg Ala Met Ser Ala Arg Lys Glu Phe Arg Phe Arg Lys Glu Thr Lys
            820                 825                 830
Ala Ala Ile His Ile Gln Ala Arg Trp Arg Cys His Ser Asp Tyr Ser
        835                 840                 845
His Tyr Lys Asn Leu Gln Gly Ala Ala Leu Thr Tyr Gln Cys Ala Trp
    850                 855                 860
Arg Gln Arg Leu Ala Arg Arg Glu Leu Arg Asn Leu Lys Met Ala Ala
865                 870                 875                 880
Arg Glu Thr Gly Ala Leu Lys Glu Ala Lys Asp Lys Leu Glu Lys Arg
                885                 890                 895
Val Glu Glu Leu Thr Trp Arg Leu Gly Leu Glu Lys Arg Leu Arg Thr
            900                 905                 910
Asp Leu Glu Glu Ala Lys Ser Gln Glu Ile Ala Lys Leu Gln Glu Thr
        915                 920                 925
Leu Asn Asp Thr Gln Leu Gln Val Glu Ala Lys Ala Met Val Leu
    930                 935                 940
Lys Glu Arg Glu Ala Ala Arg Lys Ala Ile Glu Ala Pro Pro Val
945                 950                 955                 960
Ile Lys Glu Thr Pro Val Leu Val Glu Asp Thr Glu Lys Ile Asn Ser
                965                 970                 975
Leu Thr Thr Glu Val Glu Gln Leu Lys Ala Leu Leu Gln Ala Gln Arg
```

-continued

```
                980                 985                 990
Gln Ala Thr Glu Thr Ala Lys Lys Glu His Ala Glu Ala Glu Arg Arg
                995                1000                1005
Asn Glu Glu Leu Met Lys Lys Phe Glu Gly Ala Glu Lys Lys Ile
       1010                1015               1020
Glu Gln Leu Gln Asp Thr Ala Gln Arg Leu Glu Glu Lys Ala Thr
       1025                1030               1035
Asn Met Glu Ser Glu Asn Lys Val Leu Arg Gln Ala Val Ala
       1040                1045               1050
Ile Ser Pro Thr Ala Lys Ser Leu Ala Ala Tyr Pro Lys Ser Pro
       1055                1060               1065
Phe Gln Leu Arg Thr Pro Glu Asn Val Asn Ala Pro Asn Gly Glu
       1070                1075               1080
Val Lys Ser Ser Pro Asp Val Thr Pro Ile Ser Leu Asn Ser Lys
       1085                1090               1095
Glu Leu Glu Ala Glu Glu Lys Pro Gln Lys Ser Leu Asn Glu Lys
       1100                1105               1110
Gln Gln Glu Asn Gln Asp Leu Leu Ile Lys Cys Val Ser Gln Asp
       1115                1120               1125
Leu Gly Phe Ser Ser Gly Arg Ala Ile Ala Ala Cys Val Ile Tyr
       1130                1135               1140
Arg Cys Leu Leu His Trp Arg Ser Phe Glu Val Glu Arg Thr Gly
       1145                1150               1155
Val Phe Asp Arg Ile Ile Gln Thr Ile Gly Thr Ala Ile Glu Ala
       1160                1165               1170
Gln Asp Asn Asn Asp Lys Leu Ala Tyr Trp Leu Ser Asn Ser Ser
       1175                1180               1185
Thr Leu Leu Leu Leu Leu Gln Arg Thr Leu Lys Thr Thr Gly Ala
       1190                1195               1200
Ala Gly Leu Thr Pro Gln Arg Arg Arg Ser Ser Ala Ala Ser Phe
       1205                1210               1215
Gly Arg Val Phe Ser Gly Ile Arg Ala Ser Pro Gln Ser Ala Pro
       1220                1225               1230
Arg Ala Phe Leu Gly Ser Arg Leu Ile Gly Gly Leu Gly Asp Leu
       1235                1240               1245
Arg Gln Val Glu Ala Lys Tyr Pro Ala Leu Leu Phe Lys Gln Gln
       1250                1255               1260
Leu Thr Ala Phe Leu Glu Lys Ile Tyr Gly Met Ile Arg Asp Asn
       1265                1270               1275
Leu Lys Lys Glu Ile Ser Pro Leu Leu Gly Leu Cys Ile Gln Ala
       1280                1285               1290
Pro Arg Thr Ser Arg Ala Ser Leu Ile Lys Gly Ser Arg Ser Gln
       1295                1300               1305
Ala Asn Ala Leu Ala Gln Gln Thr Leu Ile Ala His Trp Gln Ser
       1310                1315               1320
Ile Val Lys Ile Leu Thr Asn Tyr Leu Asn Val Leu Lys Ala Asn
       1325                1330               1335
Tyr Val Pro Ser Phe Leu Ile Ser Lys Val Phe Thr Gln Ile Phe
       1340                1345               1350
Ser Phe Ile Asn Val Gln Leu Phe Asn Ser Leu Leu Leu Arg Arg
       1355                1360               1365
Glu Cys Cys Ser Phe Ser Asn Gly Glu Tyr Val Lys Ala Gly Leu
       1370                1375               1380
```

| Ala | Glu | Leu | Glu | Gln | Trp | Cys | Ile | Tyr | Ala | Thr | Glu | Glu | Tyr | Ala |
| | | 1385 | | | | 1390 | | | | 1395 | | | | |

| Gly | Ser | Ser | Trp | Glu | Glu | Leu | Lys | His | Ile | Arg | Gln | Ala | Val | Gly |
| 1400 | | | | | 1405 | | | | | 1410 | | | | |

| Phe | Leu | Val | Ile | His | Gln | Lys | Pro | Lys | Lys | Thr | Leu | Lys | Glu | Ile |
| 1415 | | | | | 1420 | | | | | 1425 | | | | |

| Thr | Asn | Asp | Leu | Cys | Pro | Val | Leu | Ser | Ile | Gln | Gln | Leu | Tyr | Arg |
| 1430 | | | | | 1435 | | | | | 1440 | | | | |

| Ile | Ser | Thr | Met | Tyr | Trp | Asp | Asp | Lys | Tyr | Gly | Thr | His | Thr | Val |
| 1445 | | | | | 1450 | | | | | 1455 | | | | |

| Ser | Ser | Glu | Val | Ile | Ser | Ser | Met | Arg | Ile | Met | Met | Thr | Glu | Asp |
| 1460 | | | | | 1465 | | | | | 1470 | | | | |

| Ser | Asn | Asn | Ala | Val | Ser | Ser | Phe | Leu | Leu | Asp | Asp | Asp | Ser |
| 1475 | | | | | 1480 | | | | | 1485 | | | | |

| Ser | Ile | Pro | Phe | Ser | Val | Asp | Ile | Ser | Lys | Ser | Met | Thr | Glu |
| 1490 | | | | | 1495 | | | | | 1500 | | | | |

| Ile | Glu | Ile | Thr | Asp | Val | Asp | Met | Pro | Pro | Leu | Ile | Arg | Glu | Asn |
| 1505 | | | | | 1510 | | | | | 1515 | | | | |

| Ser | Gly | Phe | Thr | Phe | Leu | His | Gln | Arg | Lys | Asp |
| 1520 | | | | | 1525 | | | | | |

<210> SEQ ID NO 21
<211> LENGTH: 4611
<212> TYPE: DNA
<213> ORGANISM: Artificial Sequence
<220> FEATURE:
<223> OTHER INFORMATION: Chimera protein: Myosin XI in which the motor
      domain of myosin XI-B (Brachypodium distachyon) is substituted
      with myosin XI of CbM 1 (Chara braunni)

<400> SEQUENCE: 21

```
atggcaacgt tggagtcgg ttccccagtg tgggttgaag atgaagagga tatgtggatt      60
gaggcaacgg tgctcaagat cgaggcagat aaggtcattt cgaagaacag gaaaggtggc    120
gaggttgttt cgtctaagga tatggtccat ccgagagacg aggacacggc tgaaatgggt    180
gttgacgaca tgacgaggtt gtcgtacctc acgagcctg gagtattgga caatctttcc    240
cgaagatacc acctcaatca aatttataca tacacaggga gcatttgtat cgccatcaat    300
cctttccaag cagtgccaca tttggttgga accaaactca tggaaatgtt caaggttgca    360
cagcctggag aggtcagcca acctcacgtg tatgcagtgg ctgacagagc ttacaaggct    420
atgatggatg aggaaaagag tcagtcaatt cttgtcagtg gagaaagtgg tgcgggtaag    480
acagaagcga caaagcttat catgaactac cttgccttta tgggagggag ggccactccc    540
gttgcaggag aaagatcagt ggagcagaag gtgttggagt caaatccact gctggaagcc    600
tccggaaatg caaagacagt ccgtaacaac aattccagtc gcttcggtaa attcgtggag    660
atccagttca cagaggcaa gatttctggg gctgcagttc gaacctatct gctggagcga    720
tctcgtatca ctcaagtgtc gacacctgag cgtagttacc attgtttcta ccagctatgt    780
gcggagccca gcagagga gagagaaaag ctgaagatcg aagctgctcc aaactacttc    840
tacctcaatc agagcgagtg ttttgaggtt cctcgatttg atgaagtaga agagtacaag    900
gcaactcgac atgccatgga tgttgtgggt atctccactg aggagcagga tggtatttc    960 cgaatcgttg catcaattct tcatcttgga aatgttgact caaaccagg caaggaggca   1020 gactcctcac aacttgcaga tgacaagtcc cgatttcacc tcaactgctg tgcggagttg   1080
```

```
ctgggagcga acccaaagct tctggaagat tcactcatcc aaagaatcat ggttacgagg   1140
ggagaagcca tcaccaagct actgacaaag aaacaggctg ttggaagtcg tgatgctctc   1200
gcaaaaactc tctatgccaa gatgttcgac tggttggtcg acaaggtcaa caagtccatt   1260
ggtcaagatc ccaactccaa cactctggtt ggtgtgcttg atatttatgg ctttgagagc   1320
ttcacggtga acagtttcga gcagctttgc atcaatctca caaatgaaaa gctgcagcag   1380
cacttcaaca cgcatgtctt caagatggag caagaggagt acgtgaagga agagatcaac   1440
tgggacaaca ttgactttgt tgataacata gatgttctgg accttatcga agagaaacca   1500
ttgggaatca ttgctttgct cgatgaagcc tgcatgttgc ccaaatccac accggagtca   1560
tttggccaaa agcttgctca gtcttttgac aagcacaaac gatttacaaa gcacaagttc   1620
aagaagacac tgttcaaaat tgaccacttt gcaggagagg tggagtactc gacgacaca    1680 tttattgaaa agaacaagga tttcgtgatt gcggagcatc agcaactgct gacagcgtcc   1740
acagatccat ttgtgagaca ggtgtatccg ccaccagagg agccaaagca gggcggaaag   1800
ggtggaggga agtcatcctt ctcctctatt ggaactcgtt tcaagcaaca actgcaatct   1860
ctgatggaca cccttaacca gacagagccg cattatgtcc gttgcgtgaa gcccaaccag   1920
aaactgaagc cactcatgtt cgagaagcgg attgtcctcc agcagcttcg gtgcagtggt   1980
gtgttggaag ctgtgcgtat cagttgtgct ggtttcccaa caaggcgtac attcttcgag   2040
tttgcagaca gattcaagat tttgtttccc gatgcagttg ccaactgtgg ccaggactat   2100
aagagcgcat gtgtcaagat cctggagaag attgggctcg agaggtatca gattggaaaa   2160
accaaggtgt ttttgcgagc aggccagatg gctattctgg atacaaaacg taccgagatt   2220
ctcggaaaag cagcaagaat tatacagaga ctaatgcgta catatattgc acggaaacag   2280
tttgttttgg ttagaagatc agcaaacacat atacagtctt tgttagagg accttggtt    2340 cgtaatatgt acgagtgcat gaggcgagag tcagcagcaa tgaaaataca aaagaatgtg   2400
cgtcgtcaca agcacgtgaa atcttatttg ctactgcaag cagctgcagt cacgctgcag   2460
acaggcttaa gggcaatgtc tgctcgcaaa gaattcagat tcagaaagga accaaagca    2520 gctatccata tccaggctag atggcgatgc catagtgact attcacatta caagaatctg   2580
caaggagcag ctcttactta ccagtgtgcc tggagacaaa ggcttgcaag aagagagctc   2640
aggaatctca agatggctgc gagagaaaca ggggccctca agaggccaa agataaactt    2700 gagaagcgtg ttgaggagtt aacatggcgc ttaggactgg agaagcgact aaggactgac   2760
cttgaggaag caaaatccca ggagattgct aagctgcaag aaacattgaa tgatacacag   2820
ctgcaagttg aagaagcaaa ggccatggtt cttaaggaaa gagaagcagc tagaaaggca   2880
attgaagaag cacctccagt aatcaaagag actcctgtat tggttgaaga tactgaaaag   2940
attaattctc tcacaactga agttgaacaa cttaaggctt tgctgcaagc tcaaaggcaa   3000
gccacagaga ctgcaaagaa agaacatgct gaagctgaac ggagaaatga agaactgatg   3060
aagaaatttg aaggcgcaga gaaaaagatt gagcaacttc aggacactgc ccagaggctg   3120
gaagagaaag caactaacat ggagtctgag aacaaagtgc tccgtcaaca ggctgttgca   3180
atttctccta ctgcaaaatc attagctgca tatcctaaat ctccttttcca actgagaact   3240 ccggagaacg tgaatgctcc aaatggggag gtgaaatcat cgccagatgt aaccccccatc   3300 tcactgaatt ccaaagagct tgaggctgag gagaaacctc aaaaatcact taacgagaag   3360
cagcaggaaa accaagactt gctaatcaag tgtgtatcac aagatctggg attctccagt   3420
ggtagggcta ttgcagcttg tgttatatac agatgccttc tacattggcg atcatttgaa   3480
```

```
gttgaaagaa ctggtgtttt cgaccgtatt attcaaacaa tcggtactgc tatagaggcc    3540
caggacaata acgacaagtt agcatattgg ctctctaatt catccacatt actcctacta    3600
ctacaacgaa cactgaaaac aactggagca gctggactca ctcctcagag gcgaaggtca    3660
tctgctgcat catttgggag ggttttctcg ggaattcgag cttcaccaca aagtgccccg    3720
cgtgcttttc ttggtagccg cttgattgga ggactaggtg atcttcgtca agttgaagct    3780
aagtatcctg ctctgctttt caagcagcag ctaacagcct tccttgagaa aatctacgga    3840
atgattagag acaatctgaa gaaagagata tctccattgc ttggtctttg catccaggca    3900
ccaagaacat ctcgcgcaag tctaataaaa ggatctcgtt cacaagcaaa tgccttggca    3960
caacaaactt taatcgccca ttggcagagt attgtgaaaa tattaacaaa ctacctgaat    4020
gttttgaaag ccaactatgt cccttcattc ttaatcagca aggtgttcac tcaaatcttt    4080
tcatttatta acgttcagtt gttcaatagt ctgctcctcc gacgagagtg ctgttcattt    4140
agcaatgggg agtatgtcaa agctggattg gccgagttgg agcaatggtg catttacgcg    4200
actgaagagt atgcaggttc ttcctgggaa gaattgaagc atattaggca ggctgttgga    4260
ttccttgtaa ttcatcaaaa gccaaagaaa acgttgaaag aaatcaccaa cgatttgtgt    4320
cctgtcctta gcatacaaca gctttatcga attagtacaa tgtattggga tgacaaatat    4380
ggcacccaca cagtttcctc agaggtcatc tcaagtatga gaataatgat gacagaagac    4440
tcaaacaatg cagtgagcag ttctttcctg ttggatgatg attcaagcat tccattttcg    4500
gtggatgaca tctcaaagtc aatgacagaa attgagataa cggacgttga tatgccacct    4560
ttgatccggg agaattctgg ctttaccttc ctacaccaaa gaaaggactg a             4611
```

<210> SEQ ID NO 22
<211> LENGTH: 1536
<212> TYPE: PRT
<213> ORGANISM: Artificial Sequence
<220> FEATURE:
<223> OTHER INFORMATION: Chimera protein: Myosin XI in which the motor
      domain of myosin XI-B (Brachypodium distachyon) is substituted
      with myosin XI of CbM 1 (Chara braunni)

<400> SEQUENCE: 22

```
Met Ala Thr Phe Gly Val Gly Ser Pro Val Trp Val Glu Asp Glu
1               5                   10                  15

Asp Met Trp Ile Glu Ala Thr Val Leu Lys Ile Glu Ala Asp Lys Val
            20                  25                  30

Ile Ser Lys Asn Arg Lys Gly Gly Glu Val Val Ser Ser Lys Asp Met
        35                  40                  45

Val His Pro Arg Asp Glu Asp Thr Ala Glu Met Gly Val Asp Asp Met
    50                  55                  60

Thr Arg Leu Ser Tyr Leu His Glu Pro Gly Val Leu Asp Asn Leu Ser
65                  70                  75                  80

Arg Arg Tyr His Leu Asn Gln Ile Tyr Thr Tyr Thr Gly Ser Ile Cys
                85                  90                  95

Ile Ala Ile Asn Pro Phe Gln Ala Val Pro His Leu Val Gly Thr Lys
            100                 105                 110

Leu Met Glu Met Phe Lys Val Ala Gln Pro Gly Glu Val Ser Gln Pro
        115                 120                 125

His Val Tyr Ala Val Ala Asp Arg Ala Tyr Lys Ala Met Met Asp Glu
    130                 135                 140

Glu Lys Ser Gln Ser Ile Leu Val Ser Gly Glu Ser Gly Ala Gly Lys
```

```
            145                 150                 155                 160
        Thr Glu Ala Thr Lys Leu Ile Met Asn Tyr Leu Ala Phe Met Gly Gly
                            165                 170                 175

Arg Ala Thr Pro Val Ala Gly Glu Arg Ser Val Glu Gln Lys Val Leu
                            180                 185                 190

Glu Ser Asn Pro Leu Leu Glu Ala Phe Gly Asn Ala Lys Thr Val Arg
                            195                 200                 205

Asn Asn Asn Ser Ser Arg Phe Gly Lys Phe Val Glu Ile Gln Phe Asn
                    210                 215                 220

Arg Gly Lys Ile Ser Gly Ala Ala Val Arg Thr Tyr Leu Leu Glu Arg
        225                 230                 235                 240

Ser Arg Ile Thr Gln Val Ser Thr Pro Glu Arg Ser Tyr His Cys Phe
                            245                 250                 255

Tyr Gln Leu Cys Ala Gly Ala Thr Ala Glu Glu Arg Glu Lys Leu Lys
                            260                 265                 270

Ile Glu Ala Ala Pro Asn Tyr Phe Tyr Leu Asn Gln Ser Glu Cys Phe
                            275                 280                 285

Glu Val Pro Arg Phe Asp Glu Val Glu Glu Tyr Lys Ala Thr Arg His
                            290                 295                 300

Ala Met Asp Val Val Gly Ile Ser Thr Glu Glu Gln Asp Gly Ile Phe
        305                 310                 315                 320

Arg Ile Val Ala Ser Ile Leu His Leu Gly Asn Val Asp Phe Lys Pro
                            325                 330                 335

Gly Lys Glu Ala Asp Ser Ser Gln Leu Ala Asp Asp Lys Ser Arg Phe
                            340                 345                 350

His Leu Asn Cys Cys Ala Glu Leu Leu Gly Ala Asn Pro Lys Leu Leu
                            355                 360                 365

Glu Asp Ser Leu Ile Gln Arg Ile Met Val Thr Arg Gly Glu Ala Ile
                            370                 375                 380

Thr Lys Leu Leu Asp Lys Lys Gln Ala Val Gly Ser Arg Asp Ala Leu
        385                 390                 395                 400

Ala Lys Thr Leu Tyr Ala Lys Met Phe Asp Trp Leu Val Asp Lys Val
                            405                 410                 415

Asn Lys Ser Ile Gly Gln Asp Pro Asn Ser Asn Thr Leu Val Gly Val
                            420                 425                 430

Leu Asp Ile Tyr Gly Phe Glu Ser Phe Thr Val Asn Ser Phe Glu Gln
                            435                 440                 445

Leu Cys Ile Asn Leu Thr Asn Glu Lys Leu Gln Gln His Phe Asn Thr
                            450                 455                 460

His Val Phe Lys Met Glu Gln Glu Glu Tyr Val Lys Glu Glu Ile Asn
        465                 470                 475                 480

Trp Asp Asn Ile Asp Phe Val Asp Asn Ile Asp Val Leu Asp Leu Ile
                            485                 490                 495

Glu Lys Lys Pro Leu Gly Ile Ile Ala Leu Leu Asp Glu Ala Cys Met
                            500                 505                 510

Leu Pro Lys Ser Thr Pro Glu Ser Phe Gly Gln Lys Leu Ala Gln Ser
                            515                 520                 525

Phe Asp Lys His Lys Arg Phe Thr Lys His Lys Phe Lys Lys Thr Leu
                            530                 535                 540

Phe Lys Ile Asp His Phe Ala Gly Glu Val Glu Tyr Ser Thr Asp Thr
        545                 550                 555                 560

Phe Ile Glu Lys Asn Lys Asp Phe Val Ile Ala Glu His Gln Gln Leu
                            565                 570                 575
```

-continued

Leu Thr Ala Ser Thr Asp Pro Phe Val Arg Gln Val Tyr Pro Pro
            580                 585                 590

Glu Glu Pro Lys Gln Gly Gly Lys Gly Gly Gly Lys Ser Ser Phe Ser
        595                 600                 605

Ser Ile Gly Thr Arg Phe Lys Gln Gln Leu Gln Ser Leu Met Asp Thr
610                 615                 620

Leu Asn Gln Thr Glu Pro His Tyr Val Arg Cys Val Lys Pro Asn Gln
625                 630                 635                 640

Lys Leu Lys Pro Leu Met Phe Glu Lys Arg Ile Val Leu Gln Gln Leu
                645                 650                 655

Arg Cys Ser Gly Val Leu Glu Ala Val Arg Ile Ser Cys Ala Gly Phe
            660                 665                 670

Pro Thr Arg Arg Thr Phe Phe Glu Phe Ala Asp Arg Phe Lys Ile Leu
        675                 680                 685

Phe Pro Asp Ala Val Ala Asn Cys Gly Gln Asp Tyr Lys Ser Ala Cys
690                 695                 700

Val Lys Ile Leu Glu Lys Ile Gly Leu Glu Arg Tyr Gln Ile Gly Lys
705                 710                 715                 720

Thr Lys Val Phe Leu Arg Ala Gly Gln Met Ala Ile Leu Asp Thr Lys
                725                 730                 735

Arg Thr Glu Ile Leu Gly Lys Ala Ala Arg Ile Ile Gln Arg Leu Met
            740                 745                 750

Arg Thr Tyr Ile Ala Arg Lys Gln Phe Val Leu Val Arg Arg Ser Ala
        755                 760                 765

Thr His Ile Gln Ser Phe Val Arg Gly Thr Leu Val Arg Asn Met Tyr
770                 775                 780

Glu Cys Met Arg Arg Glu Ser Ala Ala Met Lys Ile Gln Lys Asn Val
785                 790                 795                 800

Arg Arg His Lys Ala Arg Glu Ser Tyr Leu Leu Leu Gln Ala Ala Ala
                805                 810                 815

Val Thr Leu Gln Thr Gly Leu Arg Ala Met Ser Ala Arg Lys Glu Phe
            820                 825                 830

Arg Phe Arg Lys Glu Thr Lys Ala Ala Ile His Ile Gln Ala Arg Trp
        835                 840                 845

Arg Cys His Ser Asp Tyr Ser His Tyr Lys Asn Leu Gln Gly Ala Ala
850                 855                 860

Leu Thr Tyr Gln Cys Ala Trp Arg Gln Arg Leu Ala Arg Arg Glu Leu
865                 870                 875                 880

Arg Asn Leu Lys Met Ala Ala Arg Glu Thr Gly Ala Leu Lys Glu Ala
                885                 890                 895

Lys Asp Lys Leu Glu Lys Arg Val Glu Glu Leu Thr Trp Arg Leu Gly
            900                 905                 910

Leu Glu Lys Arg Leu Arg Thr Asp Leu Glu Glu Ala Lys Ser Gln Glu
        915                 920                 925

Ile Ala Lys Leu Gln Glu Thr Leu Asn Asp Thr Gln Leu Gln Val Glu
930                 935                 940

Glu Ala Lys Ala Met Val Leu Lys Glu Arg Glu Ala Ala Arg Lys Ala
945                 950                 955                 960

Ile Glu Glu Ala Pro Pro Val Ile Lys Glu Thr Pro Val Leu Val Glu
                965                 970                 975

Asp Thr Glu Lys Ile Asn Ser Leu Thr Thr Glu Val Glu Gln Leu Lys
            980                 985                 990

```
Ala Leu Leu Gln Ala Gln Arg Gln Ala Thr Glu Thr Ala Lys Lys Glu
            995                 1000                1005

His Ala Glu Ala Glu Arg Arg Asn Glu Glu Leu Met Lys Lys Phe
    1010                1015                1020

Glu Gly Ala Glu Lys Lys Ile Glu Gln Leu Gln Asp Thr Ala Gln
    1025                1030                1035

Arg Leu Glu Glu Lys Ala Thr Asn Met Glu Ser Glu Asn Lys Val
    1040                1045                1050

Leu Arg Gln Gln Ala Val Ala Ile Ser Pro Thr Ala Lys Ser Leu
    1055                1060                1065

Ala Ala Tyr Pro Lys Ser Pro Phe Gln Leu Arg Thr Pro Glu Asn
    1070                1075                1080

Val Asn Ala Pro Asn Gly Glu Val Lys Ser Ser Pro Asp Val Thr
    1085                1090                1095

Pro Ile Ser Leu Asn Ser Lys Glu Leu Glu Ala Glu Glu Lys Pro
    1100                1105                1110

Gln Lys Ser Leu Asn Glu Lys Gln Gln Glu Asn Gln Asp Leu Leu
    1115                1120                1125

Ile Lys Cys Val Ser Gln Asp Leu Gly Phe Ser Ser Gly Arg Ala
    1130                1135                1140

Ile Ala Ala Cys Val Ile Tyr Arg Cys Leu Leu His Trp Arg Ser
    1145                1150                1155

Phe Glu Val Glu Arg Thr Gly Val Phe Asp Arg Ile Ile Gln Thr
    1160                1165                1170

Ile Gly Thr Ala Ile Glu Ala Gln Asp Asn Asn Asp Lys Leu Ala
    1175                1180                1185

Tyr Trp Leu Ser Asn Ser Ser Thr Leu Leu Leu Leu Gln Arg
    1190                1195                1200

Thr Leu Lys Thr Thr Gly Ala Ala Gly Leu Thr Pro Gln Arg Arg
    1205                1210                1215

Arg Ser Ser Ala Ala Ser Phe Gly Arg Val Phe Ser Gly Ile Arg
    1220                1225                1230

Ala Ser Pro Gln Ser Ala Pro Arg Ala Phe Leu Gly Ser Arg Leu
    1235                1240                1245

Ile Gly Gly Leu Gly Asp Leu Arg Gln Val Glu Ala Lys Tyr Pro
    1250                1255                1260

Ala Leu Leu Phe Lys Gln Gln Leu Thr Ala Phe Leu Glu Lys Ile
    1265                1270                1275

Tyr Gly Met Ile Arg Asp Asn Leu Lys Lys Glu Ile Ser Pro Leu
    1280                1285                1290

Leu Gly Leu Cys Ile Gln Ala Pro Arg Thr Ser Arg Ala Ser Leu
    1295                1300                1305

Ile Lys Gly Ser Arg Ser Gln Ala Asn Ala Leu Ala Gln Gln Thr
    1310                1315                1320

Leu Ile Ala His Trp Gln Ser Ile Val Lys Ile Leu Thr Asn Tyr
    1325                1330                1335

Leu Asn Val Leu Lys Ala Asn Tyr Val Pro Ser Phe Leu Ile Ser
    1340                1345                1350

Lys Val Phe Thr Gln Ile Phe Ser Phe Ile Asn Val Gln Leu Phe
    1355                1360                1365

Asn Ser Leu Leu Leu Arg Arg Glu Cys Cys Ser Phe Ser Asn Gly
    1370                1375                1380

Glu Tyr Val Lys Ala Gly Leu Ala Glu Leu Glu Gln Trp Cys Ile
```

```
                   1385              1390              1395
Tyr Ala Thr Glu Glu Tyr Ala Gly Ser Ser Trp Glu Glu Leu Lys
        1400              1405              1410

His Ile Arg Gln Ala Val Gly Phe Leu Val Ile His Gln Lys Pro
        1415              1420              1425

Lys Lys Thr Leu Lys Glu Ile Thr Asn Asp Leu Cys Pro Val Leu
        1430              1435              1440

Ser Ile Gln Gln Leu Tyr Arg Ile Ser Thr Met Tyr Trp Asp Asp
        1445              1450              1455

Lys Tyr Gly Thr His Thr Val Ser Ser Glu Val Ile Ser Ser Met
        1460              1465              1470

Arg Ile Met Met Thr Glu Asp Ser Asn Asn Ala Val Ser Ser Ser
        1475              1480              1485

Phe Leu Leu Asp Asp Asp Ser Ser Ile Pro Phe Ser Val Asp Asp
        1490              1495              1500

Ile Ser Lys Ser Met Thr Glu Ile Glu Ile Thr Asp Val Asp Met
        1505              1510              1515

Pro Pro Leu Ile Arg Glu Asn Ser Gly Phe Thr Phe Leu His Gln
        1520              1525              1530

Arg Lys Asp
        1535

<210> SEQ ID NO 23
<211> LENGTH: 2214
<212> TYPE: DNA
<213> ORGANISM: Brachypodium distachyon
<220> FEATURE:
<221> NAME/KEY: misc_feature
<223> OTHER INFORMATION: Myosin (Bradi2g41977.1) motor domain

<400> SEQUENCE: 23
atgggtactc cagctaacat cattgttggt tctcatgttt gggtggagga ctcaactcta      60
gcttggatag atggcgaggt tgtcagcata aaaaacaatg aagttcacgt gcagacatca     120
aatgggaaaa aggttactac agacagatca aaagtttttc ccaaggatat ggaagctccg     180
ccaggaggag tggatgatat gacaagatta tcatacttac atgagcctgg tgttctacag     240
aatcttgcta cacgttatga actgaatgaa atatatactt acactggtag catattgatt     300
gcggtaaacc catttcaaag attgccacat ctttacgata cccacatgat ggaacaatac     360
aagggtgcag atttttggaga gttgagtcct cacgtcttcg caattgcaga cgttgcttac     420
agagagatga taaatgaagg gaaaaacaac tctatattgg taagtggtga aagtggtgct     480
ggcaagactg aaacaacaaa gatgcttatg cgatatctag cacacttagg aggacgatct     540
ggagtagagg ggagaacagt agagcaacaa gttctagagt caaacccagt tcttgaagct     600
tttggtaacg caaaaactgt gcgaaataat aactcgagtc gctttggcaa gttcgttgag     660
atccaattcg acaagactgg aaggatctcg ggagctgcta tcagaactta cttgctggaa     720
agatcccgtg tatgccaaat aaatactcca gaaagaaatt atcattgctt ttattttctt     780
tgtgctgcac cacccgagga tactcagagg tataagttgg ctgatgctag atcttttcat     840
tacctcaatc agtcaagttg tattgaggtt gaaggaatta atgatgctga agagtattta     900
gcaacaagaa gggccatgga tatagtagga atcaatgagg aagaacagga agctatattc     960
agggttgtag cagctgtact tcatattgga aacataaaat ttgccaaggg aacagaagta    1020
gattcatctg tgattaagga tgataattcc aggtttcacc ttaacactgc agcagagcta    1080
```

-continued

```
ttagagtgtg attgcaataa tctggaaaag gcactgataa cacgagtaat agttacccct    1140
gaagaaatta ttactagaac acttgatcct gattccgcac ttgctagcag agatgcatta    1200
gcgaaaacag tatattcccg attgtttgat tggattgtgg aaaaaattaa tgtttccatt    1260
ggacaggacc caaactctaa gcaattgatt ggtgttcttg atatttatgg gtttgagagt    1320
ttcaaagtta acagttttga acagttatgc atcaactata caaatgaaaa gcttcagcaa    1380
catttcaacc agcatgtgtt caaaatggag caagaggaat ataccagaga ggagataaac    1440
tggagttaca ttgagtttgt tgacaatcaa gatgtgctag acttgattga agagaaaggt    1500
gggttgattg cacttctgga cgaagcatgt atgtttccca gatcaacgca tgagacattt    1560
gcgcagaagc tgtatacaac tttcaagaat aacaagcgat ttgtcaaacc aaagctttct    1620
cgtacagact ttacagttgt ccattatgct ggcgatgtga cataccaggc tgatcatttc    1680
ttagacaaga acaaagatta tgtagtggct gaacatcagg atctgctgaa tgcttcttca    1740
tgtcctttcg tagctgcttt attcccttca ctccctgaag aatcttcaaa gtcttcaaaa    1800
ttttcctcta ttgggtcacg ttttaagctg cagcttcaat ctctgatgga gaccttgagc    1860
tctacagaac cccattatat tagatgtgtg aagccaaata atctcctcaa gccagccatt    1920
tttgagaaca caaatgtgat acaacaacta cgatgtggag gtgttcttga agctatcagg    1980
ataagctgtg ctgggtaccc cacaagaaaa acgtttatg aatttgttaa tcgctttggt    2040
gttcttggtc ctgaacttct agaaggaagc aacgatgata agattgcatg ccagaagatt    2100
ctggaaaaaa tgaagctgga aaactaccag ataggaaaaa cgaaggtgtt tctgagagct    2160
ggacagatgg ctgatttgga tgcacgaaga gcagaagtgt taggaaaagc agca         2214
```

<210> SEQ ID NO 24
<211> LENGTH: 738
<212> TYPE: PRT
<213> ORGANISM: Brachypodium distachyon
<220> FEATURE:
<221> NAME/KEY: MISC_FEATURE
<223> OTHER INFORMATION: Myosin (Bradi2g41977.1) motor domain

<400> SEQUENCE: 24

```
Met Gly Thr Pro Ala Asn Ile Ile Val Gly Ser His Val Trp Val Glu
1               5                  10                  15

Asp Ser Thr Leu Ala Trp Ile Asp Gly Glu Val Val Ser Ile Lys Asn
            20                  25                  30

Asn Glu Val His Val Gln Thr Ser Asn Gly Lys Lys Val Thr Thr Asp
        35                  40                  45

Arg Ser Lys Val Phe Pro Lys Asp Met Glu Ala Pro Gly Gly Val
    50                  55                  60

Asp Asp Met Thr Arg Leu Ser Tyr Leu His Glu Pro Gly Val Leu Gln
65                  70                  75                  80

Asn Leu Ala Thr Arg Tyr Glu Leu Asn Glu Ile Tyr Thr Tyr Thr Gly
                85                  90                  95

Ser Ile Leu Ile Ala Val Asn Pro Phe Gln Arg Leu Pro His Leu Tyr
            100                 105                 110

Asp Thr His Met Met Glu Gln Tyr Lys Gly Ala Asp Phe Gly Glu Leu
        115                 120                 125

Ser Pro His Val Phe Ala Ile Ala Asp Val Ala Tyr Arg Glu Met Ile
    130                 135                 140

Asn Glu Gly Lys Asn Asn Ser Ile Leu Val Ser Gly Glu Ser Gly Ala
145                 150                 155                 160
```

-continued

Gly Lys Thr Glu Thr Thr Lys Met Leu Met Arg Tyr Leu Ala His Leu
            165                 170                 175
Gly Gly Arg Ser Gly Val Glu Gly Arg Thr Val Glu Gln Gln Val Leu
            180                 185                 190
Glu Ser Asn Pro Val Leu Glu Ala Phe Gly Asn Ala Lys Thr Val Arg
            195                 200                 205
Asn Asn Asn Ser Ser Arg Phe Gly Lys Phe Val Glu Ile Gln Phe Asp
210                 215                 220
Lys Thr Gly Arg Ile Ser Gly Ala Ala Ile Arg Thr Tyr Leu Leu Glu
225                 230                 235                 240
Arg Ser Arg Val Cys Gln Ile Asn Thr Pro Glu Arg Asn Tyr His Cys
            245                 250                 255
Phe Tyr Phe Leu Cys Ala Ala Pro Pro Glu Asp Thr Gln Arg Tyr Lys
            260                 265                 270
Leu Ala Asp Ala Arg Ser Phe His Tyr Leu Asn Gln Ser Ser Cys Ile
            275                 280                 285
Glu Val Glu Gly Ile Asn Asp Ala Glu Glu Tyr Leu Ala Thr Arg Arg
            290                 295                 300
Ala Met Asp Ile Val Gly Ile Asn Glu Glu Gln Glu Ala Ile Phe
305                 310                 315                 320
Arg Val Val Ala Ala Val Leu His Ile Gly Asn Ile Asn Phe Ala Lys
            325                 330                 335
Gly Thr Glu Val Asp Ser Ser Val Ile Lys Asp Asp Asn Ser Arg Phe
            340                 345                 350
His Leu Asn Thr Ala Ala Glu Leu Leu Glu Cys Asp Cys Asn Asn Leu
            355                 360                 365
Glu Lys Ala Leu Ile Thr Arg Val Ile Val Thr Pro Glu Glu Ile Ile
            370                 375                 380
Thr Arg Thr Leu Asp Pro Asp Ser Ala Leu Ala Ser Arg Asp Ala Leu
385                 390                 395                 400
Ala Lys Thr Val Tyr Ser Arg Leu Phe Asp Trp Ile Val Glu Lys Ile
            405                 410                 415
Asn Val Ser Ile Gly Gln Asp Pro Asn Ser Lys Gln Leu Ile Gly Val
            420                 425                 430
Leu Asp Ile Tyr Gly Phe Glu Ser Phe Lys Val Asn Ser Phe Glu Gln
            435                 440                 445
Leu Cys Ile Asn Tyr Thr Asn Glu Lys Leu Gln Gln His Phe Asn Gln
            450                 455                 460
His Val Phe Lys Met Glu Gln Glu Glu Tyr Thr Arg Glu Glu Ile Asn
465                 470                 475                 480
Trp Ser Tyr Ile Glu Phe Val Asp Asn Gln Asp Val Leu Asp Leu Ile
            485                 490                 495
Glu Lys Lys Gly Gly Leu Ile Ala Leu Leu Asp Glu Ala Cys Met Phe
            500                 505                 510
Pro Arg Ser Thr His Glu Thr Phe Ala Gln Lys Leu Tyr Thr Thr Phe
            515                 520                 525
Lys Asn Asn Lys Arg Phe Val Lys Pro Lys Leu Ser Arg Thr Asp Phe
            530                 535                 540
Thr Val Val His Tyr Ala Gly Asp Val Thr Tyr Gln Ala Asp His Phe
545                 550                 555                 560
Leu Asp Lys Asn Lys Asp Tyr Val Val Ala Glu His Gln Asp Leu Leu
            565                 570                 575
Asn Ala Ser Ser Cys Pro Phe Val Ala Ala Leu Phe Pro Ser Leu Pro

```
                    580             585             590
Glu Glu Ser Ser Lys Ser Lys Phe Ser Ser Ile Gly Ser Arg Phe
            595             600             605
Lys Leu Gln Leu Gln Ser Leu Met Glu Thr Leu Ser Ser Thr Glu Pro
    610                 615                 620
His Tyr Ile Arg Cys Val Lys Pro Asn Asn Leu Leu Lys Pro Ala Ile
625                 630                 635                 640
Phe Glu Asn Thr Asn Val Ile Gln Gln Leu Arg Cys Gly Gly Val Leu
                645                 650                 655
Glu Ala Ile Arg Ile Ser Cys Ala Gly Tyr Pro Thr Arg Lys Thr Phe
                660                 665                 670
Tyr Glu Phe Val Asn Arg Phe Gly Val Leu Gly Pro Glu Leu Leu Glu
            675                 680                 685
Gly Ser Asn Asp Asp Lys Ile Ala Cys Gln Lys Ile Leu Glu Lys Met
        690                 695                 700
Lys Leu Glu Asn Tyr Gln Ile Gly Lys Thr Lys Val Phe Leu Arg Ala
705                 710                 715                 720
Gly Gln Met Ala Asp Leu Asp Ala Arg Arg Ala Glu Val Leu Gly Lys
                725                 730                 735
Ala Ala

<210> SEQ ID NO 25
<211> LENGTH: 2214
<212> TYPE: DNA
<213> ORGANISM: Arabidopsis thaliana
<220> FEATURE:
<221> NAME/KEY: misc_feature
<223> OTHER INFORMATION: Myosin XI-2 (MYA2) motor domain

<400> SEQUENCE: 25
atggttgcta acttcaatcc atcagtgggg tcatttgtgt gggtggagga tcctgatgaa      60
gcatggattg atggtgaagt tgtacaagtt aatggtgatg agatcaaagt tctatgcact     120
tcaggaaaac atgttgttac gaaaatctct aatgcttatc ctaaagatgt ggaagcacca     180
gcctctggag tggatgatat gactagactt gcttatttgc atgaacctgg agttctacag     240
aatttgcatt caagatatga tattaacgag atttatactt ataccggaag tatacttatt     300
gctgttaatc cgtttagaag acttcctcat ctttatagta gccatatgat ggctcaaatat    360
aaaggagctt ccttaggaga attgagtcca catccattcg ccgtcgcaga tgctgcgtat     420
agacagatga ttaatgatgg agtaagtcaa tctattctgg ttagtggaga agtggtgct      480
ggtaaaactg aaagcacaaa gttgcttatg agatatcttg cttacatggg agggagagct     540
gctgctgagg aagaagtgtt tgaacagaaa gtgttggagt cgaatcctgt tttagaagca     600
tttggaaatg caaagactgt caggaacaat aattccagtc gctttggtaa gttcgtggag     660
attcagtttg acgaaaaggg aagaatatca ggagctgcca taagaactta tttgttggaa     720
agatcacgag tttgtcaagt ctctgatcct gaaagaaact atcactgttt ctacatgctt     780
tgtgctgctc acaagaaga tgtgaagaaa ttcaagctgg aggaaccaaa gaaatatcac     840
tatctcaatc agtctaaatg tctagagctg atagtataa atgatgcgga ggaatatcat    900
gccacaagac gggcaatgga tgtcgtcggg atcagtacgg aggagcagga tgctattttc     960
agcgtcgtgg cagccattct ccatatcggg aatatcgaat ttgctaaggg ggaagagatt    1020
gattcatcga tacccaaaga tgataaatcc ttgtttcatc tgaaaactgc agctgagctt    1080
ctcagctgcg atgaaaaagc acttgaggat tctctatgca agcgtatcat ggtaactcgt    1140
```

-continued

```
gatgaaacca tcacaaaaac tcttgatcca gaagctgcta ctcttagtag agatgctttg    1200
gctaaagtca tgtactcgag gttatttgac tggcttgttg acaagataaa tagctcaatt    1260
ggtcaagatc atgactcgaa gtacttgatt ggtgttcttg atatttatgg atttgagagt    1320
ttcaagacaa acagttttga gcaattttgc atcaatttga ccaatgaaaa acttcaacag    1380
cattttaatc agcatgtctt taaaatggag caagaagaat ataagaaaga ggaaatcaac    1440
tggagctata tagagttcgt agacaatcaa gatattttag acttaataga aaagaaacca    1500
ggaggtataa ttgctctgct agatgaagct tgcatgtttc ctaggtcaac gcatgaaact    1560
tttgcacaga agctatacca gacattcaaa acccacaagc gctttaccaa gccaaaacta    1620
gctcgtagcg acttcacaat ttgtcattat gctggtgatg tcacttatca gacggaactt    1680
ttcctggaca agaacaaaga ttacgttatt gccgagcatc aggcattgtt aaattcttct    1740
agctgttcct ttgtagcaag tttgttccca ccaatgtctg acgattccaa acaatcaaaa    1800
ttctcatcta taggtacccg tttcaagcaa caattggtat cgttgctcga gattctaaat    1860
accacggagc cgcactatat tcgctgtata aaaccaaata accttctgaa gcctggaatc    1920
tttgagaacg aaaacatttt acaacaatta cgttgtgggg gagtgatgga ggcaataagg    1980
attagttgtg ctggctatcc tactaggaaa catttttgatg agttcttggc cagatttggt    2040
attcttgctc cagaagtgtt ggtaaagaac tctgatgacc ctgctgcttg caagaagctt    2100
ctggacaaag tgggactcga agggtatcag attggcaaga cgaaagtttt tctgcgggct    2160
ggacaaatgg ctgacttgga tacccgaagg actgaggtct tgggaagatc agca          2214
```

<210> SEQ ID NO 26
<211> LENGTH: 738
<212> TYPE: PRT
<213> ORGANISM: Arabidopsis thaliana
<220> FEATURE:
<221> NAME/KEY: MISC_FEATURE
<223> OTHER INFORMATION: Myosin XI-2 (MYA2) motor domain

<400> SEQUENCE: 26

```
Met Val Ala Asn Phe Asn Pro Ser Val Gly Ser Phe Val Trp Val Glu
1               5                   10                  15

Asp Pro Asp Glu Ala Trp Ile Asp Gly Glu Val Val Gln Val Asn Gly
            20                  25                  30

Asp Glu Ile Lys Val Leu Cys Thr Ser Gly Lys His Val Val Thr Lys
        35                  40                  45

Ile Ser Asn Ala Tyr Pro Lys Asp Val Glu Ala Pro Ser Gly Val
    50                  55                  60

Asp Asp Met Thr Arg Leu Ala Tyr Leu His Glu Pro Gly Val Leu Gln
65                  70                  75                  80

Asn Leu His Ser Arg Tyr Asp Ile Asn Glu Ile Tyr Thr Tyr Thr Gly
                85                  90                  95

Ser Ile Leu Ile Ala Val Asn Pro Phe Arg Arg Leu Pro His Leu Tyr
            100                 105                 110

Ser Ser His Met Met Ala Gln Tyr Lys Gly Ala Ser Leu Gly Glu Leu
        115                 120                 125

Ser Pro His Pro Phe Ala Val Ala Asp Ala Ala Tyr Arg Gln Met Ile
    130                 135                 140

Asn Asp Gly Val Ser Gln Ser Ile Leu Val Ser Gly Glu Ser Gly Ala
145                 150                 155                 160

Gly Lys Thr Glu Ser Thr Lys Leu Leu Met Arg Tyr Leu Ala Tyr Met
```

```
                165                 170                 175
Gly Gly Arg Ala Ala Glu Gly Arg Ser Val Glu Gln Lys Val Leu
            180                 185                 190
Glu Ser Asn Pro Val Leu Glu Ala Phe Gly Asn Ala Lys Thr Val Arg
            195                 200                 205
Asn Asn Asn Ser Ser Arg Phe Gly Lys Phe Val Glu Ile Gln Phe Asp
        210                 215                 220
Glu Lys Gly Arg Ile Ser Gly Ala Ala Ile Arg Thr Tyr Leu Leu Glu
225                 230                 235                 240
Arg Ser Arg Val Cys Gln Val Ser Asp Pro Glu Arg Asn Tyr His Cys
                245                 250                 255
Phe Tyr Met Leu Cys Ala Ala Pro Gln Glu Asp Val Lys Lys Phe Lys
                260                 265                 270
Leu Glu Glu Pro Lys Lys Tyr His Tyr Leu Asn Gln Ser Lys Cys Leu
                275                 280                 285
Glu Leu Asp Ser Ile Asn Asp Ala Glu Glu Tyr His Ala Thr Arg Arg
            290                 295                 300
Ala Met Asp Val Val Gly Ile Ser Thr Glu Glu Gln Asp Ala Ile Phe
305                 310                 315                 320
Ser Val Val Ala Ala Ile Leu His Ile Gly Asn Ile Glu Phe Ala Lys
                325                 330                 335
Gly Glu Glu Ile Asp Ser Ser Ile Pro Lys Asp Lys Ser Leu Phe
            340                 345                 350
His Leu Lys Thr Ala Ala Glu Leu Leu Ser Cys Asp Glu Lys Ala Leu
            355                 360                 365
Glu Asp Ser Leu Cys Lys Arg Ile Met Val Thr Arg Asp Glu Thr Ile
        370                 375                 380
Thr Lys Thr Leu Asp Pro Glu Ala Ala Thr Leu Ser Arg Asp Ala Leu
385                 390                 395                 400
Ala Lys Val Met Tyr Ser Arg Leu Phe Asp Trp Leu Val Asp Lys Ile
                405                 410                 415
Asn Ser Ser Ile Gly Gln Asp His Asp Ser Lys Tyr Leu Ile Gly Val
            420                 425                 430
Leu Asp Ile Tyr Gly Phe Glu Ser Phe Lys Thr Asn Ser Phe Glu Gln
        435                 440                 445
Phe Cys Ile Asn Leu Thr Asn Glu Lys Leu Gln Gln His Phe Asn Gln
        450                 455                 460
His Val Phe Lys Met Glu Gln Glu Glu Tyr Lys Lys Glu Glu Ile Asn
465                 470                 475                 480
Trp Ser Tyr Ile Glu Phe Val Asp Asn Gln Asp Ile Leu Asp Leu Ile
                485                 490                 495
Glu Lys Lys Pro Gly Gly Ile Ile Ala Leu Leu Asp Glu Ala Cys Met
            500                 505                 510
Phe Pro Arg Ser Thr His Glu Thr Phe Ala Gln Lys Leu Tyr Gln Thr
            515                 520                 525
Phe Lys Thr His Lys Arg Phe Thr Lys Pro Lys Leu Ala Arg Ser Asp
            530                 535                 540
Phe Thr Ile Cys His Tyr Ala Gly Asp Val Thr Tyr Gln Thr Glu Leu
545                 550                 555                 560
Phe Leu Asp Lys Asn Lys Asp Tyr Val Ile Ala Glu His Gln Ala Leu
                565                 570                 575
Leu Asn Ser Ser Ser Cys Ser Phe Val Ala Ser Leu Phe Pro Pro Met
            580                 585                 590
```

```
Ser Asp Asp Ser Lys Gln Ser Lys Phe Ser Ser Ile Gly Thr Arg Phe
        595                 600                 605

Lys Gln Gln Leu Val Ser Leu Leu Glu Ile Leu Asn Thr Thr Glu Pro
    610                 615                 620

His Tyr Ile Arg Cys Ile Lys Pro Asn Asn Leu Leu Lys Pro Gly Ile
625                 630                 635                 640

Phe Glu Asn Glu Asn Ile Leu Gln Gln Leu Arg Cys Gly Gly Val Met
                645                 650                 655

Glu Ala Ile Arg Ile Ser Cys Ala Gly Tyr Pro Thr Arg Lys His Phe
                660                 665                 670

Asp Glu Phe Leu Ala Arg Phe Gly Ile Leu Ala Pro Glu Val Leu Val
                675                 680                 685

Lys Asn Ser Asp Asp Pro Ala Ala Cys Lys Lys Leu Leu Asp Lys Val
            690                 695                 700

Gly Leu Glu Gly Tyr Gln Ile Gly Lys Thr Lys Val Phe Leu Arg Ala
705                 710                 715                 720

Gly Gln Met Ala Asp Leu Asp Thr Arg Thr Glu Val Leu Gly Arg
                725                 730                 735

Ser Ala
```

<210> SEQ ID NO 27
<211> LENGTH: 2238
<212> TYPE: DNA
<213> ORGANISM: Chara corallina
<220> FEATURE:
<221> NAME/KEY: misc_feature
<223> OTHER INFORMATION: Myosin (CcM) motor domain

<400> SEQUENCE: 27

```
atgggtttgg aaaaggcgag gtcttcggca ctggggattg gctcgccggc gtgggttgaa      60
gatgtggaga ccgtatggat agaagcgacc gtggtgaaac tcgatggcga tgccatcacg     120
gcacggacgg ttaacggcga tctggtggag acgacaatgg cgaatgctct tcccagggat     180
gaagatgtta cgatgcgggg ggttgatgac atgacgaagc tgtcgtattt gcacgagcct     240
ggcgttctgc acaatctcta caccagattc aagcacgatg agatctatac tttcacgggg     300
aatattttga ttgccgtcaa tccttttcaca aggcttccgc accttttcaa cacatacatg     360
atgaagcagt accaggatgc ccagccaggg gatctgaacc ctcatgttta ttctgtggct     420
gatgcggctt ataaagcaat gatggaagag atgaagagcc aggccatttt ggtgagtgga     480
gaaagtggcg ctggtaaaac agagacaaca aaacaaatca tgcagtacct ggctttcgtg     540
ggaggacgga cagtgggtga cgagagatca gttgagcagc aagtactcca gtcaaatcca     600
ttgctcgagg catttggaaa tgcgaagact gtgcggaata caactccag tcgctttggc       660 aagtttgtgg agatccagtt caacaatggg aaaatatctg gcgcggctgt gaggacgtat     720
ttattggaaa ggtcacgtgt cacgcagata tccagtccgg agcgaaacta tcattgcttc     780
tatcagcttg ttgctggtgc atcacctgag gatgcagaac ggttgaagct aggacctcct     840
gactcatttc attacttaaa tcagagcaag tgcgtggaag tcggagctat tgatgattgc     900
aaggagtacc aactcacgcg ggaggcgatg gatattgtgg gcatcactac agaagagcag     960
gaagcaattt ttcgaacaat tgctgctgtt cttcaccttg caacattga atttgattct    1020 ggagaatccg atgcatcaga ggtgtccact gagaagtcaa agtttcactt gaaagcggct    1080
gccgaaatgc tcatgtgcga tgagcaaatg ctggagaagt cgttgacaac acgaatcatg    1140
```

```
aaggcaacac gcactgagag catcacaaag atactgaaca agagccaggc cacagacaac      1200
agagactcca ttgcgaagac aatatatgcg aagctgtttg attggctggt caacaaggtc      1260
aacaagtcta ttggtcagga ccctcactcg actgttctta taggtgttct ggatatctat      1320
ggttttgaga gctttgagat caacagcttt gaacagttct gcatcaatct gacaaacgag      1380
aagctacagc agcatttcaa cacgcatgtg ttcaagatgg agcaagctga atatcggaag      1440
gaagagatca actgggacaa catagacttt gtggataaca ttgacgtgtt agaccttata      1500
gagaagaagc ctctcgggat cattgcactg ttggatgaag catgcatgtt accaagatca      1560
acagctgagt cgtttgcgag gaagctggga gacaccttca ataaccatag aaggttctcg      1620
aagcataagt tcaagagaac agcattcaca atcgatcatt atgcaggaca ggtggaatac      1680
agggcagatc tttttcttgga gaagaataaa gactttgtgg tacccgagca tcagcagctg      1740
cttcatgcat cgagatgtgc atttgtgtca ggactgtttc cagcagatga ggggacaaag      1800
gcaccatcga gtttatgtc cattggtagc caattcaagc tgcaactggc cgctcttatg      1860
gagacattga agctcacagc acctcactac atccgttgtg tgaagccaaa catgcaattg      1920
aagccacaga tcttcgagaa caagaacgtt cttcagcagc ttcgttgtag tggtgtattg      1980
gaggctgtcc gaatcagctg tgcagggttc cctacacgcc gcactttcga ggagttcctt      2040
gataggtttg gattgctgca tcctgaagta ctcatagaaa gtgctgaaga atctgctgat      2100
gagaaagtgg catgccaaaa tctcttggag aagtgcaacc tcaagggcta tcagattggc      2160
aagacaaagg tgttcctacg ggcagggcag atggctattt tggatacact gaggtcaaat      2220
gtgctcaatg aggctgca                                                    2238
```

<210> SEQ ID NO 28
<211> LENGTH: 746
<212> TYPE: PRT
<213> ORGANISM: Chara corallina
<220> FEATURE:
<221> NAME/KEY: MISC_FEATURE
<223> OTHER INFORMATION: Myosin (CcM) motor domain

<400> SEQUENCE: 28

```
Met Gly Leu Glu Lys Ala Arg Ser Ser Ala Leu Gly Ile Gly Ser Pro
1               5                   10                  15

Ala Trp Val Glu Asp Val Glu Thr Val Trp Ile Glu Ala Thr Val Val
            20                  25                  30

Lys Leu Asp Gly Asp Ala Ile Thr Ala Arg Thr Val Asn Gly Asp Leu
        35                  40                  45

Val Glu Thr Thr Met Ala Asn Ala Leu Pro Arg Asp Glu Asp Val Thr
    50                  55                  60

Met Arg Gly Val Asp Asp Met Thr Lys Leu Ser Tyr Leu His Glu Pro
65                  70                  75                  80

Gly Val Leu His Asn Leu Tyr Thr Arg Phe Lys His Asp Glu Ile Tyr
                85                  90                  95

Thr Phe Thr Gly Asn Ile Leu Ile Ala Val Asn Pro Phe Thr Arg Leu
            100                 105                 110

Pro His Leu Phe Asn Thr Tyr Met Met Lys Gln Tyr Gln Asp Ala Gln
        115                 120                 125

Pro Gly Asp Leu Asn Pro His Val Tyr Ser Val Ala Asp Ala Ala Tyr
    130                 135                 140

Lys Ala Met Met Glu Glu Met Lys Ser Gln Ala Ile Leu Val Ser Gly
145                 150                 155                 160
```

-continued

Glu Ser Gly Ala Gly Lys Thr Glu Thr Thr Lys Gln Ile Met Gln Tyr
            165                 170                 175

Leu Ala Phe Val Gly Gly Arg Thr Val Gly Asp Glu Arg Ser Val Glu
        180                 185                 190

Gln Gln Val Leu Gln Ser Asn Pro Leu Leu Glu Ala Phe Gly Asn Ala
        195                 200                 205

Lys Thr Val Arg Asn Asn Ser Ser Arg Phe Gly Lys Phe Val Glu
    210                 215                 220

Ile Gln Phe Asn Asn Gly Lys Ile Ser Gly Ala Ala Val Arg Thr Tyr
225                 230                 235                 240

Leu Leu Glu Arg Ser Arg Val Thr Gln Ile Ser Ser Pro Glu Arg Asn
                245                 250                 255

Tyr His Cys Phe Tyr Gln Leu Val Ala Gly Ala Ser Pro Glu Asp Ala
            260                 265                 270

Glu Arg Leu Lys Leu Gly Pro Pro Asp Ser Phe His Tyr Leu Asn Gln
        275                 280                 285

Ser Lys Cys Val Glu Val Gly Ala Ile Asp Asp Cys Lys Glu Tyr Gln
        290                 295                 300

Leu Thr Arg Glu Ala Met Asp Ile Val Gly Ile Thr Thr Glu Glu Gln
305                 310                 315                 320

Glu Ala Ile Phe Arg Thr Ile Ala Ala Val Leu His Leu Gly Asn Ile
                325                 330                 335

Glu Phe Asp Ser Gly Glu Ser Asp Ala Ser Glu Val Ser Thr Glu Lys
            340                 345                 350

Ser Lys Phe His Leu Lys Ala Ala Ala Glu Met Leu Met Cys Asp Glu
        355                 360                 365

Gln Met Leu Glu Lys Ser Leu Thr Thr Arg Ile Met Lys Ala Thr Arg
    370                 375                 380

Thr Glu Ser Ile Thr Lys Ile Leu Asn Lys Ser Gln Ala Thr Asp Asn
385                 390                 395                 400

Arg Asp Ser Ile Ala Lys Thr Ile Tyr Ala Lys Leu Phe Asp Trp Leu
                405                 410                 415

Val Asn Lys Val Asn Lys Ser Ile Gly Gln Asp Pro His Ser Thr Val
            420                 425                 430

Leu Ile Gly Val Leu Asp Ile Tyr Gly Phe Glu Ser Phe Glu Ile Asn
        435                 440                 445

Ser Phe Glu Gln Phe Cys Ile Asn Leu Thr Asn Glu Lys Leu Gln Gln
    450                 455                 460

His Phe Asn Thr His Val Phe Lys Met Glu Gln Ala Glu Tyr Arg Lys
465                 470                 475                 480

Glu Glu Ile Asn Trp Asp Asn Ile Asp Phe Val Asp Asn Ile Asp Val
                485                 490                 495

Leu Asp Leu Ile Glu Lys Lys Pro Leu Gly Ile Ile Ala Leu Leu Asp
            500                 505                 510

Glu Ala Cys Met Leu Pro Arg Ser Thr Ala Glu Ser Phe Ala Arg Lys
        515                 520                 525

Leu Gly Asp Thr Phe Asn Asn His Arg Arg Phe Ser Lys His Lys Phe
    530                 535                 540

Lys Arg Thr Ala Phe Thr Ile Asp His Tyr Ala Gly Gln Val Glu Tyr
545                 550                 555                 560

Arg Ala Asp Leu Phe Leu Glu Lys Asn Lys Asp Phe Val Val Pro Glu
                565                 570                 575

His Gln Gln Leu Leu His Ala Ser Arg Cys Ala Phe Val Ser Gly Leu

```
                580             585             590
Phe Pro Ala Asp Glu Gly Thr Lys Ala Pro Ser Lys Phe Met Ser Ile
            595                 600             605
Gly Ser Gln Phe Lys Leu Gln Leu Ala Ala Leu Met Glu Thr Leu Lys
        610                 615             620
Leu Thr Ala Pro His Tyr Ile Arg Cys Val Lys Pro Asn Met Gln Leu
625                 630                 635                 640
Lys Pro Gln Ile Phe Glu Asn Lys Asn Val Leu Gln Gln Leu Arg Cys
                645                 650                 655
Ser Gly Val Leu Glu Ala Val Arg Ile Ser Cys Ala Gly Phe Pro Thr
            660                 665                 670
Arg Arg Thr Phe Glu Glu Phe Leu Asp Arg Phe Gly Leu Leu His Pro
        675                 680                 685
Glu Val Leu Ile Glu Ser Ala Glu Ser Ala Asp Glu Lys Val Ala
            690                 695                 700
Cys Gln Asn Leu Leu Glu Lys Cys Asn Leu Lys Gly Tyr Gln Ile Gly
705                 710                 715                 720
Lys Thr Lys Val Phe Leu Arg Ala Gly Gln Met Ala Ile Leu Asp Thr
                725                 730                 735
Leu Arg Ser Asn Val Leu Asn Glu Ala Ala
            740                 745
```

<210> SEQ ID NO 29
<211> LENGTH: 747
<212> TYPE: PRT
<213> ORGANISM: Chara australis
<220> FEATURE:
<221> NAME/KEY: MISC_FEATURE
<223> OTHER INFORMATION: CaM5408 motor domain

<400> SEQUENCE: 29

```
Met Gly Ser Glu Glu Val Arg Ala Pro Gly Gly Ala Thr Ala Val Leu
1               5                   10                  15
Ala Val Gly Ser Pro Val Trp Ile Asp Asp Pro Glu Met Ala Trp Ile
            20                  25                  30
Glu Ala Thr Val Val Lys Ile Asp Gly Ala Val Val Thr Ala Arg Thr
        35                  40                  45
Ile Asn Gly Asp Leu Val Glu Thr Thr Leu Ala Asn Gly Ile Pro Arg
    50                  55                  60
Asp Glu Asp Val Thr Met Arg Gly Val Asp Asp Met Thr Lys Leu Ser
65                  70                  75                  80
Tyr Leu His Glu Pro Gly Val Leu His Asn Leu Tyr Thr Arg Tyr Lys
                85                  90                  95
His Asp Glu Ile Tyr Thr Tyr Thr Gly Asn Ile Leu Ile Ala Val Asn
            100                 105                 110
Pro Phe Thr Arg Leu Pro His Leu Phe Asn Gln Tyr Met Met Lys Gln
        115                 120                 125
Tyr Gln Asp Ala Gln Pro Gly Asp Leu Asn Pro His Ile Tyr Ser Val
    130                 135                 140
Ala Gly Ala Ala Tyr Lys Ala Met Met Glu Glu Asn Lys Ser Gln Ser
145                 150                 155                 160
Ile Leu Val Ser Gly Glu Ser Gly Ala Gly Lys Thr Glu Thr Thr Lys
                165                 170                 175
Gln Ile Met Gln Tyr Leu Ala Phe Val Gly Gly Arg Thr Val Gly Glu
            180                 185                 190
```

-continued

```
Asn Arg Ser Val Glu Arg Gln Val Leu Gln Ser Asn Pro Leu Leu Glu
        195                 200                 205
Ala Phe Gly Asn Ala Lys Thr Val Arg Asn Asn Ser Ser Arg Phe
210                 215                 220
Gly Lys Phe Val Glu Ile Gln Phe Asn Lys Gly Lys Ile Ser Gly Ala
225                 230                 235                 240
Ala Val Arg Thr Tyr Leu Leu Glu Arg Ser Arg Val Thr Gln Ile Ser
                245                 250                 255
Thr Pro Glu Arg Asn Tyr His Cys Phe Tyr Gln Leu Val Ala Gly Ala
                260                 265                 270
Ser Pro Glu Asp Val Glu Arg Leu Lys Leu Gly Pro Pro Glu Ser Phe
            275                 280                 285
His Tyr Leu Asn Gln Ser Lys Cys Val Glu Val Gly Thr Ile Asp Asp
        290                 295                 300
Cys Lys Glu Tyr Gln Leu Thr Arg Glu Ala Met Asp Val Val Gly Ile
305                 310                 315                 320
Gly Ala Glu Glu Gln Ala Ile Phe Arg Thr Ile Ala Gly Val Leu
                325                 330                 335
His Leu Gly Asn Ile Glu Phe Ser Ala Gly Ala Ser Glu Ala Ser Glu
            340                 345                 350
Val Ser Ser Glu Lys Ala Lys Phe His Leu Arg Ala Ala Glu Met
        355                 360                 365
Leu Met Cys Asp Glu Lys Met Leu Glu Lys Ser Leu Thr Thr Arg Ile
        370                 375                 380
Met Arg Ala Ser Arg Thr Glu Ser Ile Thr Lys Ile Leu Asp Thr Ser
385                 390                 395                 400
Gln Ala Thr Asp Asn Arg Asp Ala Leu Ala Arg Thr Ile Tyr Ala Lys
                405                 410                 415
Leu Phe Asp Trp Leu Val Asp Lys Val Asn Lys Ser Ile Gly Gln Asp
                420                 425                 430
Leu His Ser Thr Val Leu Ile Gly Val Leu Asp Ile Tyr Gly Phe Glu
            435                 440                 445
Ser Phe Asp Ile Asn Ser Phe Glu Gln Phe Cys Ile Asn Leu Thr Asn
450                 455                 460
Glu Lys Leu Gln Gln His Phe Asn Thr His Val Phe Lys Met Glu Gln
465                 470                 475                 480
Ala Glu Tyr Arg Lys Glu Glu Ile Asn Trp Asp Ile Asp Phe Val
                485                 490                 495
Asp Asn Ile Asp Val Leu Asp Leu Ile Glu Lys Pro Gly Gly Ile
                500                 505                 510
Ile Ala Leu Leu Asp Glu Ala Cys Met Phe Pro Lys Ser Thr Ala Glu
            515                 520                 525
Ser Phe Ala Ser Lys Leu Gly Ser Thr Phe Gln Ser His Arg Arg Phe
530                 535                 540
Ser Arg Pro Lys Phe Lys Arg Thr Ala Phe Thr Ile Asp His Tyr Ala
545                 550                 555                 560
Gly Gln Val Glu Tyr Arg Ala Asp Leu Phe Leu Glu Lys Asn Lys Asp
                565                 570                 575
Tyr Val Val Pro Glu His Gln Gln Leu Leu His Ala Ser Lys Cys Pro
            580                 585                 590
Phe Val Ala Ala Leu Phe Pro Pro Asp Glu Gly Thr Lys Ala Pro Ser
        595                 600                 605
Lys Phe Ala Ser Ile Gly Ser Gln Phe Arg Leu Gln Leu Ala Ser Leu
```

```
                610             615             620
Met Asp Thr Leu Lys Leu Thr Ala Pro His Tyr Ile Arg Cys Val Lys
625                 630                 635                 640

Pro Asn Met Gln Leu Lys Pro Gln Leu Phe Glu Asn Lys Asn Val Leu
                645                 650                 655

Gln Gln Leu Arg Cys Ser Gly Val Leu Glu Ala Val Arg Ile Ser Cys
                660                 665                 670

Ala Gly Phe Pro Thr Arg Arg Thr Phe Gly Asp Phe Leu Asp Arg Phe
                675                 680                 685

Gly Leu Leu His Pro Glu Val Leu Val Asp Ser Ala Asp Glu Lys Ala
                690                 695                 700

Ala Cys Gln Ile Leu Leu Glu Lys Cys Asn Leu Lys Gly Tyr Gln Ile
705                 710                 715                 720

Gly Lys Thr Lys Val Phe Leu Arg Ala Gly Gln Met Ala Ile Leu Asp
                725                 730                 735

Thr Lys Arg Ser Asn Val Leu Asn Glu Ala Ala
                740                 745

<210> SEQ ID NO 30
<211> LENGTH: 747
<212> TYPE: PRT
<213> ORGANISM: Chara australis
<220> FEATURE:
<221> NAME/KEY: MISC_FEATURE
<223> OTHER INFORMATION: CaM5627 motor domain

<400> SEQUENCE: 30

Met Gly Ser Glu Glu Val Arg Ala Pro Gly Gly Ala Thr Ala Val Leu
1               5                   10                  15

Ala Val Gly Ser Pro Val Trp Ile Asp Asp Pro Glu Met Ala Trp Ile
                20                  25                  30

Glu Ala Thr Val Val Lys Ile Asp Gly Ala Val Val Thr Ala Arg Thr
                35                  40                  45

Ile Asn Gly Asp Leu Val Glu Thr Thr Leu Ala Asn Gly Ile Pro Arg
50                  55                  60

Asp Glu Asp Val Thr Met Arg Gly Val Asp Asp Met Thr Lys Leu Ser
65                  70                  75                  80

Tyr Leu His Glu Pro Gly Val Leu His Asn Leu Tyr Thr Arg Tyr Lys
                85                  90                  95

His Asp Glu Ile Tyr Thr Tyr Thr Gly Asn Ile Leu Ile Ala Val Asn
                100                 105                 110

Pro Phe Thr Arg Leu Pro His Leu Phe Asn Gln Tyr Met Met Lys Gln
                115                 120                 125

Tyr Gln Asp Ala Gln Pro Gly Asp Leu Asn Pro His Ile Tyr Ser Val
130                 135                 140

Ala Gly Ala Ala Tyr Lys Ala Met Met Glu Glu Asn Lys Ser Gln Ser
145                 150                 155                 160

Ile Leu Val Ser Gly Glu Ser Gly Ala Gly Lys Thr Glu Thr Thr Lys
                165                 170                 175

Gln Ile Met Gln Tyr Leu Ala Phe Val Gly Gly Arg Thr Val Gly Glu
                180                 185                 190

Asn Arg Ser Val Glu Arg Gln Val Leu Gln Ser Asn Pro Leu Leu Glu
                195                 200                 205

Ala Phe Gly Asn Ala Lys Thr Val Arg Asn Asn Asn Ser Ser Arg Phe
210                 215                 220
```

```
Gly Lys Phe Val Glu Ile Gln Phe Asn Lys Gly Lys Ile Ser Gly Ala
225                 230                 235                 240

Ala Val Arg Thr Tyr Leu Leu Glu Arg Ser Arg Val Thr Gln Ile Ser
                245                 250                 255

Thr Pro Glu Arg Asn Tyr His Cys Phe Tyr Gln Leu Val Ala Gly Ala
            260                 265                 270

Ser Pro Glu Asp Val Glu Arg Leu Lys Leu Gly Pro Pro Glu Ser Phe
        275                 280                 285

His Tyr Leu Asn Gln Ser Lys Cys Val Glu Val Gly Thr Ile Asp Asp
    290                 295                 300

Cys Lys Glu Tyr Gln Leu Thr Arg Glu Ala Met Asp Val Val Gly Ile
305                 310                 315                 320

Gly Ala Glu Glu Gln Glu Ala Ile Phe Arg Thr Ile Ala Gly Val Leu
                325                 330                 335

His Leu Gly Asn Ile Glu Phe Ser Ala Gly Ala Ser Glu Ala Ser Glu
            340                 345                 350

Val Ser Ser Glu Lys Ala Lys Phe His Leu Arg Ala Ala Ala Glu Met
        355                 360                 365

Leu Met Cys Asp Glu Lys Met Leu Glu Lys Ser Leu Thr Thr Arg Ile
370                 375                 380

Met Arg Ala Ser Arg Thr Glu Ser Ile Thr Lys Ile Leu Asp Thr Ser
385                 390                 395                 400

Gln Ala Thr Asp Asn Arg Asp Ala Leu Ala Arg Thr Ile Tyr Ala Lys
                405                 410                 415

Leu Phe Asp Trp Leu Val Asp Lys Val Asn Lys Ser Ile Gly Gln Asp
            420                 425                 430

Leu His Ser Thr Val Leu Ile Gly Val Leu Asp Ile Tyr Gly Phe Glu
        435                 440                 445

Ser Phe Asp Ile Asn Ser Phe Glu Gln Phe Cys Ile Asn Leu Thr Asn
    450                 455                 460

Glu Lys Leu Gln Gln His Phe Asn Thr His Val Phe Lys Met Glu Gln
465                 470                 475                 480

Ala Glu Tyr Arg Lys Glu Glu Ile Asn Trp Asp Asp Ile Asp Phe Val
                485                 490                 495

Asp Asn Ile Asp Val Leu Asp Leu Ile Glu Lys Pro Gly Gly Ile
            500                 505                 510

Ile Ala Leu Leu Asp Glu Ala Cys Met Phe Pro Lys Ser Thr Ala Glu
        515                 520                 525

Ser Phe Ala Ser Lys Leu Gly Ser Thr Phe Gln Ser His Arg Arg Phe
    530                 535                 540

Ser Arg Pro Lys Phe Lys Arg Thr Ala Phe Thr Ile Asp His Tyr Ala
545                 550                 555                 560

Gly Gln Val Glu Tyr Arg Ala Asp Leu Phe Leu Glu Lys Asn Lys Asp
                565                 570                 575

Tyr Val Val Pro Glu His Gln Gln Leu Leu His Ala Ser Lys Cys Pro
            580                 585                 590

Phe Val Ala Ala Leu Phe Pro Pro Asp Glu Gly Thr Lys Ala Pro Ser
        595                 600                 605

Lys Phe Ala Ser Ile Gly Ser Gln Phe Arg Leu Gln Leu Ala Ser Leu
    610                 615                 620

Met Asp Thr Leu Lys Leu Thr Ala Pro His Tyr Ile Arg Cys Val Lys
625                 630                 635                 640

Pro Asn Met Gln Leu Lys Pro Gln Leu Phe Glu Asn Lys Asn Val Leu
```

```
                        645                 650                 655
Gln Gln Leu Arg Cys Ser Gly Val Leu Glu Ala Val Arg Ile Ser Cys
        660                 665                 670
Ala Gly Phe Pro Thr Arg Arg Thr Phe Gly Asp Phe Leu Asp Arg Phe
        675                 680                 685
Gly Leu Leu His Pro Glu Val Leu Val Asp Ser Ala Asp Glu Lys Ala
        690                 695                 700
Ala Cys Gln Ile Leu Leu Glu Lys Cys Asn Leu Lys Gly Tyr Gln Ile
705                 710                 715                 720
Gly Lys Thr Lys Val Phe Leu Arg Ala Gly Gln Met Ala Ile Leu Asp
                725                 730                 735
Thr Lys Arg Ser Asn Val Leu Asn Glu Ala Ala
                740                 745

<210> SEQ ID NO 31
<211> LENGTH: 650
<212> TYPE: PRT
<213> ORGANISM: Chara braunii
<220> FEATURE:
<221> NAME/KEY: MISC_FEATURE
<223> OTHER INFORMATION: CbM4 motor domain

<400> SEQUENCE: 31

Met Gly Ser Glu Glu Ala Arg Ser Ala Ala Leu Gly Ile Gly Ser Pro
1               5                   10                  15
Val Trp Val Glu Asp Val Glu Asn Ala Trp Ile Glu Ala Thr Val Val
                20                  25                  30
Lys Arg Asp Gly Asp Ala Val Thr Ala Arg Thr Val His Gly Asp Leu
            35                  40                  45
Val Glu Thr Arg Met Ala Asn Ala Leu Pro Arg Asp Glu Asp Val Thr
        50                  55                  60
Met Arg Gly Val Asp Asp Met Thr Lys Leu Ser Tyr Leu His Glu Pro
65                  70                  75                  80
Gly Val Leu His Asn Leu Tyr Ala Arg Tyr Lys His Asp Glu Ile Tyr
                85                  90                  95
Thr Tyr Thr Gly Asn Ile Leu Ile Ala Val Asn Pro Phe Thr Arg Leu
            100                 105                 110
Pro His Leu Phe Asn Thr Tyr Met Met Lys Gln Tyr Gln Asp Ala Gln
        115                 120                 125
Pro Gly Asp Leu Asn Pro His Val Tyr Ser Val Ala Asp Ala Ala Tyr
    130                 135                 140
Lys Ala Met Met Glu Glu Met Lys Ser Gln Ser Ile Leu Val Ser Gly
145                 150                 155                 160
Glu Ser Gly Ala Gly Lys Thr Glu Thr Thr Lys Gln Ile Met Gln Tyr
                165                 170                 175
Leu Ala Phe Val Gly Gly Arg Thr Val Gly Asp Asn Arg Ser Val Glu
            180                 185                 190
Gln Gln Val Leu Gln Ser Asn Pro Leu Leu Glu Ala Phe Gly Asn Ala
        195                 200                 205
Lys Thr Val Arg Asn Asn Asn Ser Ser Arg Phe Gly Lys Phe Val Glu
    210                 215                 220
Ile Gln Phe Asn Asn Gly Lys Ile Ser Gly Ala Ala Val Arg Thr Tyr
225                 230                 235                 240
Leu Leu Glu Arg Ser Arg Val Thr Gln Ile Ser Thr Pro Glu Arg Asn
                245                 250                 255
```

```
Tyr His Cys Phe Tyr Gln Leu Val Ala Gly Ser His Glu Asp Ala
            260                 265                 270

Glu Arg Leu Lys Leu Gly Pro Pro Asp Ser Phe His Tyr Leu Asn Gln
    275                 280                 285

Ser Lys Cys Val Glu Val Gly Ala Ile Asp Asp Cys Lys Glu Tyr Gln
290                 295                 300

Leu Thr Arg Glu Ala Met Asp Ile Val Gly Ile Thr Thr Glu Glu Gln
305                 310                 315                 320

Glu Ala Ile Phe Arg Thr Ile Ala Ala Val Leu His Leu Gly Asn Ile
                325                 330                 335

Glu Phe Asn Ser Gly Glu Ser Glu Ala Ser Glu Val Ser Thr Glu Lys
            340                 345                 350

Ser Lys Phe His Leu Lys Ala Ala Asp Met Leu Met Cys Asp Glu
    355                 360                 365

Glu Met Leu Glu Lys Ser Leu Thr Thr Arg Ile Met Lys Ala Thr Arg
    370                 375                 380

Thr Glu Ser Ile Thr Lys Ile Leu Asn Lys Ser Gln Ala Thr Asp Asn
385                 390                 395                 400

Arg Asp Ala Leu Ala Arg Thr Ile Tyr Ala Lys Leu Phe Asp Trp Leu
                405                 410                 415

Val Asn Lys Val Asn Lys Ser Ile Gly Gln Asp Pro His Ser Thr Val
            420                 425                 430

Leu Ile Gly Val Leu Asp Ile Tyr Gly Phe Glu Ser Phe Glu Ile Asn
        435                 440                 445

Ser Phe Glu Gln Phe Cys Ile Asn Leu Thr Asn Glu Lys Leu Gln Gln
450                 455                 460

His Phe Asn Thr His Val Phe Lys Met Glu Gln Ala Glu Tyr Arg Lys
465                 470                 475                 480

Glu Glu Ile Asn Trp Asp Ile Asp Phe Val Asp Asn Ile Asp Val
                485                 490                 495

Leu Asp Leu Ile Glu Lys Arg Pro Leu Gly Ile Ile Ala Leu Leu Asp
            500                 505                 510

Glu Ala Cys Met Leu Pro Arg Ser Thr Ala Glu Ser Phe Ala Arg Lys
        515                 520                 525

Leu Gly Asp Thr Phe His Asn His Lys Arg Phe Ser Lys His Lys Phe
530                 535                 540

Lys Arg Thr Ala Phe Thr Ile Asp His Tyr Ala Gly Gln Val Glu Tyr
545                 550                 555                 560

Arg Ala Asp Leu Phe Leu Glu Lys Asn Lys Asp Phe Val Val Pro Glu
                565                 570                 575

His Gln Gln Leu Leu His Ala Ser Lys Cys Ala Phe Val Ser Gly Leu
            580                 585                 590

Phe Pro Leu Asp Glu Gly Ala Lys Ala Pro Ser Lys Phe Met Ser Ile
        595                 600                 605

Gly Ser Gln Phe Lys Arg Asn Gly Trp Ile Ser Thr Glu His Cys Val
610                 615                 620

Met Tyr Ala Leu His Gly Arg Phe Thr Ala Leu Ser Met Ser Arg Ser
625                 630                 635                 640

Leu Thr Phe Tyr Phe Ala Phe Phe Val Val
                645                 650

<210> SEQ ID NO 32
<211> LENGTH: 751
<212> TYPE: PRT
```

```
<213> ORGANISM: Chara australis
<220> FEATURE:
<221> NAME/KEY: MISC_FEATURE
<223> OTHER INFORMATION: CaM5639 motor domain

<400> SEQUENCE: 32
```

| | | | | | | | | | | | | | | |
|---|---|---|---|---|---|---|---|---|---|---|---|---|---|---|
| Met | Gly | Ser | Glu | Glu | Val | Arg | Ala | Pro | Gly | Gly | Ala | Thr | Ala | Val | Leu |
| 1 | | | | 5 | | | | | 10 | | | | | 15 | |
| Ala | Val | Gly | Ser | Pro | Val | Trp | Ile | Asp | Asp | Pro | Glu | Met | Ala | Trp | Ile |
| | | | 20 | | | | | 25 | | | | | 30 | | |
| Glu | Ala | Thr | Val | Val | Lys | Ile | Asp | Gly | Ala | Val | Val | Thr | Ala | Arg | Thr |
| | | | 35 | | | | | 40 | | | | | 45 | | |
| Ile | Asn | Gly | Asp | Leu | Val | Glu | Thr | Thr | Leu | Ala | Asn | Gly | Ile | Pro | Arg |
| 50 | | | | | 55 | | | | | 60 | | | | | |
| Asp | Glu | Asp | Val | Thr | Met | Arg | Gly | Val | Asp | Asp | Met | Thr | Lys | Leu | Ser |
| 65 | | | | | 70 | | | | | 75 | | | | | 80 |
| Tyr | Leu | His | Glu | Pro | Gly | Val | Leu | His | Asn | Leu | Tyr | Thr | Arg | Tyr | Lys |
| | | | | 85 | | | | | 90 | | | | | 95 | |
| His | Asp | Glu | Ile | Tyr | Thr | Tyr | Thr | Gly | Asn | Ile | Leu | Ile | Ala | Val | Asn |
| | | | 100 | | | | | 105 | | | | | 110 | | |
| Pro | Phe | Thr | Arg | Leu | Pro | His | Leu | Phe | Asn | Gln | Tyr | Met | Met | Lys | Gln |
| | | | 115 | | | | | 120 | | | | | 125 | | |
| Tyr | Gln | Asp | Ala | Gln | Pro | Gly | Asp | Leu | Asn | Pro | His | Ile | Tyr | Ser | Val |
| 130 | | | | | 135 | | | | | 140 | | | | | |
| Ala | Gly | Ala | Ala | Tyr | Lys | Ala | Met | Met | Glu | Glu | Asn | Lys | Ser | Gln | Ser |
| 145 | | | | | 150 | | | | | 155 | | | | | 160 |
| Ile | Leu | Val | Ser | Gly | Glu | Ser | Gly | Ala | Gly | Lys | Thr | Glu | Thr | Thr | Lys |
| | | | | 165 | | | | | 170 | | | | | 175 | |
| Gln | Ile | Met | Gln | Tyr | Leu | Ala | Phe | Val | Gly | Gly | Arg | Thr | Val | Gly | Asp |
| | | | 180 | | | | | 185 | | | | | 190 | | |
| Glu | Arg | Ser | Val | Glu | Gln | Gln | Val | Leu | Gln | Ser | Asn | Pro | Leu | Leu | Glu |
| | | | 195 | | | | | 200 | | | | | 205 | | |
| Ala | Phe | Gly | Asn | Ala | Lys | Thr | Val | Arg | Asn | Asn | Asn | Ser | Ser | Arg | Phe |
| 210 | | | | | 215 | | | | | 220 | | | | | |
| Gly | Lys | Phe | Val | Glu | Ile | Gln | Phe | Asn | Asn | Gly | Lys | Ile | Ser | Gly | Ala |
| 225 | | | | | 230 | | | | | 235 | | | | | 240 |
| Ala | Val | Arg | Thr | Tyr | Leu | Leu | Glu | Arg | Ser | Arg | Val | Thr | Gln | Ile | Ser |
| | | | | 245 | | | | | 250 | | | | | 255 | |
| Ser | Pro | Glu | Arg | Asn | Tyr | His | Cys | Phe | Tyr | Gln | Leu | Val | Ala | Gly | Ala |
| | | | 260 | | | | | 265 | | | | | 270 | | |
| Ser | Pro | Glu | Asp | Ala | Glu | Arg | Leu | Lys | Leu | Gly | Pro | Pro | Asp | Ser | Phe |
| | | | 275 | | | | | 280 | | | | | 285 | | |
| His | Tyr | Leu | Asn | Gln | Ser | Lys | Cys | Val | Glu | Val | Gly | Ala | Ile | Asp | Asp |
| | | | 290 | | | | | 295 | | | | | 300 | | |
| Cys | Lys | Glu | Tyr | Gln | Leu | Thr | Arg | Glu | Ala | Met | Asp | Ile | Val | Gly | Ile |
| 305 | | | | | 310 | | | | | 315 | | | | | 320 |
| Thr | Thr | Glu | Glu | Gln | Glu | Ala | Ile | Phe | Arg | Thr | Ile | Ala | Ala | Val | Leu |
| | | | | 325 | | | | | 330 | | | | | 335 | |
| His | Leu | Gly | Asn | Ile | Glu | Phe | Asp | Ser | Gly | Glu | Ser | Asp | Ala | Ser | Glu |
| | | | | 340 | | | | | 345 | | | | | 350 | |
| Val | Ser | Thr | Glu | Lys | Ser | Lys | Phe | His | Leu | Lys | Ala | Ala | Ala | Glu | Met |
| | | | 355 | | | | | 360 | | | | | 365 | | |
| Leu | Met | Cys | Asp | Glu | Gln | Met | Leu | Glu | Lys | Ser | Leu | Thr | Thr | Arg | Ile |
| 370 | | | | | 375 | | | | | 380 | | | | | |

Met Lys Ala Thr Arg Thr Glu Ser Ile Thr Lys Ile Leu Asn Lys Ser
385                 390                 395                 400

Gln Ala Thr Asp Asn Arg Asp Ser Ile Ala Lys Thr Ile Tyr Ala Lys
            405                 410                 415

Leu Phe Asp Trp Leu Val Asn Lys Val Asn Lys Ser Ile Gly Gln Asp
        420                 425                 430

Pro His Ser Thr Val Leu Ile Gly Val Leu Asp Ile Tyr Gly Phe Glu
            435                 440                 445

Ser Phe Glu Ile Asn Ser Phe Glu Gln Phe Cys Ile Asn Leu Thr Asn
        450                 455                 460

Glu Lys Leu Gln Gln His Phe Asn Thr His Val Phe Lys Met Glu Gln
465                 470                 475                 480

Ala Glu Tyr Arg Lys Glu Ile Asn Trp Asp Asn Ile Asp Phe Val
            485                 490                 495

Asp Asn Ile Asp Val Leu Asp Leu Ile Glu Lys Pro Leu Gly Ile
            500                 505                 510

Ile Ala Leu Leu Asp Glu Ala Cys Met Leu Pro Arg Ser Thr Ala Glu
        515                 520                 525

Ser Phe Ala Arg Lys Leu Gly Asp Thr Phe Asn Asn His Arg Arg Phe
        530                 535                 540

Ser Lys His Lys Phe Lys Arg Thr Ala Phe Thr Ile Asp His Tyr Ala
545                 550                 555                 560

Gly Gln Val Glu Tyr Arg Ala Asp Leu Phe Leu Glu Lys Asn Lys Asp
            565                 570                 575

Phe Val Val Pro Glu His Gln Gln Leu Leu His Ala Ser Arg Cys Ala
            580                 585                 590

Phe Val Ser Gly Leu Phe Pro Ala Asp Glu Gly Thr Lys Ala Pro Ser
            595                 600                 605

Lys Phe Met Ser Ile Gly Ser Gln Phe Lys Leu Gln Leu Ala Ala Leu
        610                 615                 620

Met Glu Thr Leu Lys Leu Thr Ala Pro His Tyr Ile Arg Cys Val Lys
625                 630                 635                 640

Pro Asn Met Gln Leu Lys Pro Gln Ile Phe Glu Asn Lys Asn Val Leu
            645                 650                 655

Gln Gln Leu Arg Cys Ser Gly Val Leu Glu Ala Val Arg Ile Ser Cys
            660                 665                 670

Ala Gly Phe Pro Thr Arg Arg Thr Phe Glu Glu Phe Leu Asp Arg Phe
        675                 680                 685

Gly Leu Leu Arg Pro Glu Val Leu Ile Glu Ser Ala Glu Glu Ser Ala
        690                 695                 700

Asp Glu Lys Val Ala Cys Gln Asn Leu Leu Lys Cys Asn Leu Lys
705                 710                 715                 720

Gly Tyr Gln Ile Gly Lys Thr Lys Val Phe Leu Arg Ala Gly Gln Met
            725                 730                 735

Ala Ile Leu Asp Thr Leu Arg Ser Asn Val Leu Asn Glu Ala Ala
            740                 745                 750

<210> SEQ ID NO 33
<211> LENGTH: 747
<212> TYPE: PRT
<213> ORGANISM: Chara braunii
<220> FEATURE:
<221> NAME/KEY: MISC_FEATURE
<223> OTHER INFORMATION: CbM3 motor domain

<400> SEQUENCE: 33

```
Met Gly Ser Glu Glu Val Arg Ala Pro Gly Ala Ser Ala Val Leu
1               5                   10                  15

Ala Val Gly Ser Pro Val Trp Ile Glu Asp Pro Glu Lys Ala Trp Ile
            20                  25                  30

Glu Ala Thr Val Val Lys Ile Asp Gly Val Val Thr Ala Arg Thr
            35                  40                  45

Ile Asn Gly Asp Leu Val Glu Thr Thr Leu Ala Asn Gly Ile Pro Arg
50                  55                  60

Asp Glu Asp Val Thr Met Arg Gly Val Asp Asp Met Thr Lys Leu Ser
65                  70                  75                  80

Tyr Leu His Glu Pro Gly Val Leu His Asn Leu Tyr Thr Arg Tyr Lys
                85                  90                  95

His Asp Glu Ile Tyr Thr Tyr Thr Gly Asn Ile Leu Ile Ala Val Asn
                100                 105                 110

Pro Phe Thr Arg Leu Pro His Leu Phe Asn Gln Tyr Met Met Lys Gln
            115                 120                 125

Tyr Gln Asp Ala Gln Pro Gly Asp Leu Asn Pro His Val Tyr Ser Val
130                 135                 140

Ala Gly Ala Ala Tyr Lys Ala Met Met Asp Glu Asn Lys Ser Gln Ser
145                 150                 155                 160

Ile Leu Val Ser Gly Glu Ser Gly Ala Gly Lys Thr Glu Thr Thr Lys
                165                 170                 175

Gln Ile Met Gln Tyr Leu Ala Phe Val Gly Arg Thr Val Gly Asp
                180                 185                 190

Asn Arg Ser Val Glu Arg Gln Val Leu Gln Ser Asn Pro Leu Leu Glu
            195                 200                 205

Ala Phe Gly Asn Ala Lys Thr Val Arg Asn Asn Asn Ser Ser Arg Phe
210                 215                 220

Gly Lys Phe Val Glu Ile Gln Phe Asn Lys Gly Lys Ile Ser Gly Ala
225                 230                 235                 240

Ala Val Arg Thr Tyr Leu Leu Glu Arg Ser Arg Val Thr Gln Ile Ser
                245                 250                 255

Thr Pro Glu Arg Asn Tyr His Cys Phe Tyr Gln Leu Val Ala Gly Ala
            260                 265                 270

Ser Pro Glu Asp Val Glu Arg Leu Lys Leu Gly Pro Pro Glu Ser Phe
    275                 280                 285

His Tyr Leu Asn Gln Ser Lys Cys Val Glu Val Gly Thr Ile Asp Asp
    290                 295                 300

Cys Lys Glu Tyr Gln Leu Thr Arg Glu Ala Met Asp Val Val Gly Ile
305                 310                 315                 320

Gly Ala Glu Glu Gln Glu Ala Ile Phe Arg Thr Ile Ala Ala Val Leu
                325                 330                 335

His Leu Gly Asn Ile Glu Phe Ser Thr Gly Ala Ser Glu Ala Ser Glu
                340                 345                 350

Val Ser Ser Glu Lys Ala Lys Phe His Leu Arg Ala Ala Glu Ile
    355                 360                 365

Leu Met Cys Asp Glu Lys Met Leu Glu Lys Ser Leu Thr Thr Arg Ile
    370                 375                 380

Met Arg Ala Ser Arg Thr Glu Ser Ile Thr Lys Ile Leu Asp Lys Ser
385                 390                 395                 400

Gln Ala Thr Asp Asn Arg Asp Ala Leu Ala Arg Thr Ile Tyr Ala Lys
                405                 410                 415
```

```
Leu Phe Asp Trp Leu Val Asp Lys Val Asn Lys Ser Ile Gly Gln Asp
                420                 425                 430

Leu His Ser Thr Val Leu Ile Gly Val Leu Asp Ile Tyr Gly Phe Glu
            435                 440                 445

Ser Phe Asp Ile Asn Ser Phe Glu Gln Phe Cys Ile Asn Leu Thr Asn
        450                 455                 460

Glu Lys Leu Gln Gln His Phe Asn Thr His Val Phe Lys Met Glu Gln
465                 470                 475                 480

Ala Glu Tyr Arg Lys Glu Ile Asn Trp Asp Ile Asp Phe Val
                485                 490                 495

Asp Asn Ile Asp Val Leu Asp Leu Ile Glu Lys Lys Pro Gly Gly Ile
                500                 505                 510

Ile Ala Leu Leu Asp Glu Ala Cys Met Phe Pro Lys Ser Thr Ala Glu
            515                 520                 525

Ser Phe Ala Ser Lys Leu Gly Ser Thr Phe Gln Ser His Arg Arg Phe
        530                 535                 540

Ser Arg Pro Lys Phe Lys Arg Thr Ala Phe Thr Ile Asp His Tyr Ala
545                 550                 555                 560

Gly Gln Val Glu Tyr Arg Ala Asp Leu Phe Leu Glu Lys Asn Lys Asp
                565                 570                 575

Tyr Val Val Pro Glu His Gln Leu Leu His Ala Ser Lys Cys Pro
                580                 585                 590

Phe Val Ala Ala Leu Phe Pro Pro Asp Glu Gly Thr Lys Ala Pro Ser
                595                 600                 605

Lys Phe Ala Ser Ile Gly Ser Gln Phe Arg Leu Gln Leu Ala Ser Leu
610                 615                 620

Met Asp Thr Leu Lys Leu Thr Ala Pro His Tyr Ile Arg Cys Val Lys
625                 630                 635                 640

Pro Asn Met Gln Leu Lys Pro Gln Ile Phe Glu Asn Lys Asn Val Leu
                645                 650                 655

Gln Gln Leu Arg Cys Ser Gly Val Leu Glu Ala Val Arg Ile Ser Cys
                660                 665                 670

Ala Gly Phe Pro Thr Arg Arg Thr Phe Gly Asp Phe Leu Asp Arg Phe
            675                 680                 685

Gly Leu Leu His Pro Glu Val Leu Val Glu Ser Ala Asp Glu Lys Ala
        690                 695                 700

Ala Cys Gln Ile Leu Leu Glu Lys Cys Asn Leu Lys Gly Tyr Gln Ile
705                 710                 715                 720

Gly Lys Thr Lys Val Phe Leu Arg Ala Gly Gln Met Ala Ile Leu Asp
                725                 730                 735

Thr Lys Arg Ser Asn Val Leu Asn Glu Ala Ala
            740                 745
```

<210> SEQ ID NO 34
<211> LENGTH: 1505
<212> TYPE: PRT
<213> ORGANISM: Arabidopsis thaliana
<220> FEATURE:
<221> NAME/KEY: MISC_FEATURE
<223> OTHER INFORMATION: Full length myosin XI-2 (MYA2)

<400> SEQUENCE: 34

```
Met Val Ala Asn Phe Asn Pro Ser Val Gly Ser Phe Val Trp Val Glu
1               5                   10                  15

Asp Pro Asp Glu Ala Trp Ile Asp Gly Glu Val Val Gln Val Asn Gly
                20                  25                  30
```

```
Asp Glu Ile Lys Val Leu Cys Thr Ser Gly Lys His Val Thr Lys
         35                  40                  45
Ile Ser Asn Ala Tyr Pro Lys Asp Val Glu Ala Pro Ala Ser Gly Val
 50                  55                  60
Asp Asp Met Thr Arg Leu Ala Tyr Leu His Glu Pro Gly Val Leu Gln
 65              70                  75                      80
Asn Leu His Ser Arg Tyr Asp Ile Asn Glu Ile Tyr Thr Tyr Thr Gly
                 85                  90                  95
Ser Ile Leu Ile Ala Val Asn Pro Phe Arg Arg Leu Pro His Leu Tyr
                100                 105                 110
Ser Ser His Met Met Ala Gln Tyr Lys Gly Ala Ser Leu Gly Glu Leu
            115                 120                 125
Ser Pro His Pro Phe Ala Val Ala Asp Ala Ala Tyr Arg Gln Met Ile
            130                 135                 140
Asn Asp Gly Val Ser Gln Ser Ile Leu Val Ser Gly Glu Ser Gly Ala
145                 150                 155                 160
Gly Lys Thr Glu Ser Thr Lys Leu Leu Met Arg Tyr Leu Ala Tyr Met
                165                 170                 175
Gly Gly Arg Ala Ala Glu Gly Arg Ser Val Glu Gln Lys Val Leu
                180                 185                 190
Glu Ser Asn Pro Val Leu Glu Ala Phe Gly Asn Ala Lys Thr Val Arg
                195                 200                 205
Asn Asn Asn Ser Ser Arg Phe Gly Lys Phe Val Glu Ile Gln Phe Asp
210                 215                 220
Glu Lys Gly Arg Ile Ser Gly Ala Ala Ile Arg Thr Tyr Leu Leu Glu
225                 230                 235                 240
Arg Ser Arg Val Cys Gln Val Ser Asp Pro Glu Arg Asn Tyr His Cys
                245                 250                 255
Phe Tyr Met Leu Cys Ala Ala Pro Gln Glu Asp Val Lys Lys Phe Lys
                260                 265                 270
Leu Glu Glu Pro Lys Lys Tyr His Tyr Leu Asn Gln Ser Lys Cys Leu
            275                 280                 285
Glu Leu Asp Ser Ile Asn Asp Ala Glu Glu Tyr His Ala Thr Arg Arg
            290                 295                 300
Ala Met Asp Val Val Gly Ile Ser Thr Glu Glu Gln Asp Ala Ile Phe
305                 310                 315                 320
Ser Val Val Ala Ala Ile Leu His Ile Gly Asn Ile Glu Phe Ala Lys
                325                 330                 335
Gly Glu Glu Ile Asp Ser Ser Ile Pro Lys Asp Lys Ser Leu Phe
                340                 345                 350
His Leu Lys Thr Ala Ala Glu Leu Leu Ser Cys Asp Glu Lys Ala Leu
            355                 360                 365
Glu Asp Ser Leu Cys Lys Arg Ile Met Val Thr Arg Asp Glu Thr Ile
            370                 375                 380
Thr Lys Thr Leu Asp Pro Glu Ala Ala Thr Leu Ser Arg Asp Ala Leu
385                 390                 395                 400
Ala Lys Val Met Tyr Ser Arg Leu Phe Asp Trp Leu Val Asp Lys Ile
                405                 410                 415
Asn Ser Ser Ile Gly Gln Asp His Asp Ser Lys Tyr Leu Ile Gly Val
                420                 425                 430
Leu Asp Ile Tyr Gly Phe Glu Ser Phe Lys Thr Asn Ser Phe Glu Gln
            435                 440                 445
```

-continued

```
Phe Cys Ile Asn Leu Thr Asn Glu Lys Leu Gln Gln His Phe Asn Gln
    450                 455                 460
His Val Phe Lys Met Glu Gln Glu Glu Tyr Lys Lys Glu Glu Ile Asn
465                 470                 475                 480
Trp Ser Tyr Ile Glu Phe Val Asp Asn Gln Asp Ile Leu Asp Leu Ile
                485                 490                 495
Glu Lys Lys Pro Gly Gly Ile Ile Ala Leu Leu Asp Glu Ala Cys Met
                500                 505                 510
Phe Pro Arg Ser Thr His Glu Thr Phe Ala Gln Lys Leu Tyr Gln Thr
        515                 520                 525
Phe Lys Thr His Lys Arg Phe Thr Lys Pro Lys Leu Ala Arg Ser Asp
        530                 535                 540
Phe Thr Ile Cys His Tyr Ala Gly Asp Val Thr Tyr Gln Thr Glu Leu
545                 550                 555                 560
Phe Leu Asp Lys Asn Lys Asp Tyr Val Ile Ala Glu His Gln Ala Leu
                565                 570                 575
Leu Asn Ser Ser Ser Cys Ser Phe Val Ala Ser Leu Phe Pro Pro Met
            580                 585                 590
Ser Asp Asp Ser Lys Gln Ser Lys Phe Ser Ser Ile Gly Thr Arg Phe
        595                 600                 605
Lys Gln Gln Leu Val Ser Leu Leu Glu Ile Leu Asn Thr Thr Glu Pro
610                 615                 620
His Tyr Ile Arg Cys Ile Lys Pro Asn Asn Leu Leu Lys Pro Gly Ile
625                 630                 635                 640
Phe Glu Asn Glu Asn Ile Leu Gln Gln Leu Arg Cys Gly Gly Val Met
                645                 650                 655
Glu Ala Ile Arg Ile Ser Cys Ala Gly Tyr Pro Thr Arg Lys His Phe
                660                 665                 670
Asp Glu Phe Leu Ala Arg Phe Gly Ile Leu Ala Pro Glu Val Leu Val
        675                 680                 685
Lys Asn Ser Asp Asp Pro Ala Ala Cys Lys Lys Leu Leu Asp Lys Val
690                 695                 700
Gly Leu Glu Gly Tyr Gln Ile Gly Lys Thr Lys Val Phe Leu Arg Ala
705                 710                 715                 720
Gly Gln Met Ala Asp Leu Asp Thr Arg Arg Thr Glu Val Leu Gly Arg
                725                 730                 735
Ser Ala Ser Ile Ile Gln Arg Lys Val Arg Ser Tyr Leu Ala Lys Lys
                740                 745                 750
Ser Phe Ile Val Leu Arg Asn Ser Ala Lys Gln Ile Gln Ser Val Cys
        755                 760                 765
Arg Gly Tyr Leu Ala Arg Ser Val Tyr Glu Gly Met Arg Arg Glu Ala
        770                 775                 780
Ala Ala Leu Lys Ile Gln Arg Asp Leu Arg Arg Phe Leu Ala Arg Lys
785                 790                 795                 800
Ala Tyr Thr Glu Leu Tyr Ser Ala Ala Val Ser Val Gln Ala Gly Met
                805                 810                 815
Arg Gly Met Val Ala Arg Lys Glu Leu Cys Phe Arg Arg Gln Thr Lys
                820                 825                 830
Ala Ala Ile Ile Ile Gln Thr Trp Cys Arg Gly Tyr Leu Ala Arg Leu
                835                 840                 845
His Tyr Arg Lys Leu Lys Ala Ala Ile Thr Thr Gln Cys Ala Trp
850                 855                 860
Arg Ser Lys Val Ala Arg Gly Glu Leu Arg Lys Leu Lys Met Ala Ala
```

```
                865                 870                 875                 880
Arg Glu Thr Gly Ala Leu Gln Ala Ala Lys Asn Lys Leu Glu Lys Gln
                    885                 890                 895
Val Glu Glu Leu Thr Trp Arg Leu Gln Leu Glu Lys Arg Ile Arg Thr
                    900                 905                 910
Asp Leu Glu Glu Ala Lys Lys Gln Glu Ser Ala Lys Ala Gln Ser Ser
                    915                 920                 925
Leu Glu Glu Leu Gln Leu Lys Cys Lys Glu Thr Glu Ala Leu Leu Ile
                    930                 935                 940
Lys Glu Arg Glu Ala Ala Lys Lys Ile Ala Glu Thr Ala Pro Ile Ile
945                 950                 955                 960
Lys Glu Ile Pro Val Val Asp Gln Glu Leu Met Asp Lys Ile Thr Asn
                    965                 970                 975
Glu Asn Glu Lys Leu Lys Ser Met Val Ser Ser Leu Glu Met Lys Ile
                    980                 985                 990
Gly Glu Thr Glu Lys Lys Leu Gln Glu Thr Thr Lys Ile Ser Gln Asp
                    995                 1000                1005
Arg Leu Asn Gln Ala Leu Glu Ala Glu Ser Lys Leu Val Lys Leu
        1010                1015                1020
Lys Thr Ala Met Gln Arg Leu Glu Glu Lys Ile Leu Asp Met Glu
        1025                1030                1035
Ala Glu Lys Lys Ile Met His Gln Gln Thr Ile Ser Thr Pro Val
        1040                1045                1050
Arg Thr Asn Leu Gly His Pro Pro Thr Ala Pro Val Lys Asn Leu
        1055                1060                1065
Glu Asn Gly His Gln Thr Asn Leu Glu Lys Glu Phe Asn Glu Ala
        1070                1075                1080
Glu Phe Thr Thr Pro Val Asp Gly Lys Ala Gly Lys Ser Ala Ala
        1085                1090                1095
Glu Arg Gln Ile Met Asn Val Asp Ala Leu Ile Asp Cys Val Lys
        1100                1105                1110
Asp Asn Ile Gly Phe Ser Asn Gly Lys Pro Val Ala Ala Phe Thr
        1115                1120                1125
Ile Tyr Lys Cys Leu Leu His Trp Lys Cys Phe Glu Ser Glu Lys
        1130                1135                1140
Thr Asn Val Phe Asp Arg Leu Ile Gln Met Ile Gly Ser Ala Ile
        1145                1150                1155
Glu Asn Glu Asp Asp Asn Ser His Leu Ala Tyr Trp Leu Thr Ser
        1160                1165                1170
Thr Ser Ala Leu Leu Phe Leu Leu Gln Lys Ser Leu Lys Thr Asn
        1175                1180                1185
Gly Ser Gly Ala Thr Gln Ser Lys Lys Pro Pro Ala Ser Thr Ser
        1190                1195                1200
Leu Phe Gly Arg Met Ala Met Ser Phe Arg Ser Ser Pro Ala Ser
        1205                1210                1215
Gly Asn Leu Ala Ala Ala Ala Glu Ala Ala Ala Leu Ala Val Val
        1220                1225                1230
Arg Pro Val Glu Ala Lys Tyr Pro Ala Leu Leu Phe Lys Gln Gln
        1235                1240                1245
Leu Ala Ala Tyr Val Glu Lys Met Phe Gly Met Val Arg Asp Asn
        1250                1255                1260
Leu Lys Arg Glu Leu Ser Thr Leu Leu Ser Leu Cys Ile Gln Ala
        1265                1270                1275
```

```
Pro Arg Ser Ser Lys Gly Gly Met Leu Arg Ser Gly Arg Ser Phe
    1280            1285                1290
Gly Lys Asp Ser Pro Ala Val His Trp Gln Ser Ile Ile Asp Gly
    1295            1300                1305
Leu Asn Ser Leu Leu Val Thr Leu Lys Glu Asn His Val Pro Leu
    1310            1315                1320
Val Leu Ile Gln Lys Ile Tyr Ser Gln Thr Phe Ser Tyr Ile Asn
    1325            1330                1335
Val Gln Leu Phe Asn Ser Leu Leu Arg Lys Glu Cys Cys Thr
    1340            1345                1350
Phe Ser Asn Gly Glu Phe Val Lys Ser Gly Leu Ala Glu Leu Glu
    1355            1360                1365
Leu Trp Cys Cys Gln Ala Lys Glu Tyr Ser Gly Pro Ser Trp Glu
    1370            1375                1380
Glu Leu Lys His Ile Arg Gln Ala Val Gly Phe Leu Val Ile His
    1385            1390                1395
Gln Lys Tyr Arg Ile Ser Tyr Asp Glu Ile Ala Asn Asp Leu Cys
    1400            1405                1410
Pro Val Leu Ser Val Gln Gln Leu Tyr Arg Ile Cys Thr Leu Tyr
    1415            1420                1425
Trp Asp Asp Ser Tyr Asn Thr Arg Ser Val Ser Gln Glu Val Ile
    1430            1435                1440
Ser Ser Met Arg Thr Leu Met Thr Glu Glu Ser Asn Asp Ala Asp
    1445            1450                1455
Ser Asp Ser Phe Leu Leu Asp Asp Asp Ser Ser Ile Pro Phe Ser
    1460            1465                1470
Ile Asp Asp Ile Ser Ser Ser Met Glu Glu Lys Asp Phe Val Gly
    1475            1480                1485
Ile Lys Pro Ala Glu Glu Leu Leu Glu Asn Pro Ala Phe Val Phe
    1490            1495                1500
Leu His
    1505

<210> SEQ ID NO 35
<211> LENGTH: 2311
<212> TYPE: DNA
<213> ORGANISM: Arabidopsis thaliana
<220> FEATURE:
<221> NAME/KEY: misc_feature
<223> OTHER INFORMATION: Neck domain & Tail domain

<400> SEQUENCE: 35
atcagcaagc attattcaga gaaaagttcg gtcatatctc gctaaaaaga gtttcatcgt      60
tctgcgtaat tctgctaaac agattcagtc agtttgcaga ggttatctcg ctagaagtgt     120
atatgaaggc atgcgtaggg aagctgctgc tttaaaaatc agagagact tgcgtaggtt      180 tctggctagg aaggcttaca cagagctata ttctgctgct gtttcggttc aagctggtat     240
gcgtggtatg gttgcccgga agaactatg ttttagaaga caaaccaaag ctgcaataat     300
aattcagact tggtgccgtg atacctggc tcgcctgcat tacagaaaac taagaaaagc     360
agctatcacg acccaatgtg catggagatc aaaagtggct cgtggagaac ttcgaaagct     420
taagatggct gctagagaaa ctggagcact ccaagcagcc aagaacaagc tagaaagca     480 agttgaagag ctgacctgga gattgcagtt agagaaacgg ataaggactg acctggaaga    540
ggccaaaaaa caagaaagtg caaaagcaca gtcttctttg gaggaattgc aactgaagtg     600
```

```
caaagaaacg gaggcattgc ttattaaaga acgtgaagct gccaagaaga ttgctgagac    660
tgccccgatt attaaggaga ttcctgtggt tgatcaggaa ttaatggata agatcacgaa    720
tgaaaatgaa aagctgaaga gtatggtgag ttcactggaa atgaaaatcg gtgagacaga    780
gaaaaaactt caagagacca ccaagattag ccaggataga ctaaatcaag cattggaggc    840
tgaatctaaa ctagtgaagt tgaagactgc aatgcagagg cttgaagaga aaatattaga    900
tatggaagct gagaagaaaa ttatgcatca gcaaacaata agcactcctg tgaggacaaa    960
tctaggacat cctccaactg cacctgttaa gaatttggaa atggccacc aaacgaactt    1020 ggaaaaggag ttcaatgaag ccgagtttac aacaccagtt gatggcaagg ctgggaaatc    1080
tgctgcagaa cgtcaaatta tgaatgttga tgctctcatt gactgtgtaa aagacaacat    1140
cggtttcagt aatggaaaac ctgtggctgc atttacaatt tacaagtgtc tacttcactg    1200
gaagtgtttc gaatctgaga agactaatgt gtttgatcgt ctgattcaga tgattggttc    1260
cgcgattgag aatgaggatg acaatagtca cttggcgtat tggttgacaa gcacatcggc    1320
actactattt ttgcttcaaa aaagtcttaa aaccaatggc agcggagcaa cacaaagcaa    1380
gaagccacct gcttcaactt ctttatttgg aaggatggcc atgagcttcc gctcttcacc    1440
cgcttcaggc aaccttgctg ctgcagctga agctgctgct cttgcagtgg tccgcccagt    1500
ggaggcaaag tacccggctc tgcttttcaa gcaacagctt gcagcctatg ttgagaaaat    1560
gtttgggatg gttagggata acttgaagag agagttatca actttacttt ctctatgcat    1620
tcaggcaccc agatcttcta aaggagggat gctaagatct ggcaggtcct ttggaaaaga    1680
ttctcctgca gttcactggc aaagcattat cgacggtctt aattcgcttc ttgtcacact    1740
gaaagaaaat catgttcctt tagtactcat ccagaagata tactctcaaa ctttctcata    1800
cattaacgta caacttttca acagtctcct tctgcgtaaa gagtgctgta catttagcaa    1860
tggtgaattt gtaaaatccg ggcttgcgga gctagagcta tggtgttgtc aagccaaaga    1920
atattctggg ccgtcttggg aagaactgaa acatattaga caagccgttg ggttcttggt    1980
tatccaccag aaatacagaa tctcatacga tgaaatagca aacgatcttt gcccggtcct    2040
cagtgtccag cagctttacc gtatttgcac cttatactgg gacgatagct ataacacccg    2100
aagcgtctca caagaagtga tatcgagtat gcggacactc atgacagagg aatccaatga    2160
tgcagacagt gattccttct tgttggatga tgattccagc attcctttct caatcgatga    2220
tatttcaagt tcgatggaag agaaggattt tgtaggaatc aaaccagcag aagaacttct    2280
tgaaaatcca gcatttgtat tcttgcacta a                                  2311
```

<210> SEQ ID NO 36
<211> LENGTH: 19
<212> TYPE: PRT
<213> ORGANISM: Chara braunii
<220> FEATURE:
<221> NAME/KEY: MISC_FEATURE
<223> OTHER INFORMATION: Loop 2 sequence 1

<400> SEQUENCE: 36

Glu Glu Pro Lys Gln Gly Gly Lys Gly Gly Lys Ser Ser Phe Ser
1               5                   10                  15

Ser Ile Gly

<210> SEQ ID NO 37
<211> LENGTH: 20
<212> TYPE: PRT

<213> ORGANISM: Chara braunii
<220> FEATURE:
<221> NAME/KEY: MISC_FEATURE
<223> OTHER INFORMATION: Loop 2 sequence 2

<400> SEQUENCE: 37

Glu Glu Pro Lys Gln Gly Gly Gly Lys Gly Gly Ser Lys Ser Ser Phe
1               5                   10                  15

Ser Ser Ile Gly
            20

<210> SEQ ID NO 38
<211> LENGTH: 4518
<212> TYPE: DNA
<213> ORGANISM: Arabidopsis thaliana

<400> SEQUENCE: 38

| | |
|---|---|
| atggttgcta acttcaatcc atcagtgggg tcatttgtgt gggtggagga tcctgatgaa | 60 |
| gcatggattg atggtgaagt tgtacaagtt aatggtgatg agatcaaagt tctatgcact | 120 |
| tcaggaaaac atgttgttac gaaaatctct aatgcttatc ctaaagatgt ggaagcacca | 180 |
| gcctctggag tggatgatat gactagactt gcttatttgc atgaacctgg agttctacag | 240 |
| aatttgcatt caagatatga tattaacgag atttatactt atacaggaag tatacttatt | 300 |
| gctgttaatc cgtttagaag acttcctcat ctttatagta gccatatgat ggctcaatat | 360 |
| aaaggagctt ccttaggaga attgagtcca catccattcg ccgtcgcaga tgctgcgtat | 420 |
| agacagatga ttaatgatgg agtaagtcaa tctattctgg ttagtggaga agtggtgct | 480 |
| ggtaaaactg aaagcacaaa gttgcttatg agatatcttg cttacatggg agggagagct | 540 |
| gctgctgagg aagaagtgt tgaacagaaa gtgttggagt cgaatcctgt tttagaagca | 600 |
| tttggaaatg caaagactgt caggaacaat aattccagtc gctttggtaa gttcgtggag | 660 |
| attcagtttg acgaaaaggg aagaatatca ggagctgcca taagaactta tttgttggaa | 720 |
| agatcacgag tttgtcaagt ctctgatcct gaaagaaact atcactgttt ctacatgctt | 780 |
| tgtgctgctc acaagaaga tgtgaagaaa ttcaagctgg aggaaccaaa gaaatatcac | 840 |
| tatctcaatc agtctaaatg tctagagctg atagtataa atgatgcgga ggaatatcat | 900 |
| gccacaagac gggcaatgga tgtcgtcggg atcagtacgg aggagcagga tgctattttc | 960 |
| agcgtcgtgg cagccattct ccatatcggg aatatcgaat ttgctaaggg ggaagagatt | 1020 |
| gattcatcga tacccaaaga tgataaatcc ttgtttcatc tgaaaactgc agctgagctt | 1080 |
| ctcagctgcg atgaaaaagc acttgaggat tctctatgca agcgtatcat ggtaactcgt | 1140 |
| gatgaaacca tcacaaaaac tcttgatcca gaagctgcta ctcttagtag agatgctttg | 1200 |
| gctaaagtca tgtactcgag gttatttgac tggcttgttg acaagataaa tagctcaatt | 1260 |
| ggtcaagatc atgactcgaa gtacttgatt ggtgttcttg atatttatgg atttgagagt | 1320 |
| tcaagacaa acagttttga gcaatttgc atcaatttga ccaatgaaaa acttcaacag | 1380 |
| cattttaatc agcatgtctt taaaatggag caagaagaat ataagaaaga ggaaatcaac | 1440 |
| tggagctata tagagttcgt agacaatcaa gatattttag acttaataga aaagaaacca | 1500 |
| ggaggtataa ttgctctgct agatgaagct tgcatgtttc ctaggtcaac gcatgaaact | 1560 |
| tttgcacaga agctatacca gacattcaaa acccacaagc gctttaccaa gccaaaacta | 1620 |
| gctcgtagcg acttcacaat ttgtcattat gctggtgatg tcacttatca gacgaaactt | 1680 |
| ttcctggaca agaacaaaga ttacgttatt gccgagcatc aggcattgtt aaattcttct | 1740 |

```
agctgttcct tgtagcaag tttgttccca ccaatgtctg acgattccaa acaatcaaaa    1800
ttctcatcta taggtacccg tttcaagcaa caattggtat cgttgctcga gattctaaat    1860
accacggagc cgcactatat tcgctgtata aaaccaaata accttctgaa gcctggaatc    1920
tttgagaacg aaaacatttt acaacaatta cgttgtgggg gagtgatgga ggcaataagg    1980
attagttgtg ctggctatcc tactaggaaa cattttgatg agttcttggc cagatttggt    2040
attcttgctc cagaagtgtt ggtaaagaac tctgatgacc ctgctgcttg caagaagctt    2100
ctggacaaag tgggactcga agggtatcag attggcaaga cgaaagtttt tctgcgggct    2160
ggacaaatgg ctgacttgga tacccgaagg actgaggtct gggaagatc agcaagcatt    2220 attcagagaa aagttcggtc atatctcgct aaaaagagtt tcatcgttct gcgtaattct    2280
gctaaacaga ttcagtcagt ttgcagaggt tatctcgcta aagtgtata tgaaggcatg    2340 cgtagggaag ctgctgcttt aaaaatccag agagacttgc gtaggtttct ggctaggaag    2400
gcttacacag agctatattc tgctgctgtt tcggttcaag ctggtatgcg tggtatggtt    2460
gcccggaaag aactatgttt tagaagacaa accaaagctg caataataat tcagacttgg    2520
tgccgtggat acctggctcg cctgcattac agaaaactaa agaaagcagc tatcacgacc    2580 caatgtcat ggagatcaaa agtggctcgt ggagaacttc gaaagcttaa gatggctgct    2640
agagaaactg gagcactcca agcagccaag aacaagctag agaagcaagt tgaagagctg    2700
acctggagat tgcagttaga gaaacggata aggactgacc tggaagaggc caaaaaacaa    2760
gaaagtgcaa agcacagtc ttctttggag gaattgcaac tgaagtgcaa agaaacggag    2820
gcattgctta ttaaagaacg tgaagctgcc aagaagattg ctgagactgc cccgattatt    2880
aaggagattc ctgtggttga tcaggaatta atggataaga tcacgaatga aaatgaaaag    2940
ctgaagagta tggtgagttc actggaaatg aaaatcggtg agacagagaa aaaacttcaa    3000
gagaccacca agattagcca ggatagacta aatcaagcat tggaggctga atctaaacta    3060
gtgaagttga agactgcaat gcagaggctt gaagagaaaa tattagatat ggaagctgag    3120
aagaaaatta tgcatcagca aacaataagc actcctgtga ggacaaatct aggacatcct    3180
ccaactgcac ctgttaagaa tttggaaaat ggccaccaaa cgaacttgga aaaggagttc    3240
aatgaagccg agtttacaac accagttgat ggcaaggctg ggaaatctgc tgcagaacgt    3300
caaattatga atgttgatgc tctcattgac tgtgtaaaag acaacatcgg tttcagtaat    3360
ggaaaacctg tggctgcatt tacaatttac aagtgtctac ttcactggaa gtgtttcgaa    3420
tctgagaaga ctaatgtgtt tgatcgtctg attcagatga ttggttccgc gattgagaat    3480
gaggatgaca atagtcactt ggcgtattgg ttgacaagca catcggcact actatttttg    3540
cttcaaaaaa gtcttaaaac caatggcagc ggagcaacac aaagcaagaa gccacctgct    3600
tcaacttctt tatttggaag gatggccatg agcttccgct cttcacccgc ttcaggcaac    3660
cttgctgctg cagctgaagc tgctgctctt gcagtggtcc gcccagtgga ggcaaagtac    3720
ccggctctgc ttttcaagca acagcttgca gcctatgttg agaaaatgtt tgggatggtt    3780
agggataact tgaagagaga gttatcaact ttactttctc tatgcattca ggcacccaga    3840
tcttctaaag gagggatgct aagatctggc aggtcctttg gaaagagattc tcctgcagtt    3900 cactggcaaa gcattatcga cggtcttaat tcgcttcttg tcacactgaa agaaaatcat    3960
gttcctttag tactcatcca gaagatatac tctcaaactt tctcatacat taacgtacaa    4020
cttttcaaca gtctccttct gcgtaaagag tgctgtacat ttagcaatgg tgaatttgta    4080
aaatccgggc ttgcggagct agagctatgg tgttgtcaag ccaaagaata ttctgggccg    4140
```

-continued

```
tcttgggaag aactgaaaca tattagacaa gccgttgggt tcttggttat ccaccagaaa    4200
tacagaatct catacgatga aatagcaaac gatctttgcc cggtcctcag tgtccagcag    4260
ctttaccgta tttgcacctt atactgggac gatagctata cacccgaag cgtctcacaa     4320 gaagtgatat cgagtatgcg gacactcatg acagaggaat ccaatgatgc agacagtgat    4380
tccttcttgt tggatgatga ttccagcatt cctttctcaa tcgatgatat ttcaagttcg    4440
atggaagaga aggattttgt aggaatcaaa ccagcagaag aacttcttga aaatccagca    4500
tttgtattct tgcactaa                                                  4518
```

<210> SEQ ID NO 39
<211> LENGTH: 1505
<212> TYPE: PRT
<213> ORGANISM: Arabidopsis thaliana

<400> SEQUENCE: 39

```
Met Val Ala Asn Phe Asn Pro Ser Val Gly Ser Phe Val Trp Val Glu
1               5                   10                  15

Asp Pro Asp Glu Ala Trp Ile Asp Gly Glu Val Val Gln Val Asn Gly
            20                  25                  30

Asp Glu Ile Lys Val Leu Cys Thr Ser Gly Lys His Val Val Thr Lys
        35                  40                  45

Ile Ser Asn Ala Tyr Pro Lys Asp Val Glu Ala Pro Ala Ser Gly Val
    50                  55                  60

Asp Asp Met Thr Arg Leu Ala Tyr Leu His Glu Pro Gly Val Leu Gln
65                  70                  75                  80

Asn Leu His Ser Arg Tyr Asp Ile Asn Glu Ile Tyr Thr Tyr Thr Gly
                85                  90                  95

Ser Ile Leu Ile Ala Val Asn Pro Phe Arg Arg Leu Pro His Leu Tyr
            100                 105                 110

Ser Ser His Met Met Ala Gln Tyr Lys Gly Ala Ser Leu Gly Glu Leu
        115                 120                 125

Ser Pro His Pro Phe Ala Val Ala Asp Ala Ala Tyr Arg Gln Met Ile
    130                 135                 140

Asn Asp Gly Val Ser Gln Ser Ile Leu Val Ser Gly Glu Ser Gly Ala
145                 150                 155                 160

Gly Lys Thr Glu Ser Thr Lys Leu Leu Met Arg Tyr Leu Ala Tyr Met
                165                 170                 175

Gly Gly Arg Ala Ala Ala Glu Gly Arg Ser Val Glu Gln Lys Val Leu
            180                 185                 190

Glu Ser Asn Pro Val Leu Glu Ala Phe Gly Asn Ala Lys Thr Val Arg
        195                 200                 205

Asn Asn Asn Ser Ser Arg Phe Gly Lys Phe Val Glu Ile Gln Phe Asp
    210                 215                 220

Glu Lys Gly Arg Ile Ser Gly Ala Ala Ile Arg Thr Tyr Leu Leu Glu
225                 230                 235                 240

Arg Ser Arg Val Cys Gln Val Ser Asp Pro Glu Arg Asn Tyr His Cys
                245                 250                 255

Phe Tyr Met Leu Cys Ala Ala Pro Gln Glu Asp Val Lys Lys Phe Lys
            260                 265                 270

Leu Glu Glu Pro Lys Lys Tyr His Tyr Leu Asn Gln Ser Lys Cys Leu
        275                 280                 285

Glu Leu Asp Ser Ile Asn Asp Ala Glu Glu Tyr His Ala Thr Arg Arg
    290                 295                 300
```

-continued

```
Ala Met Asp Val Val Gly Ile Ser Thr Glu Glu Gln Asp Ala Ile Phe
305                 310                 315                 320

Ser Val Val Ala Ala Ile Leu His Ile Gly Asn Ile Glu Phe Ala Lys
                325                 330                 335

Gly Glu Glu Ile Asp Ser Ser Ile Pro Lys Asp Asp Lys Ser Leu Phe
            340                 345                 350

His Leu Lys Thr Ala Ala Glu Leu Leu Ser Cys Asp Glu Lys Ala Leu
        355                 360                 365

Glu Asp Ser Leu Cys Lys Arg Ile Met Val Thr Arg Asp Glu Thr Ile
370                 375                 380

Thr Lys Thr Leu Asp Pro Glu Ala Ala Thr Leu Ser Arg Asp Ala Leu
385                 390                 395                 400

Ala Lys Val Met Tyr Ser Arg Leu Phe Asp Trp Leu Asp Lys Ile
                405                 410                 415

Asn Ser Ser Ile Gly Gln Asp His Asp Ser Lys Tyr Leu Ile Gly Val
                420                 425                 430

Leu Asp Ile Tyr Gly Phe Glu Ser Phe Lys Thr Asn Ser Phe Glu Gln
        435                 440                 445

Phe Cys Ile Asn Leu Thr Asn Glu Lys Leu Gln Gln His Phe Asn Gln
    450                 455                 460

His Val Phe Lys Met Glu Gln Glu Tyr Lys Lys Glu Glu Ile Asn
465                 470                 475                 480

Trp Ser Tyr Ile Glu Phe Val Asp Asn Gln Asp Ile Leu Asp Leu Ile
                485                 490                 495

Glu Lys Lys Pro Gly Gly Ile Ile Ala Leu Leu Asp Glu Ala Cys Met
            500                 505                 510

Phe Pro Arg Ser Thr His Glu Thr Phe Ala Gln Lys Leu Tyr Gln Thr
        515                 520                 525

Phe Lys Thr His Lys Arg Phe Thr Lys Pro Lys Leu Ala Arg Ser Asp
    530                 535                 540

Phe Thr Ile Cys His Tyr Ala Gly Asp Val Thr Tyr Gln Thr Glu Leu
545                 550                 555                 560

Phe Leu Asp Lys Asn Lys Asp Tyr Val Ile Ala Glu His Gln Ala Leu
                565                 570                 575

Leu Asn Ser Ser Ser Cys Ser Phe Val Ala Ser Leu Phe Pro Pro Met
            580                 585                 590

Ser Asp Asp Ser Lys Gln Ser Lys Phe Ser Ser Ile Gly Thr Arg Phe
        595                 600                 605

Lys Gln Gln Leu Val Ser Leu Leu Glu Ile Leu Asn Thr Thr Glu Pro
    610                 615                 620

His Tyr Ile Arg Cys Ile Lys Pro Asn Asn Leu Leu Lys Pro Gly Ile
625                 630                 635                 640

Phe Glu Asn Glu Asn Ile Leu Gln Gln Leu Arg Cys Gly Gly Val Met
                645                 650                 655

Glu Ala Ile Arg Ile Ser Cys Ala Gly Tyr Pro Thr Arg Lys His Phe
            660                 665                 670

Asp Glu Phe Leu Ala Arg Phe Gly Ile Leu Ala Pro Glu Val Leu Val
        675                 680                 685

Lys Asn Ser Asp Asp Pro Ala Ala Cys Lys Lys Leu Leu Asp Lys Val
    690                 695                 700

Gly Leu Glu Gly Tyr Gln Ile Gly Lys Thr Lys Val Phe Leu Arg Ala
705                 710                 715                 720
```

```
Gly Gln Met Ala Asp Leu Asp Thr Arg Arg Thr Glu Val Leu Gly Arg
            725                 730                 735

Ser Ala Ser Ile Ile Gln Arg Lys Val Arg Ser Tyr Leu Ala Lys Lys
            740                 745                 750

Ser Phe Ile Val Leu Arg Asn Ser Ala Lys Gln Ile Gln Ser Val Cys
            755                 760                 765

Arg Gly Tyr Leu Ala Arg Ser Val Tyr Glu Gly Met Arg Arg Glu Ala
            770                 775                 780

Ala Ala Leu Lys Ile Gln Arg Asp Leu Arg Arg Phe Leu Ala Arg Lys
785                 790                 795                 800

Ala Tyr Thr Glu Leu Tyr Ser Ala Ala Val Ser Val Gln Ala Gly Met
                805                 810                 815

Arg Gly Met Val Ala Arg Lys Glu Leu Cys Phe Arg Arg Gln Thr Lys
            820                 825                 830

Ala Ala Ile Ile Ile Gln Thr Trp Cys Arg Gly Tyr Leu Ala Arg Leu
            835                 840                 845

His Tyr Arg Lys Leu Lys Lys Ala Ala Ile Thr Thr Gln Cys Ala Trp
            850                 855                 860

Arg Ser Lys Val Ala Arg Gly Glu Leu Arg Lys Leu Lys Met Ala Ala
865                 870                 875                 880

Arg Glu Thr Gly Ala Leu Gln Ala Ala Lys Asn Lys Leu Glu Lys Gln
                885                 890                 895

Val Glu Glu Leu Thr Trp Arg Leu Gln Leu Glu Lys Arg Ile Arg Thr
            900                 905                 910

Asp Leu Glu Glu Ala Lys Lys Gln Glu Ser Ala Lys Ala Gln Ser Ser
            915                 920                 925

Leu Glu Glu Leu Gln Leu Lys Cys Lys Glu Thr Glu Ala Leu Leu Ile
            930                 935                 940

Lys Glu Arg Glu Ala Ala Lys Lys Ile Ala Glu Thr Ala Pro Ile Ile
945                 950                 955                 960

Lys Glu Ile Pro Val Val Asp Gln Glu Leu Met Asp Lys Ile Thr Asn
                965                 970                 975

Glu Asn Glu Lys Leu Lys Ser Met Val Ser Ser Leu Glu Met Lys Ile
            980                 985                 990

Gly Glu Thr Glu Lys Lys Leu Gln  Glu Thr Thr Lys Ile  Ser Gln Asp
            995                 1000                1005

Arg Leu  Asn Gln Ala Leu Glu  Ala Glu Ser Lys Leu  Val Lys Leu
            1010                1015                1020

Lys Thr  Ala Met Gln Arg Leu  Glu Glu Lys Ile Leu  Asp Met Glu
            1025                1030                1035

Ala Glu  Lys Lys Ile Met His  Gln Gln Thr Ile Ser  Thr Pro Val
            1040                1045                1050

Arg Thr  Asn Leu Gly His Pro  Pro Thr Ala Pro Val  Lys Asn Leu
            1055                1060                1065

Glu Asn  Gly His Gln Thr Asn  Leu Glu Lys Glu Phe  Asn Glu Ala
            1070                1075                1080

Glu Phe  Thr Thr Pro Val Asp  Gly Lys Ala Gly Lys  Ser Ala Ala
            1085                1090                1095

Glu Arg  Gln Ile Met Asn Val  Asp Ala Leu Ile Asp  Cys Val Lys
            1100                1105                1110

Asp Asn  Ile Gly Phe Ser Asn  Gly Lys Pro Val Ala  Ala Phe Thr
            1115                1120                1125

Ile Tyr  Lys Cys Leu Leu His  Trp Lys Cys Phe Glu  Ser Glu Lys
```

|   |   |   |   |   |   |   |   |   |   |   |   |
|---|---|---|---|---|---|---|---|---|---|---|---|
|  | 1130 |  |  |  | 1135 |  |  |  | 1140 |  |  |
| Thr | Asn | Val | Phe | Asp | Arg | Leu | Ile | Gln | Met | Ile | Gly | Ser | Ala | Ile |
|  | 1145 |  |  |  | 1150 |  |  |  | 1155 |  |  |
| Glu | Asn | Glu | Asp | Asn | Ser | His | Leu | Ala | Tyr | Trp | Leu | Thr | Ser |
|  | 1160 |  |  |  | 1165 |  |  |  | 1170 |  |  |
| Thr | Ser | Ala | Leu | Leu | Phe | Leu | Leu | Gln | Lys | Ser | Leu | Lys | Thr | Asn |
|  | 1175 |  |  |  | 1180 |  |  |  | 1185 |  |  |
| Gly | Ser | Gly | Ala | Thr | Gln | Ser | Lys | Lys | Pro | Pro | Ala | Ser | Thr | Ser |
|  | 1190 |  |  |  | 1195 |  |  |  | 1200 |  |  |
| Leu | Phe | Gly | Arg | Met | Ala | Met | Ser | Phe | Arg | Ser | Ser | Pro | Ala | Ser |
|  | 1205 |  |  |  | 1210 |  |  |  | 1215 |  |  |
| Gly | Asn | Leu | Ala | Ala | Ala | Ala | Glu | Ala | Ala | Ala | Leu | Ala | Val | Val |
|  | 1220 |  |  |  | 1225 |  |  |  | 1230 |  |  |
| Arg | Pro | Val | Glu | Ala | Lys | Tyr | Pro | Ala | Leu | Leu | Phe | Lys | Gln | Gln |
|  | 1235 |  |  |  | 1240 |  |  |  | 1245 |  |  |
| Leu | Ala | Ala | Tyr | Val | Glu | Lys | Met | Phe | Gly | Met | Val | Arg | Asp | Asn |
|  | 1250 |  |  |  | 1255 |  |  |  | 1260 |  |  |
| Leu | Lys | Arg | Glu | Leu | Ser | Thr | Leu | Leu | Ser | Leu | Cys | Ile | Gln | Ala |
|  | 1265 |  |  |  | 1270 |  |  |  | 1275 |  |  |
| Pro | Arg | Ser | Ser | Lys | Gly | Gly | Met | Leu | Arg | Ser | Gly | Arg | Ser | Phe |
|  | 1280 |  |  |  | 1285 |  |  |  | 1290 |  |  |
| Gly | Lys | Asp | Ser | Pro | Ala | Val | His | Trp | Gln | Ser | Ile | Ile | Asp | Gly |
|  | 1295 |  |  |  | 1300 |  |  |  | 1305 |  |  |
| Leu | Asn | Ser | Leu | Leu | Val | Thr | Leu | Lys | Glu | Asn | His | Val | Pro | Leu |
|  | 1310 |  |  |  | 1315 |  |  |  | 1320 |  |  |
| Val | Leu | Ile | Gln | Lys | Ile | Tyr | Ser | Gln | Thr | Phe | Ser | Tyr | Ile | Asn |
|  | 1325 |  |  |  | 1330 |  |  |  | 1335 |  |  |
| Val | Gln | Leu | Phe | Asn | Ser | Leu | Leu | Leu | Arg | Lys | Glu | Cys | Cys | Thr |
|  | 1340 |  |  |  | 1345 |  |  |  | 1350 |  |  |
| Phe | Ser | Asn | Gly | Glu | Phe | Val | Lys | Ser | Gly | Leu | Ala | Glu | Leu | Glu |
|  | 1355 |  |  |  | 1360 |  |  |  | 1365 |  |  |
| Leu | Trp | Cys | Cys | Gln | Ala | Lys | Glu | Tyr | Ser | Gly | Pro | Ser | Trp | Glu |
|  | 1370 |  |  |  | 1375 |  |  |  | 1380 |  |  |
| Glu | Leu | Lys | His | Ile | Arg | Gln | Ala | Val | Gly | Phe | Leu | Val | Ile | His |
|  | 1385 |  |  |  | 1390 |  |  |  | 1395 |  |  |
| Gln | Lys | Tyr | Arg | Ile | Ser | Tyr | Asp | Glu | Ile | Ala | Asn | Asp | Leu | Cys |
|  | 1400 |  |  |  | 1405 |  |  |  | 1410 |  |  |
| Pro | Val | Leu | Ser | Val | Gln | Gln | Leu | Tyr | Arg | Ile | Cys | Thr | Leu | Tyr |
|  | 1415 |  |  |  | 1420 |  |  |  | 1425 |  |  |
| Trp | Asp | Asp | Ser | Tyr | Asn | Thr | Arg | Ser | Val | Ser | Gln | Glu | Val | Ile |
|  | 1430 |  |  |  | 1435 |  |  |  | 1440 |  |  |
| Ser | Ser | Met | Arg | Thr | Leu | Met | Thr | Glu | Glu | Ser | Asn | Asp | Ala | Asp |
|  | 1445 |  |  |  | 1450 |  |  |  | 1455 |  |  |
| Ser | Asp | Ser | Phe | Leu | Leu | Asp | Asp | Asp | Ser | Ser | Ile | Pro | Phe | Ser |
|  | 1460 |  |  |  | 1465 |  |  |  | 1470 |  |  |
| Ile | Asp | Asp | Ile | Ser | Ser | Ser | Met | Glu | Glu | Lys | Asp | Phe | Val | Gly |
|  | 1475 |  |  |  | 1480 |  |  |  | 1485 |  |  |
| Ile | Lys | Pro | Ala | Glu | Glu | Leu | Leu | Glu | Asn | Pro | Ala | Phe | Val | Phe |
|  | 1490 |  |  |  | 1495 |  |  |  | 1500 |  |  |
| Leu | His |
|  | 1505 |

<210> SEQ ID NO 40

<211> LENGTH: 4539
<212> TYPE: DNA
<213> ORGANISM: Artificial Sequence
<220> FEATURE:
<223> OTHER INFORMATION: Chimera protein: Myosin XI in which the motor
      domain of myosin XI-B (Arabidopsis thaliana) is substituted with
      myosin XI of CbM 1 (Chara braunni)

<400> SEQUENCE: 40

| | | | | | |
|---|---|---|---|---|---|
| atggcaacgt | ttggagtcgg | ttccccagtg | tgggttgaag | atgaagagga | tatgtggatt | 60 |
| gaggcaacgg | tgctcaagat | cgaggcagat | aaggtcattt | cgaagaacag | gaaaggtggc | 120 |
| gaggttgttt | cgtctaagga | tatggtccat | ccgagagacg | aggacacggc | tgaaatgggt | 180 |
| gttgacgaca | tgacgaggtt | gtcgtacctc | cacgagcctg | gagtattgga | caatctttcc | 240 |
| cgaagatacc | acctcaatca | aatttataca | tacacaggga | gcatttgtat | cgccatcaat | 300 |
| cctttccaag | cagtgccaca | tttggttgga | accaaactca | tggaaatgtt | caaggttgca | 360 |
| cagcctggag | aggtcagcca | acctcacgtg | tatgcagtgg | ctgacagagc | ttacaaggct | 420 |
| atgatggatg | aggaaaagag | tcagtcaatt | cttgtcagtg | gagaaagtgg | tgcgggtaag | 480 |
| acagaagcga | caaagcttat | catgaactac | cttgccttta | tgggagggag | ggccactccc | 540 |
| gttgcaggag | aaagatcagt | ggagcagaag | gtgttggagt | caaatccact | gctggaagcc | 600 |
| ttcggaaatg | caaagacagt | ccgtaacaac | aattccagtc | gcttcggtaa | attcgtggag | 660 |
| atccagttca | acagaggcaa | gatttctggg | gctgcagttc | gaacctatct | gctggagcga | 720 |
| tctcgtatca | ctcaagtgtc | gacacctgag | cgtagttacc | attgtttcta | ccagctatgt | 780 |
| gcgggagcca | cagcagagga | gagagaaaag | ctgaagatcg | aagctgctcc | aaactacttc | 840 |
| tacctcaatc | agagcgagtg | ttttgaggtt | cctcgatttg | atgaagtaga | agagtacaag | 900 |
| gcaactcgac | atgccatgga | tgttgtgggt | atctccactg | aggagcagga | tggtattttc | 960 |
| cgaatcgttg | catcaattct | tcatcttgga | aatgttgact | caaaccagg | caaggaggca | 1020 |
| gactcctcac | aacttgcaga | tgacaagtcc | cgatttcacc | tcaactgctg | tgcggagttg | 1080 |
| ctgggagcga | acccaaagct | tctggaagat | tcactcatcc | aaagaatcat | ggttacgagg | 1140 |
| ggagaagcca | tcaccaagct | actggacaag | aaacaggctg | ttggaagtcg | tgatgctctc | 1200 |
| gcaaaaactc | tctatgccaa | gatgttcgac | tggttggtcg | acaaggtcaa | caagtccatt | 1260 |
| ggtcaagatc | ccaactccaa | cactctggtt | ggtgtgcttg | atatttatgg | ctttgagagc | 1320 |
| ttcacggtga | acagtttcga | gcagctttgc | atcaatctca | caaatgaaaa | gctgcagcag | 1380 |
| cacttcaaca | cgcatgtctt | caagatggag | caagaggagt | acgtgaagga | agagatcaac | 1440 |
| tgggacaaca | ttgactttgt | tgataacata | gatgttctgg | accttatcga | gaagaaacca | 1500 |
| ttgggaatca | ttgctttgct | cgatgaagcc | tgcatgttgc | ccaaatccac | accggagtca | 1560 |
| tttggccaaa | agcttgctca | gtcttttgac | aagcacaaac | gatttacaaa | gcacaagttc | 1620 |
| aagaagacac | tgttcaaaat | tgaccacttt | gcaggagagg | tggagtactc | gacggacaca | 1680 |
| tttattgaaa | agaacaagga | tttcgtgatt | gcggagcatc | agcaactgct | gacagcgtcc | 1740 |
| acagatccat | tgtgtgagaca | ggtgtatccg | ccaccagagg | agccaaagca | gggcggaaag | 1800 |
| ggtgagggga | agtcatcctt | ctcctctatt | ggaactcgtt | tcaagcaaca | actgcaatct | 1860 |
| ctgatggaca | cccttaacca | gacagagccg | cattatgtcc | gttgcgtgaa | gcccaaccag | 1920 |
| aaactgaagc | cactcatgtt | cgagaagcgg | attgtcctcc | agcagcttcg | gtgcagtggt | 1980 |
| gtgttggaag | ctgtgcgtat | cagttgtgct | ggtttcccaa | caaggcgtac | attcttcgag | 2040 |
| tttgcagaca | gattcaagat | tttgtttccc | gatgcagttg | ccaactgtgg | ccaggactat | 2100 |

```
aagagcgcat gtgtcaagat cctggagaag attgggctcg agaggtatca gattggaaaa    2160
accaaggtgt ttttgcgagc aggccagatg gctattctgg atacaaaacg taccgagatt    2220
ctcggaagat cagcaagcat tattcagaga aaagttcggt catatctcgc taaaaagagt    2280
ttcatcgttc tgcgtaattc tgctaaacag attcagtcag tttgcagagg ttatctcgct    2340
agaagtgtat atgaaggcat gcgtagggaa gctgctgctt taaaaatcca gagagacttg    2400
cgtaggtttc tggctaggaa ggcttacaca gagctatatt ctgctgctgt ttcggttcaa    2460
gctggtatgc gtggtatggt tgcccggaaa gaactatgtt ttagaagaca aaccaaagct    2520
gcaataataa ttcagacttg gtgccgtgga tacctggctc gcctgcatta cagaaaacta    2580
aagaaagcag ctatcacgac ccaatgtgca tggagatcaa agtggctcg tggagaactt     2640 cgaaagctta agatggctgc tagagaaact ggagcactcc aagcagccaa gaacaagcta    2700
gagaagcaag ttgaagagct gacctggaga ttgcagttag agaaacggat aaggactgac    2760
ctggaagagg ccaaaaaaca agaaagtgca aaagcacagt cttctttgga ggaattgcaa    2820
ctgaagtgca agaaacgga ggcattgctt attaaagaac gtgaagctgc caagaagatt      2880
gctgagactc ccccgattat taaggagatt cctgtggttg atcaggaatt aatggataag    2940
atcacgaatg aaaatgaaaa gctgaagagt atggtgagtt cactggaaat gaaaatcggt    3000
gagacagaga aaaacttca agagaccacc aagattagcc aggatagact aaatcaagca     3060
ttggaggctg aatctaaact agtgaagttg aagactgcaa tgcagaggct tgaagagaaa    3120
atattagata tggaagctga gaagaaaatt atgcatcagc aaacaataag cactcctgtg    3180
aggacaaatc taggacatcc tccaactgca cctgttaaga atttggaaaa tggccaccaa    3240
acgaacttgg aaaaggagtt caatgaagcc gagtttacaa caccagttga tggcaaggct    3300
gggaaatctg ctgcagaacg tcaaattatg aatgttgatg ctctcattga ctgtgtaaaa    3360
gacaacatcg gtttcagtaa tggaaaacct gtggctgcat ttacaattta caagtgtcta    3420
cttcactgga agtgtttcga atctgagaag actaatgtgt ttgatcgtct gattcagatg    3480
attggttccg cgattgagaa tgaggatgac aatagtcact tggcgtattg gttgacaagc    3540
acatcggcac tactatttt gcttcaaaaa agtcttaaaa ccaatggcag cggagcaaca    3600
caaagcaaga agccacctgc ttcaacttct ttatttggaa ggatggccat gagcttccgc    3660
tcttcacccg cttcaggcaa ccttgctgct gcagctgaag ctgctgctct tgcagtggtc    3720
cgcccagtgg aggcaaagta cccggctctg cttttcaagc aacagcttgc agcctatgtt    3780
gagaaaatgt ttgggatggt tagggataac ttgaagagag agttatcaac tttactttct    3840
ctatgcattc aggcacccag atcttctaaa ggagggatgc taagatctgg caggtccttt    3900
ggaaaagatt ctcctgcagt tcactggcaa agcattatcg acggtcttaa ttcgcttctt    3960
gtcacactga agaaaatca tgttcctta gtactcatcc agaagatata ctctcaaact       4020
ttctcataca ttaacgtaca acttttcaac agtctccttc tgcgtaaaga gtgctgtaca    4080
tttagcaatg gtgaatttgt aaaatccggg cttgcggagc tagagctatg gtgttgtcaa    4140
gccaaagaat attctgggcc gtctgggaa gaactgaaac atattagaca agccgttggg      4200
ttcttggtta tccaccagaa atacagaatc tcatacgatg aaatagcaaa cgatctttgc    4260
ccggtcctca gtgtccagca gctttaccgt atttgcacct tatactggga cgatagctat    4320
aacacccgaa gcgtctcaca agaagtgata tcgagtatgc ggacactcat gacagaggaa    4380
tccaatgatg cagacagtga ttccttcttg ttggatgatg attccagcat tccttttctca    4440
```

```
atcgatgata tttcaagttc gatggaagag aaggatttg taggaatcaa accagcagaa      4500
gaacttcttg aaaatccagc atttgtattc ttgcactaa                            4539
```

<210> SEQ ID NO 41
<211> LENGTH: 1512
<212> TYPE: PRT
<213> ORGANISM: Artificial Sequence
<220> FEATURE:
<223> OTHER INFORMATION: Chimera protein: Myosin XI in which the motor
      domain of myosin XI-B (Arabidopsis thaliana) is substituted with
      myosin XI of CbM 1 (Chara braunni)

<400> SEQUENCE: 41

```
Met Ala Thr Phe Gly Val Gly Ser Pro Val Trp Val Glu Asp Glu Glu
1               5                   10                  15

Asp Met Trp Ile Glu Ala Thr Val Leu Lys Ile Glu Ala Asp Lys Val
            20                  25                  30

Ile Ser Lys Asn Arg Lys Gly Gly Glu Val Val Ser Ser Lys Asp Met
        35                  40                  45

Val His Pro Arg Asp Glu Asp Thr Ala Glu Met Gly Val Asp Asp Met
    50                  55                  60

Thr Arg Leu Ser Tyr Leu His Glu Pro Gly Val Leu Asp Asn Leu Ser
65                  70                  75                  80

Arg Arg Tyr His Leu Asn Gln Ile Tyr Thr Tyr Thr Gly Ser Ile Cys
                85                  90                  95

Ile Ala Ile Asn Pro Phe Gln Ala Val Pro His Leu Val Gly Thr Lys
            100                 105                 110

Leu Met Glu Met Phe Lys Val Ala Gln Pro Gly Glu Val Ser Gln Pro
        115                 120                 125

His Val Tyr Ala Val Ala Asp Arg Ala Tyr Lys Ala Met Met Asp Glu
    130                 135                 140

Glu Lys Ser Gln Ser Ile Leu Val Ser Gly Ser Gly Ala Gly Lys
145                 150                 155                 160

Thr Glu Ala Thr Lys Leu Ile Met Asn Tyr Leu Ala Phe Met Gly Gly
                165                 170                 175

Arg Ala Thr Pro Val Ala Gly Glu Arg Ser Val Glu Gln Lys Val Leu
            180                 185                 190

Glu Ser Asn Pro Leu Leu Glu Ala Phe Gly Asn Ala Lys Thr Val Arg
        195                 200                 205

Asn Asn Asn Ser Ser Arg Phe Gly Lys Phe Val Glu Ile Gln Phe Asn
    210                 215                 220

Arg Gly Lys Ile Ser Gly Ala Ala Val Arg Thr Tyr Leu Leu Glu Arg
225                 230                 235                 240

Ser Arg Ile Thr Gln Val Ser Thr Pro Glu Arg Ser Tyr His Cys Phe
                245                 250                 255

Tyr Gln Leu Cys Ala Gly Ala Thr Ala Glu Glu Arg Glu Lys Leu Lys
            260                 265                 270

Ile Glu Ala Ala Pro Asn Tyr Phe Tyr Leu Asn Gln Ser Glu Cys Phe
        275                 280                 285

Glu Val Pro Arg Phe Asp Glu Val Glu Tyr Lys Ala Thr Arg His
    290                 295                 300

Ala Met Asp Val Val Gly Ile Ser Thr Glu Glu Gln Asp Gly Ile Phe
305                 310                 315                 320

Arg Ile Val Ala Ser Ile Leu His Leu Gly Asn Val Asp Phe Lys Pro
                325                 330                 335
```

```
Gly Lys Glu Ala Asp Ser Ser Gln Leu Ala Asp Lys Ser Arg Phe
            340                 345                 350

His Leu Asn Cys Cys Ala Glu Leu Leu Gly Ala Asn Pro Lys Leu Leu
        355                 360                 365

Glu Asp Ser Leu Ile Gln Arg Ile Met Val Thr Arg Gly Glu Ala Ile
    370                 375                 380

Thr Lys Leu Leu Asp Lys Lys Gln Ala Val Gly Ser Arg Asp Ala Leu
385                 390                 395                 400

Ala Lys Thr Leu Tyr Ala Lys Met Phe Asp Trp Leu Val Asp Lys Val
                405                 410                 415

Asn Lys Ser Ile Gly Gln Asp Pro Asn Ser Asn Thr Leu Val Gly Val
            420                 425                 430

Leu Asp Ile Tyr Gly Phe Glu Ser Phe Thr Val Asn Ser Phe Glu Gln
        435                 440                 445

Leu Cys Ile Asn Leu Thr Asn Glu Lys Leu Gln Gln His Phe Asn Thr
    450                 455                 460

His Val Phe Lys Met Glu Gln Glu Glu Tyr Val Lys Glu Glu Ile Asn
465                 470                 475                 480

Trp Asp Asn Ile Asp Phe Val Asp Asn Ile Asp Val Leu Asp Leu Ile
                485                 490                 495

Glu Lys Lys Pro Leu Gly Ile Ile Ala Leu Leu Asp Glu Ala Cys Met
            500                 505                 510

Leu Pro Lys Ser Thr Pro Glu Ser Phe Gly Gln Lys Leu Ala Gln Ser
        515                 520                 525

Phe Asp Lys His Lys Arg Phe Thr Lys His Lys Phe Lys Lys Thr Leu
    530                 535                 540

Phe Lys Ile Asp His Phe Ala Gly Glu Val Glu Tyr Ser Thr Asp Thr
545                 550                 555                 560

Phe Ile Glu Lys Asn Lys Asp Phe Val Ile Ala Glu His Gln Gln Leu
                565                 570                 575

Leu Thr Ala Ser Thr Asp Pro Phe Val Arg Gln Val Tyr Pro Pro Pro
            580                 585                 590

Glu Glu Pro Lys Gln Gly Gly Lys Gly Gly Lys Ser Ser Phe Ser
        595                 600                 605

Ser Ile Gly Thr Arg Phe Lys Gln Gln Leu Gln Ser Leu Met Asp Thr
    610                 615                 620

Leu Asn Gln Thr Glu Pro His Tyr Val Arg Cys Val Lys Pro Asn Gln
625                 630                 635                 640

Lys Leu Lys Pro Leu Met Phe Glu Lys Arg Ile Val Leu Gln Gln Leu
                645                 650                 655

Arg Cys Ser Gly Val Leu Glu Ala Val Arg Ile Ser Cys Ala Gly Phe
            660                 665                 670

Pro Thr Arg Arg Thr Phe Phe Glu Phe Ala Asp Arg Phe Lys Ile Leu
        675                 680                 685

Phe Pro Asp Ala Val Ala Asn Cys Gly Gln Asp Tyr Lys Ser Ala Cys
    690                 695                 700

Val Lys Ile Leu Glu Lys Ile Gly Leu Glu Arg Tyr Gln Ile Gly Lys
705                 710                 715                 720

Thr Lys Val Phe Leu Arg Ala Gly Gln Met Ala Ile Leu Asp Thr Lys
                725                 730                 735

Arg Thr Glu Ile Leu Gly Arg Ser Ala Ser Ile Ile Gln Arg Lys Val
            740                 745                 750

Arg Ser Tyr Leu Ala Lys Lys Ser Phe Ile Val Leu Arg Asn Ser Ala
```

755                 760                 765
Lys Gln Ile Gln Ser Val Cys Arg Gly Tyr Leu Ala Arg Ser Val Tyr
770                 775                 780

Glu Gly Met Arg Arg Glu Ala Ala Leu Lys Ile Gln Arg Asp Leu
785                 790                 795                 800

Arg Arg Phe Leu Ala Arg Lys Ala Tyr Thr Glu Leu Tyr Ser Ala Ala
                805                 810                 815

Val Ser Val Gln Ala Gly Met Arg Gly Met Val Ala Arg Lys Glu Leu
                820                 825                 830

Cys Phe Arg Arg Gln Thr Lys Ala Ala Ile Ile Gln Thr Trp Cys
            835                 840                 845

Arg Gly Tyr Leu Ala Arg Leu His Tyr Arg Lys Leu Lys Lys Ala Ala
850                 855                 860

Ile Thr Thr Gln Cys Ala Trp Arg Ser Lys Val Ala Arg Gly Glu Leu
865                 870                 875                 880

Arg Lys Leu Lys Met Ala Ala Arg Glu Thr Gly Ala Leu Gln Ala Ala
                885                 890                 895

Lys Asn Lys Leu Glu Lys Gln Val Glu Glu Leu Thr Trp Arg Leu Gln
                900                 905                 910

Leu Glu Lys Arg Ile Arg Thr Asp Leu Glu Ala Lys Gln Glu
            915                 920                 925

Ser Ala Lys Ala Gln Ser Ser Leu Glu Glu Leu Gln Leu Lys Cys Lys
930                 935                 940

Glu Thr Glu Ala Leu Leu Ile Lys Glu Arg Glu Ala Ala Lys Lys Ile
945                 950                 955                 960

Ala Glu Thr Ala Pro Ile Ile Lys Glu Ile Pro Val Val Asp Gln Glu
                965                 970                 975

Leu Met Asp Lys Ile Thr Asn Glu Asn Glu Lys Leu Lys Ser Met Val
            980                 985                 990

Ser Ser Leu Glu Met Lys Ile Gly Glu Thr Glu Lys Lys Leu Gln Glu
            995                 1000                1005

Thr Thr Lys Ile Ser Gln Asp Arg Leu Asn Gln Ala Leu Glu Ala
    1010                1015                1020

Glu Ser Lys Leu Val Lys Leu Lys Thr Ala Met Gln Arg Leu Glu
    1025                1030                1035

Glu Lys Ile Leu Asp Met Glu Ala Glu Lys Lys Ile Met His Gln
    1040                1045                1050

Gln Thr Ile Ser Thr Pro Val Arg Thr Asn Leu Gly His Pro Pro
    1055                1060                1065

Thr Ala Pro Val Lys Asn Leu Glu Asn Gly His Gln Thr Asn Leu
    1070                1075                1080

Glu Lys Glu Phe Asn Glu Ala Glu Phe Thr Thr Pro Val Asp Gly
    1085                1090                1095

Lys Ala Gly Lys Ser Ala Ala Glu Arg Gln Ile Met Asn Val Asp
    1100                1105                1110

Ala Leu Ile Asp Cys Val Lys Asp Asn Ile Gly Phe Ser Asn Gly
    1115                1120                1125

Lys Pro Val Ala Ala Phe Thr Ile Tyr Lys Cys Leu Leu His Trp
    1130                1135                1140

Lys Cys Phe Glu Ser Glu Lys Thr Asn Val Phe Asp Arg Leu Ile
    1145                1150                1155

Gln Met Ile Gly Ser Ala Ile Glu Asn Glu Asp Asp Asn Ser His
    1160                1165                1170

```
Leu Ala Tyr Trp Leu Thr Ser Thr Ser Ala Leu Leu Phe Leu Leu
1175                1180                1185

Gln Lys Ser Leu Lys Thr Asn Gly Ser Gly Ala Thr Gln Ser Lys
1190                1195                1200

Lys Pro Pro Ala Ser Thr Ser Leu Phe Gly Arg Met Ala Met Ser
1205                1210                1215

Phe Arg Ser Ser Pro Ala Ser Gly Asn Leu Ala Ala Ala Ala Glu
1220                1225                1230

Ala Ala Ala Leu Ala Val Val Arg Pro Val Glu Ala Lys Tyr Pro
1235                1240                1245

Ala Leu Leu Phe Lys Gln Gln Leu Ala Ala Tyr Val Glu Lys Met
1250                1255                1260

Phe Gly Met Val Arg Asp Asn Leu Lys Arg Glu Leu Ser Thr Leu
1265                1270                1275

Leu Ser Leu Cys Ile Gln Ala Pro Arg Ser Ser Lys Gly Gly Met
1280                1285                1290

Leu Arg Ser Gly Arg Ser Phe Gly Lys Asp Ser Pro Ala Val His
1295                1300                1305

Trp Gln Ser Ile Ile Asp Gly Leu Asn Ser Leu Leu Val Thr Leu
1310                1315                1320

Lys Glu Asn His Val Pro Leu Val Leu Ile Gln Lys Ile Tyr Ser
1325                1330                1335

Gln Thr Phe Ser Tyr Ile Asn Val Gln Leu Phe Asn Ser Leu Leu
1340                1345                1350

Leu Arg Lys Glu Cys Cys Thr Phe Ser Asn Gly Glu Phe Val Lys
1355                1360                1365

Ser Gly Leu Ala Glu Leu Glu Leu Trp Cys Cys Gln Ala Lys Glu
1370                1375                1380

Tyr Ser Gly Pro Ser Trp Glu Glu Leu Lys His Ile Arg Gln Ala
1385                1390                1395

Val Gly Phe Leu Val Ile His Gln Lys Tyr Arg Ile Ser Tyr Asp
1400                1405                1410

Glu Ile Ala Asn Asp Leu Cys Pro Val Leu Ser Val Gln Gln Leu
1415                1420                1425

Tyr Arg Ile Cys Thr Leu Tyr Trp Asp Asp Ser Tyr Asn Thr Arg
1430                1435                1440

Ser Val Ser Gln Glu Val Ile Ser Ser Met Arg Thr Leu Met Thr
1445                1450                1455

Glu Glu Ser Asn Asp Ala Asp Ser Asp Ser Phe Leu Leu Asp Asp
1460                1465                1470

Asp Ser Ser Ile Pro Phe Ser Ile Asp Asp Ile Ser Ser Ser Met
1475                1480                1485

Glu Glu Lys Asp Phe Val Gly Ile Lys Pro Ala Glu Glu Leu Leu
1490                1495                1500

Glu Asn Pro Ala Phe Val Phe Leu His
1505                1510

<210> SEQ ID NO 42
<211> LENGTH: 17
<212> TYPE: PRT
<213> ORGANISM: Arabidopsis thaliana
<220> FEATURE:
<221> NAME/KEY: MISC_FEATURE
<223> OTHER INFORMATION: MYA2 Loop2
```

```
<400> SEQUENCE: 42

Phe Pro Pro Met Ser Asp Asp Ser Lys Gln Ser Lys Phe Ser Ser Ile
1               5                   10                  15

Gly

<210> SEQ ID NO 43
<211> LENGTH: 6
<212> TYPE: PRT
<213> ORGANISM: Arabidopsis thaliana
<220> FEATURE:
<221> NAME/KEY: MISC_FEATURE
<223> OTHER INFORMATION: MYA2 Loop3

<400> SEQUENCE: 43

Lys Pro Lys Leu Ala Arg
1               5

<210> SEQ ID NO 44
<211> LENGTH: 23
<212> TYPE: PRT
<213> ORGANISM: Chara braunii
<220> FEATURE:
<221> NAME/KEY: MISC_FEATURE
<223> OTHER INFORMATION: CbM1 Loop2

<400> SEQUENCE: 44

Tyr Pro Pro Pro Glu Glu Pro Lys Gln Gly Gly Lys Gly Gly Gly Lys
1               5                   10                  15

Ser Ser Phe Ser Ser Ile Gly
            20

<210> SEQ ID NO 45
<211> LENGTH: 6
<212> TYPE: PRT
<213> ORGANISM: Chara braunii
<220> FEATURE:
<221> NAME/KEY: MISC_FEATURE
<223> OTHER INFORMATION: CbM1 Loop3

<400> SEQUENCE: 45

Lys His Lys Phe Lys Lys
1               5

<210> SEQ ID NO 46
<211> LENGTH: 23
<212> TYPE: PRT
<213> ORGANISM: Chara australis
<220> FEATURE:
<221> NAME/KEY: MISC_FEATURE
<223> OTHER INFORMATION: CaM5049 Loop2

<400> SEQUENCE: 46

Tyr Pro Pro Pro Glu Glu Pro Lys Gln Gly Gly Lys Gly Gly Gly Lys
1               5                   10                  15

Ser Ser Phe Ser Ser Ile Gly
            20

<210> SEQ ID NO 47
<211> LENGTH: 6
<212> TYPE: PRT
<213> ORGANISM: Chara australis
<220> FEATURE:
<221> NAME/KEY: MISC_FEATURE
<223> OTHER INFORMATION: CaM5049 Loop3

<400> SEQUENCE: 47
```

```
Lys His Lys Phe Lys Lys
1               5

<210> SEQ ID NO 48
<211> LENGTH: 25
<212> TYPE: PRT
<213> ORGANISM: Chara braunii
<220> FEATURE:
<221> NAME/KEY: MISC_FEATURE
<223> OTHER INFORMATION: CbM2 Loop2

<400> SEQUENCE: 48

Tyr Pro Pro Pro Glu Glu Pro Lys Gln Gly Gly Gly Lys Gly Gly
1               5                   10                  15

Ser Lys Ser Ser Phe Ser Ser Ile Gly
            20                  25

<210> SEQ ID NO 49
<211> LENGTH: 6
<212> TYPE: PRT
<213> ORGANISM: Chara braunii
<220> FEATURE:
<221> NAME/KEY: MISC_FEATURE
<223> OTHER INFORMATION: CbM2 Loop3

<400> SEQUENCE: 49

Lys His Lys Phe Lys Lys
1               5

<210> SEQ ID NO 50
<211> LENGTH: 17
<212> TYPE: PRT
<213> ORGANISM: Chara braunii
<220> FEATURE:
<221> NAME/KEY: MISC_FEATURE
<223> OTHER INFORMATION: CbM3 Loop2

<400> SEQUENCE: 50

Phe Pro Pro Asp Glu Gly Thr Lys Ala Pro Ser Lys Phe Ala Ser Ile
1               5                   10                  15

Gly

<210> SEQ ID NO 51
<211> LENGTH: 6
<212> TYPE: PRT
<213> ORGANISM: Chara braunii
<220> FEATURE:
<221> NAME/KEY: MISC_FEATURE
<223> OTHER INFORMATION: CbM3 Loop3

<400> SEQUENCE: 51

Arg Pro Lys Phe Lys Arg
1               5

<210> SEQ ID NO 52
<211> LENGTH: 17
<212> TYPE: PRT
<213> ORGANISM: Chara australis
<220> FEATURE:
<221> NAME/KEY: MISC_FEATURE
<223> OTHER INFORMATION: CaM5408 Loop2

<400> SEQUENCE: 52

Phe Pro Pro Asp Glu Gly Thr Lys Ala Pro Ser Lys Phe Ala Ser Ile
1               5                   10                  15
```

Gly

```
<210> SEQ ID NO 53
<211> LENGTH: 6
<212> TYPE: PRT
<213> ORGANISM: Chara australis
<220> FEATURE:
<221> NAME/KEY: MISC_FEATURE
<223> OTHER INFORMATION: CaM5408 Loop3

<400> SEQUENCE: 53

Arg Pro Lys Phe Lys Arg
1               5

<210> SEQ ID NO 54
<211> LENGTH: 17
<212> TYPE: PRT
<213> ORGANISM: Chara australis
<220> FEATURE:
<221> NAME/KEY: MISC_FEATURE
<223> OTHER INFORMATION: CaM5627 Loop2

<400> SEQUENCE: 54

Phe Pro Pro Asp Glu Gly Thr Lys Ala Pro Ser Lys Phe Ala Ser Ile
1               5                   10                  15

Gly

<210> SEQ ID NO 55
<211> LENGTH: 6
<212> TYPE: PRT
<213> ORGANISM: Chara australis
<220> FEATURE:
<221> NAME/KEY: MISC_FEATURE
<223> OTHER INFORMATION: CaM5627 Loop3

<400> SEQUENCE: 55

Arg Pro Lys Phe Lys Arg
1               5

<210> SEQ ID NO 56
<211> LENGTH: 17
<212> TYPE: PRT
<213> ORGANISM: Chara corallina
<220> FEATURE:
<221> NAME/KEY: MISC_FEATURE
<223> OTHER INFORMATION: CcM Loop2

<400> SEQUENCE: 56

Phe Pro Ala Asp Glu Gly Thr Lys Ala Pro Ser Lys Phe Met Ser Ile
1               5                   10                  15

Gly

<210> SEQ ID NO 57
<211> LENGTH: 6
<212> TYPE: PRT
<213> ORGANISM: Chara corallina
<220> FEATURE:
<221> NAME/KEY: MISC_FEATURE
<223> OTHER INFORMATION: CcM Loop3

<400> SEQUENCE: 57

Lys His Lys Phe Lys Arg
1               5

<210> SEQ ID NO 58
<211> LENGTH: 17
```

```
<212> TYPE: PRT
<213> ORGANISM: Chara braunii
<220> FEATURE:
<221> NAME/KEY: MISC_FEATURE
<223> OTHER INFORMATION: CbM4 Loop2

<400> SEQUENCE: 58

Phe Pro Leu Asp Glu Gly Ala Lys Ala Pro Ser Lys Phe Met Ser Ile
1               5                   10                  15
Gly

<210> SEQ ID NO 59
<211> LENGTH: 6
<212> TYPE: PRT
<213> ORGANISM: Chara braunii
<220> FEATURE:
<221> NAME/KEY: MISC_FEATURE
<223> OTHER INFORMATION: CbM4 Loop3

<400> SEQUENCE: 59

Lys His Lys Phe Lys Arg
1               5

<210> SEQ ID NO 60
<211> LENGTH: 17
<212> TYPE: PRT
<213> ORGANISM: Chara australis
<220> FEATURE:
<221> NAME/KEY: MISC_FEATURE
<223> OTHER INFORMATION: CaM5639 Loop2

<400> SEQUENCE: 60

Phe Pro Ala Asp Glu Gly Thr Lys Ala Pro Ser Lys Phe Met Ser Ile
1               5                   10                  15
Gly

<210> SEQ ID NO 61
<211> LENGTH: 6
<212> TYPE: PRT
<213> ORGANISM: Chara australis
<220> FEATURE:
<221> NAME/KEY: MISC_FEATURE
<223> OTHER INFORMATION: CaM5639 Loop3

<400> SEQUENCE: 61

Lys His Lys Phe Lys Arg
1               5
```